US009567344B2

(12) United States Patent
Isaacs et al.

(10) Patent No.: US 9,567,344 B2
(45) Date of Patent: Feb. 14, 2017

(54) MOLECULAR CONTAINERS AND METHODS OF MAKING AND USING SAME

(75) Inventors: Lyle David Isaacs, Silver Spring, MD (US); Volker Briken, Laurel, MO (US); Da Ma, Carrboro, NC (US); Gaya Hettiarachchi, Arlington, VA (US); Duc M. Nguyen, Miami, FL (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 13/878,613

(22) PCT Filed: Oct. 13, 2011

(86) PCT No.: PCT/US2011/056127
§ 371 (c)(1),
(2), (4) Date: Nov. 18, 2013

(87) PCT Pub. No.: WO2012/051407
PCT Pub. Date: Apr. 19, 2012

(65) Prior Publication Data
US 2014/0094529 A1    Apr. 3, 2014

Related U.S. Application Data

(60) Provisional application No. 61/392,729, filed on Oct. 13, 2010, provisional application No. 61/392,722, filed on Oct. 13, 2010.

(51) Int. Cl.
| | | |
|---|---|---|
| C07D 487/22 | (2006.01) | |
| A61K 31/122 | (2006.01) | |
| A61K 31/787 | (2006.01) | |
| A61K 47/22 | (2006.01) | |

(52) U.S. Cl.
CPC .......... *C07D 487/22* (2013.01); *A61K 31/122* (2013.01); *A61K 31/787* (2013.01); *A61K 47/22* (2013.01)

(58) Field of Classification Search
CPC .................................................. C07D 487/22
See application file for complete search history.

(56) References Cited

U.S. PATENT DOCUMENTS

| | | |
|---|---|---|
| 6,793,839 B1 | 9/2004 | Day et al. |
| 2005/0080068 A1 | 4/2005 | Isaacs et al. |
| 2006/0182795 A1 | 8/2006 | Pun et al. |
| 2009/0072191 A1 | 3/2009 | Isaacs et al. |
| 2010/0010215 A1 | 1/2010 | Isaacs et al. |

OTHER PUBLICATIONS

Ma, D., et al. "Acyclic Cucurbit[n]uril Congeners Are High Affinity Hosts." J. Org. Chem. (2010), vol. 75, pp. 4786-4795.*
Ma, Da et al. Acyclic Cucurbit[n]uril congeners are high affinity hosts, Journal of Organic Chemistry, Jun. 14, 2010, vol. 75, pp. 4786-4795.
Brull, S. et al., Residual Neuromuscular Block: Lessons Unlearned. Part II: Methods to Reduce the Risk of Residual Weakness; Anesthesia and Analgesia [online] May 2010, vol. 111, No. 1, pp. 129-140. May 4, 2010.
Kim K., et al., Functionalized curcurbiturils and their applications, Chem. Soc. Rev. [online] Nov. 7, 2006, vol. 36, Issu. 2, pp. 1-31. Nov. 7, 2006.
Hettiarachchi, G., et al., Toxicology and Drug Delivery by Cucurbit[n]uril Type Molecular Containers, PLoS One, May 6, 2010, vol. 5, No. 5, pp. 1-10. May 6, 2010.
Lagona, J. et al. The Cucurbit[n]uril family, Angewandte Chemie Int. Ed. Aug. 5, 2005, vol. 44, pp. 4844-4870.
Wheate, Improving platinum(II)-based anticancer drug delivery using cucurbit[n]urils, J. of Inorganic Biochem., 102 (2008), pp. 2060-2066. Jun. 20, 2008.

* cited by examiner

*Primary Examiner* — Noble Jarrell
*Assistant Examiner* — John S Kenyon
(74) *Attorney, Agent, or Firm* — Hodgson Russ LLP

(57) ABSTRACT

Acyclic CB[n]-type compounds, methods of making such compounds, and uses of the compounds. For example, these compounds can be used as nanocontainers to solubilize pharmaceutical agents. Also provided are compositions and methods of using them for therapy or prophylaxis of a wide variety of conditions for which therapy or prophylaxis is desirable.

8 Claims, 26 Drawing Sheets

MOLECULAR CONTAINERS AND METHODS OF MAKING AND USING SAME

CROSS-REFERENCE TO RELATED APPLICATIONS

This application claims priority to U.S. provisional patent application Nos. 61/392,722, filed Oct. 13, 2010, and 61/392,729, filed Oct. 13, 2010, the disclosures of which are incorporated herein by reference.

STATEMENT REGARDING FEDERALLY SPONSORED RESEARCH

This invention was made with government support under grant no. CHE0615049 awarded by the National Science Foundation. The government has certain rights in the invention.

FIELD OF THE INVENTION

The present invention generally relates to molecular containers. More particularly, the present invention relates to acyclic CB[n]-type compounds, and methods of making and using such compounds.

BACKGROUND OF THE INVENTION

Only 1 out of 10,000 novel drug candidates makes it through the drug development pipelines to reach the pharmacy shelves. It is estimated that about 40% of novel drug candidates fail due to low bioavailability associated with poor aqueous solubility. Many drug candidates that exhibit high potency are abandoned by pharmaceutical companies because of poor bioavailability. One of the most common problems is that the drug candidates exhibit poor solubility in aqueous solution and therefore are difficult to formulate. One solution that has been employed by the pharmaceutical industry is to encapsulate drugs inside cyclodextrins. However, cyclodextrin-based solubility enhancement is not a universal solution. Therefore, there is an ongoing need for improved compositions for increasing solubility of pharmaceutical agents. The present invention meets these and other needs.

BRIEF SUMMARY OF THE INVENTION

The present invention provides compounds having the following structure:

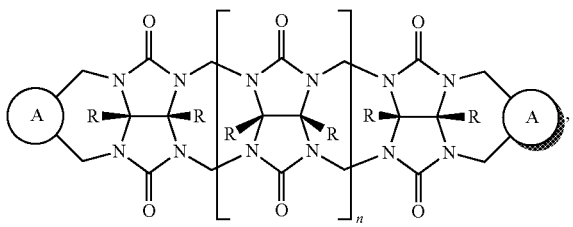

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy, or ether group. Optionally, adjacent R groups form a $C_3$ to $C_{20}$ carbocyclic ring or heterocyclic ring. Each

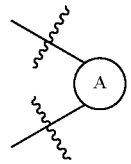

is independently a $C_5$ to $C_{20}$ carbocyclic ring system or $C_2$ to $C_{20}$ heterocyclic ring system, where the ring system comprises one or more rings. At least one of the ring systems has at least one solubilizing group selected from sulfonic acid, sulfonate salt, phosphonic acid, phosphonate salt, and polyethylene glycol. Optionally, the ring system has a targeting group. The value of n is 1 to 5.

The present invention also provides compositions comprising a compound of the present invention and a pharmaceutical agent. The pharmaceutical agent can be non-covalently complexed to the compound.

The present invention also provides a method for prophylaxis and/or therapy of a condition in an individual comprising administering to an individual in need of the prophylaxis and/or the therapy a composition comprising a compound of the present invention and pharmaceutical agent. Subsequent to the administration, the therapy and/or the prophylaxis of the condition in the individual occurs.

DETAILED DESCRIPTION OF THE INVENTION

Figure 1:
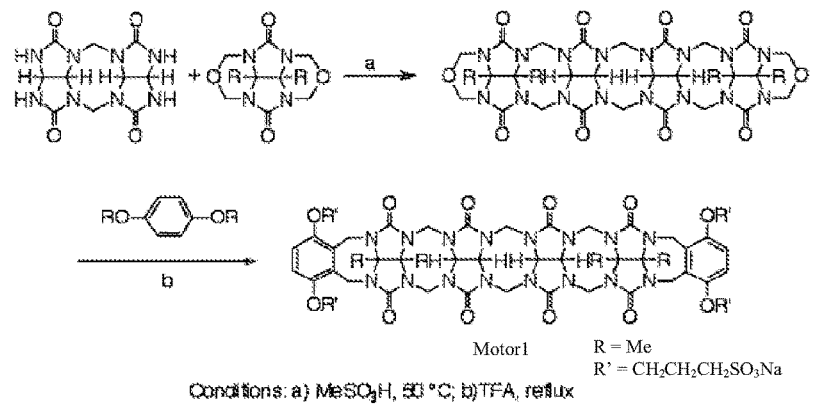
FIG. 1. Example of a Synthesis of Motor1

The present invention provides acyclic CB[n]-type compounds, compositions comprising the compounds, compositions comprising the compounds which further comprise pharmaceutical agents, methods of making the compounds and compositions comprising them, and uses of the compounds and compositions disclosed herein. The present invention is based at least in part on the surprising aqueous solubility of the acyclic CB[n]-type compounds described herein relative to previously available compounds. For example, the compounds exhibit greater than or equal to 100 mM solubility in aqueous solvents (e.g., water).

The acyclic CB[n]-type compounds of the present invention can be used for a variety of purposes, which include but are not necessarily limited to use as containers to solubilize chemical compounds. Improvement of solubility for compounds in, for example, aqueous solutions, is desirable for studying drug compounds and for improvement of drug bioavailability for therapeutic and/or prophylactic purposes. For example, the compounds of the present invention can be used to enhance the stability of drugs in both water and the solid state (e.g. decrease degradation/increase shelf life).

In certain embodiments, the compounds can be used to rescue promising drug candidates which have undesirable solubility and bioavailablity, and thus alleviate the attrition in the drug development process for anti-cancer agents and agents intended to treat other diseases. Also, the containers can be used for targeted delivery of drugs to particular cell types, such as tumor cells, to increase the efficiency of existing drugs and/or reduce their toxic side effects.

In one embodiment, the present invention provides a composition comprising at least one compound of the invention. Compositions comprising at least one compound of the invention include but are not limited to pharmaceutical preparations.

In various embodiments, the invention provides a composition comprising a compound of the invention, wherein the composition further comprises a pharmaceutical agent. Such compositions can also be provided as pharmaceutical preparations.

It is important to emphasize that the pharmaceutical agent that can be included in compositions which comprise a compound of the invention is not particularly limited. In connection with this, in certain embodiments, the pharmaceutical agent that is mixed with a compound of the invention is a pharmaceutical agent that is poorly water soluble.

Solubility of any particular pharmaceutical agent can be determined if desired using any of a variety techniques that are well known to those skilled in the art. Solubility can be ascertained if desired at any pH, such as a physiological pH, and/or at any desired temperature. Suitable temperatures for use in the invention include but are not necessarily limited to from 4° C. to 70° C., inclusive, and including all degree integers there between.

In connection with poorly soluble pharmaceutical agents suitable for use in the invention, in one aspect, such agents are considered to be those which have a solubility of less than 100 µM in water or an aqueous buffer.

In another embodiment, poorly soluble pharmaceutical agents are considered to include compounds which are Biopharmaceutics Classification System (BCS) class 2 or class 4 drugs. The BCS is well known to those skilled in the art and is based on the aqueous solubility of drugs reported in readily available reference literature, and for drugs that are administered orally it includes a correlation of human intestinal membrane permeability. (See, for example, Takagi et al., (2006) Molecular Pharmaceutics, Vol. 3, No. 6, pp 631-643.) The skilled artisan will therefore readily be able to recognize a drug as a member of BCS class 2 or class 4 from published literature, or can test a drug with an unknown BCS or other solubility value to determine whether it has properties consistent with either of those classifications, or for otherwise being suitable for use in the present invention. In one embodiment, solubility can be determined according to the parameters set forth in this matrix:

| Solubility | Parts of solvent required for 1 part of solute | Solubility Range (mg/mL) |
| --- | --- | --- |
| very soluble | <1 | ≥1000 |
| freely soluble | from 1 to 10 | 100-1000 |
| soluble | from 10 to 30 | 33-100 |
| sparingly soluble | from 30 to 100 | 10-33 |
| slightly soluble | from 100 to 1000 | 1-10 |
| very slightly soluble | from 1000 to 10000 | 0.1-1 |
| practically insoluble | ≥10000 | <0.1 |

Thus, for the purposes of the present invention, a poorly soluble pharmaceutical agent that can be mixed with a compound of the invention can be any pharmaceutical agent that falls into the categories sparingly soluble, slightly soluble, very slightly soluble, and practically insoluble as set forth in the above matrix.

Again, it should be emphasized that other than being characterized as having low solubility in aqueous solution, the pharmaceutical agent with which a compound of the invention can be mixed is not limited. In this regard, we demonstrate at least one utility of the invention by mixing a wide variety of distinct pharmaceutical agents with compounds of the invention and show that, as a consequence of mixing the compounds with the pharmaceutical agents, solubility of the agents is increased. In particular, we demonstrate this aspect of the invention by preparing compositions comprising a compound of the invention and the following illustrative types of pharmaceutical agents: a mitotic inhibitor (taxol, a mitotic inhibitor used in cancer chemotherapy); a nitrogen mustard alkylating agent (Melphalan, trade name Alkeran used for chemotherapy); a benzimidazole (Albendazole, marketed as Albenza, Eskazole, Zentel and Andazol, for treatment of a variety of worm infestations); an antagonist of the estrogen receptor in breast tissue which is used to treat breast cancers (Tamoxifen, which is an estrogen receptor antagonist when metabolized to its active form of hydroxytamoxifen); an antihistamine (Cinnarizine, marketed as Stugeron and Stunarone for control of symptoms of motion sickness); a thienopyridine class antiplatelet agent (Clopidogrel, marketed as Plavix for inhibiting blood clots in coronary artery disease and for other conditions); and an antiarrhythmic agent (Amiodarone used for treatment of tachyarrhythmias). Other pharmaceutical agents not expressly listed here are also included within the scope of the invention. Some examples of such agents include but are not limited to adjuvants for use in enhancing immunological responses, analgesic agents, and detectably labeled agents used for diagnostic imaging. Thus, it will be recognized by those skilled in the art that we have demonstrated compounds of the invention can be mixed with and improve solubility of pharmaceutical agents that are members of vastly different classes of compounds which are characterized by disparate chemical structures and biological activities. The invention accordingly provides heretofore unprecedented capability for being utilized in a broad array of therapeutic and/or prophylactic treatment modalities. Further, we demonstrate that the novel compounds provided by the invention are non-toxic to human cells. Further still, we demonstrate that by combining therapeutic agents, such as anti-cancer agents, with compounds of the invention, the therapeutic activity of the agents is increased, and in some cases a synergistic (greater than additive) increase in activity is provided.

Without intending to be constrained by theory, it is considered that one aspect of the invention provides for formation of a guest-host complex comprising a non-covalently associated complex of a compound of the invention and a pharmaceutical agent. The guest-host complex can therefore be considered to be an organized chemical entity resulting from the association of two or more components of the pharmaceutical agent (guest) and the host held together by non-covalent intermolecular forces.

Compositions comprising a compound of the invention mixed with pharmaceutical agents, which may form guest-host complexes, can be prepared at any point prior to use of the composition using any suitable technique. The compound-pharmaceutical agent complex can be formed, for example, by mixing the compound and the pharmaceutical agent in a suitable solvent. It is desirable that the compound and pharmaceutical agent be soluble in the solvent such that the compound and agent form a non-covalent complex. Any suitable solvent can be used. In certain embodiments, the solvent is an aqueous solution, which includes but is not necessarily limited to water. Non-aqueous solvents could also be used (e.g. MeOH, EtOH, or organic solvents), and then removed and the compositions if desired can be re-dissolved in an aqueous solution for administration. In general, a solution of a compound of the invention can be provided at a known concentration, examples of which include but are not limited to from 0.1 to 90 mM, inclusive and including all integers to the tenth decimal place there between, and add to that a drug for which enhanced solubility is desired. The drug can be provided, for example, in a solid form. The mixture can be shaken or stirred for a period of time and the amount of drug that is dissolved is monitored. If all added drug goes into solution, more drug can be added until some detectable portion of it remains a solid. The soluble compound-drug complex can then be isolated and analyzed by any suitable technique, such by recovering a centrifuged portion and analyzing it by NMR, to determine the concentration of drug in solution. As evidenced by the description and figures disclosed herein, in various embodiments, a compound of the invention can be provided in a composition comprising the drug at a ratio of at least 1 to 1 as pertains to the compound-drug stoichiometry.

Compositions comprising a compound of the invention and a pharmaceutical agent can be prepared at a patient's bedside, or by a pharmaceutical manufacture. In the latter case, the compositions can be provided in any suitable container, such as a sealed sterile vial or ampoule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include but are not limited to liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents.

The compositions described herein can be with one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art can be used to introduce the compositions of the invention to an individual. These methods include but are not limited to intravenous, intramuscular, intracranial, intrathecal, intradermal, subcutaneous, and oral routes. The dose of the composition comprising a compound of the invention and a pharmaceutical agent will necessarily be dependent upon the needs of the individual to whom the composition of the invention is to be administered. These factors include but are not necessarily limited to the weight, age, sex, medical history, and nature and stage of the disease for which a therapeutic or prophylactic effect is desired. The compositions can be used in conjunction with any other conventional treatment modality designed to improve the disorder for which a desired therapeutic or prophylactic effect is intended, non limiting examples of which include surgical interventions and radiation therapies. The compositions can be administered once, or over a series of administrations at various intervals determined using ordinary skill in the art, and given the benefit of the present disclosure.

Compositions of the invention can comprise more than one pharmaceutical agent. Likewise, the compositions can comprise distinct host guest complexes. For example, a first composition comprising a compound of the invention and a first pharmaceutical agent can be separately prepared from a composition which comprises the same compound of the invention and a second pharmaceutical agent, and such preparations can be mixed to provide a two-pronged (or more) approach to achieving the desired prophylaxis or therapy in an individual. Further, compositions of the invention can be prepared using mixed preparations of any of the compounds disclosed herein.

Compositions of the invention can be administered to any human or non-human animal in need of therapy or prophylaxis for one or more conditions for which the pharmaceutical agent is intended to provide a prophylactic of therapeutic benefit. Thus, the individual can be diagnosed with, suspected of having, or be at risk for developing any of a variety of conditions for which a reduction in severity would be desirable. Non-limiting examples of such conditions include cancer, including solid tumors and blood cancers (leukemia, lymphoma and myeloma). Specific examples of cancers include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, thymoma, Waldenstrom's macroglobulinemia, and heavy chain disease.

In addition to various malignancies, the invention is also suitable for providing a benefit for cardiovascular related disorders, examples of which include but are not limited to angina, arrhythmia, atherosclerosis, cardiomyopaathy, congestive heart failure, coronary artery disease, carotid artery disease, endocarditis, coronary thrombosis, myocardial infarction, hypertension, hypercholesterolemia/hyperlipidemia, mitral valve prolapse, peripheral artery disease, stroke, thrombosis, embolism, and other forms of ischemic damage.

In addition, the invention can be used in connection with treating a variety of infectious diseases. In this regard, in one embodiment, we demonstrate increased solubility of the anti-parasite drug Albendazole. Accordingly, it is expected that a variety of agents used to treat and/or inhibit infectious diseases caused by, for example, bacterial, protozoal, helminthic, fungal or viral origins could be aided by the invention.

As used herein, "alkyl group" refers to branched or unbranched hydrocarbons. Examples of such alkyl groups include methyl groups, ethyl groups, butyl groups, nonyl groups, neopentyl groups, and the like. For example, the alkyl group can be a $C_1$ to $C_{20}$ alkyl group, including all integer numbers of carbons and ranges of numbers of carbons therebetween.

As used herein, "alkyl group" refers to branched or unbranched hydrocarbons. Examples of such alkyl groups include methyl groups, ethyl groups, butyl groups, nonyl groups, neopentyl groups, and the like. For example, the alkyl group can be a $C_1$ to $C_{20}$ alkyl group, including all integer numbers of carbons and ranges of numbers of carbons therebetween.

As used herein, "carbocyclic group" refers to a cyclic compound having a ring or multiple rings in which all of the atoms forming the ring(s) are carbon atoms. The rings of the carbocyclic group can be aromatic or nonaromatic, and include compounds that are saturated and partially unsaturated, and fully unsaturated. Examples of such groups include benzene, naphthalene, 1,2-dihydronaphthalene, cyclohexane, cyclopentene, and the like. For example, the carbocyclic group can be a $C_3$ to $C_{20}$ carbocyclic group, including all integer numbers of carbons and ranges of numbers of carbons therebetween.

As used herein, "heterocyclic group" refers to a cyclic compound having a ring or multiple rings where at least one of the atoms forming the ring(s) is a heteroatom (e.g., oxygen, nitrogen, sulfur, etc.). The rings of the heterocyclic group can be aromatic or nonaromatic, and include compounds that are saturated, partially unsaturated, and fully unsaturated. Examples of such groups include imidazolidin-2-one, pyridine, quinoline, decahydroquinoline, tetrahydrofuran, pyrrolidine, pyrrolidone, and the like. For example, the heterocyclic group can be a $C_1$ to $C_{20}$ heterocyclic group, including all integer numbers of carbons and ranges of numbers of carbons therebetween.

As used herein, "carbocyclic ring system" refers to a cyclic compound having a ring or multiple rings in which all of the atoms forming the ring(s) are carbon atoms. Examples of such groups include benzene, naphthalene, 1,2-dihydronaphthalene, cyclohexane, cyclopentene, and the like. The rings of the carbocyclic ring system or heterocyclic ring system can be aromatic or nonaromatic, and include compounds that are saturated, partially unsaturated, and fully unsaturated. For example, the carbocyclic ring system can be a $C_3$ to $C_{20}$ carbocyclic group, including all integer numbers of carbons and ranges of numbers of carbons therebetween. In another example, the carbocyclic ring system can be a phenyl group or naphthyl group. The phenyl group or naphthyl group is attached to the compound via adjacent carbons of the phenyl group or naphthyl group.

As used herein, "heterocyclic ring system" refers to a cyclic compound having a ring or multiple rings in which at least one of the atoms forming the ring(s) is a heteroatom (e.g., oxygen, nitrogen, sulfur, etc.). The rings of the carbocyclic ring system or heterocyclic ring system can be aromatic or nonaromatic, and include compounds that are saturated, and fully unsaturated. Examples of the heterocyclic ring system include imidazolidin-2-one, pyridine, quinoline, decahydroquinoline, tetrahydrofuran, pyrrolidine, pyrrolidone, and the like. For example, the heterocyclic ring system can be a $C_1$ to $C_{20}$ heterocyclic group, including all integer numbers of carbons and ranges of numbers of carbons therebetween.

Any of these groups and/or rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups. For example, the alkyl groups or aryl groups may be further substituted. For example, the alkyl group can be halide substituted (e.g., a 2-chloroethyl group). As another example, a carbocyclic group can be cyano substituted (e.g., 3-cyano naphthalene).

In an aspect, the present invention provides acyclic CB[n]-type compounds having the following structure:

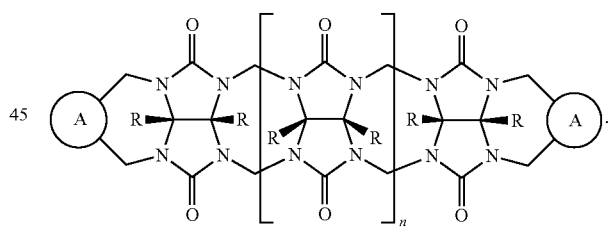

Each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl, or ether group. The carboxylic acid, ester, amide, and ether groups can have from 1 to 20 carbons, including all integer values and ranges therebetween. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups.

Each

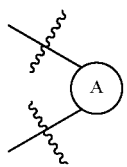

is independently a $C_5$ to $C_{20}$ carbocyclic ring system or $C_2$ to $C_{20}$ heterocyclic ring system. At least one

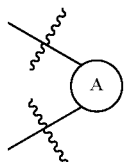

of the compound has at least one solubilizing group. In an embodiment, both

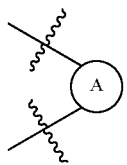

s of the compound have at least one solubilizing group. In an embodiment, one

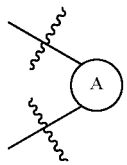

of the compound has at least one solubilizing group. In various embodiments, the ring system has 1, 2, 3, 4, 5, or 6 solubilizing groups. Optionally, the ring system has a targeting group. The value of n is 1 to 5, including all integer values therebetween. In an embodiment, the

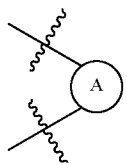

groups are the same.

In various embodiments, the compound is a salt, a partial salt, a hydrate, a polymorph, a stereoisomer or a mixture thereof. The compounds can have stereoisomers. For example, the compound can be present as a racemic mixture, a single enantiomer, a single diastereomer, mixture of enantiomers, or mixture of diastereomers.

Without intending to be bound by any particular theory, it is considered that the solubilizing group (or groups) increase (or impart) solubility of compounds in water or aqueous solvent systems. The solubilizing group can be a functional group that can be deprotonated over a broad pH range. The solubilizing group can have a cationic (e.g., ammonium and sulfonium groups), anionic (e.g., sulfate, sulfonate, phosphate, and phosphonate groups) or neutral group (e.g., sulfonic acids, phosphonic acids, polyethylene glycol (PEG) ethers (including PEG ether oligomers), crown ethers, and cyclam groups). Another example of a neutral solubilizing group is a zwitterionic group (e.g., a group with both an ammonium group and a sulfonate group), where both ionic groups are covalently bonded to the compound. It is desirable that cationic solubilizing groups not interact with cavity of the compound. The compound can have mixtures of solubilizing groups. In an embodiment, the solubilizing group selected from sulfonic acid, sulfonate salt, phosphonic acid, phosphonate salt, and polyethylene glycol. The solubilizing group can be connected to the linking group though a heteroatom, such as oxygen or sulfur. For example, the PEG group can be connected to the compound through a sulfur atom forming a thioether moiety. For example, the polyethylene glycol group can have a molecular weight of from 107 to 100,000, including all integer values and ranges therebetween.

In one embodiment, the solubilizing group or groups are not carboxylic acids or carboxylic acid salts. In one embodiment, at least one of the solubilizing groups is not a carboxylic acid or carboxylic acid salt.

The targeting group is a moiety that interacts with, for example, a cell. A targeting group (TG) is a moiety that targets, for example, tumor cells by either passive or active targeting by methods known in the art. Examples of targeting groups include dendrons, dendrimers, PEG groups, peptides, polypeptides, folates, amidines, antibodies, proteins, steroids, mono or oligosaccharides, and the like.

In an embodiment, each

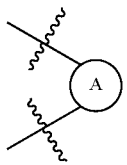

of the compound is independently a $C_5$ to $C_{20}$ carbocyclic ring system having one of the following structures:

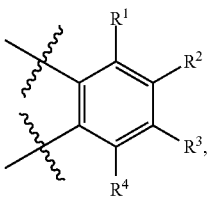 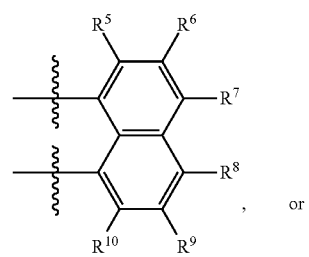

-continued

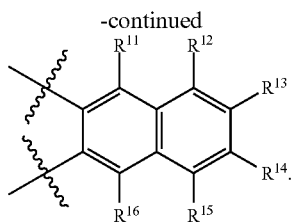

At each occurrence of

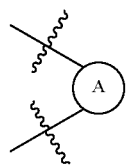

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of $R^1$ to $R^{16}$ in the compound has the following structure:

LG is a linking group and X is the solubilizing group. Optionally, one or more adjacent $R^1$ to $R^{16}$ groups are connected forming a carbocyclic or heterocyclic ring, and the ring can be substituted or unsubstituted.

As used herein, "adjacent" refers to groups attached through 2 or 3 carbons as depicted by, for example,

in the structures:

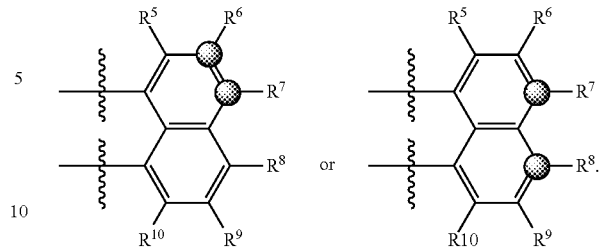

It is contemplated that groups can be attached through any two adjacent carbons.

A linking group (LG) is a group that connects

with a solubilizing group (X) or a targeting group (TG). The linking group can be, for example, an alkoxy moiety or an alkyl moiety. The linking group can have independently at each occurrence a thioether linkage, ether linkage, amino linkage, amide linkage, ester linkage, triazole ring linkage, or a combination thereof. For example, these linkages can join the linking group and solubilizing group or targeting group. In an embodiment, the linking group, LG, is a 1-substituted triazole.

In an embodiment,

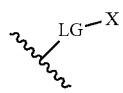

has the following structure:

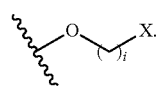

The value of each i is independently 1 to 20, including all integer values therebetween.

In an embodiment, at least one of the $R^1$ to $R^{16}$ groups in the compound has the following structure:

LG is a linking group and TG is a targeting group.

In an embodiment, the compound has one of the following structures:

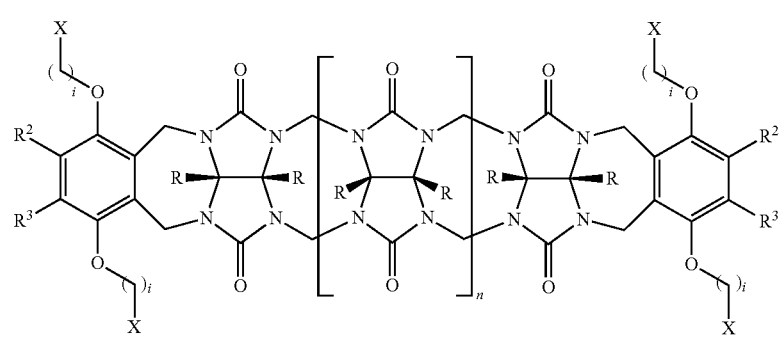

(I)

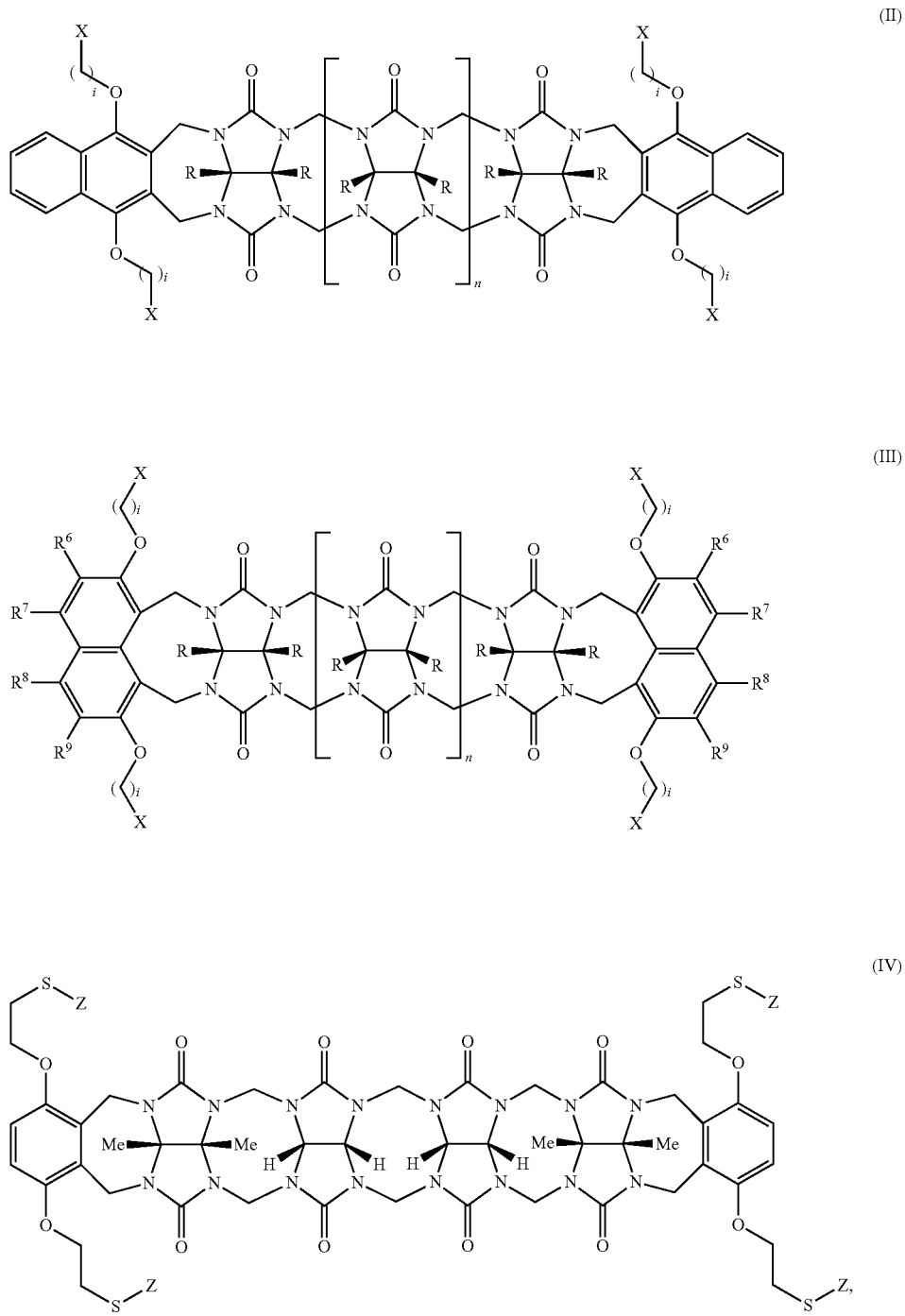

wherein Z is PEG group. In an embodiment, the PEG group has a molecular weight of 200 to 10,000, including all integers and ranges therebetween. In an embodiment, the PEG group has a molecular weight of 350 (PEG350), 750 (PEG750), 1900 (PEG1900), or 5000 (PEG5000).

Compounds having the structures of formulae I-IV can be prepared, for example, by the synthetic methodology described in Example 1-2. In this embodiment, R, $R^2$, $R^3$, $R^6$, $R^7$, $R^8$ and $R^9$ are as defined herein.

In various embodiments, the compounds have the following structures:
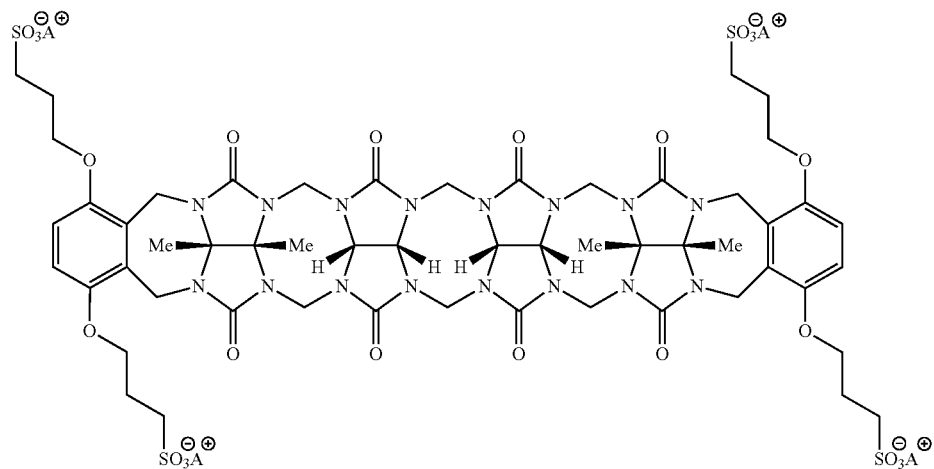
(referred to herein as Motor1 or Motor 1),
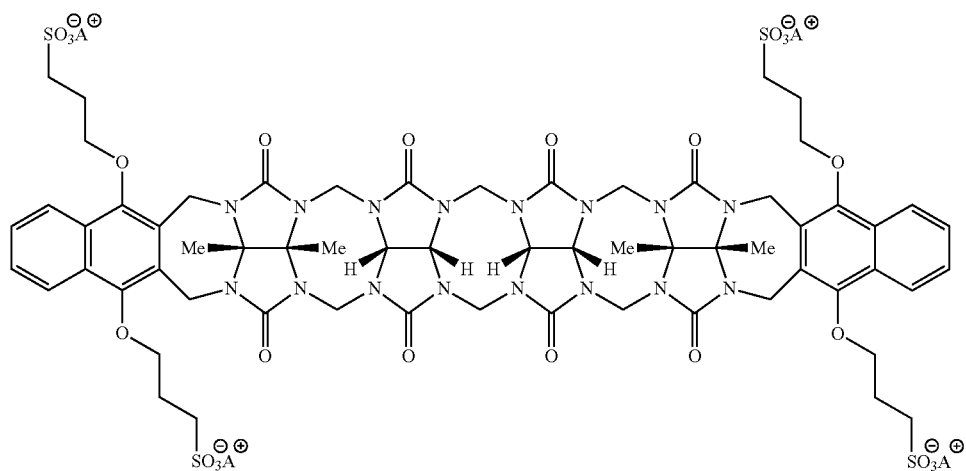
(referred to herein as Motor2 or Motor 2),
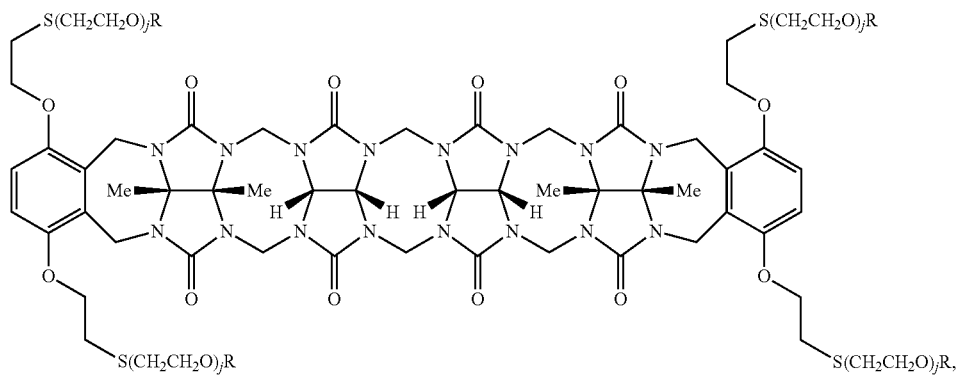

where j is, for example, 1 to 2250, including all integer values and ranges therebetween, and R in this example is hydrogen or an alkyl group,
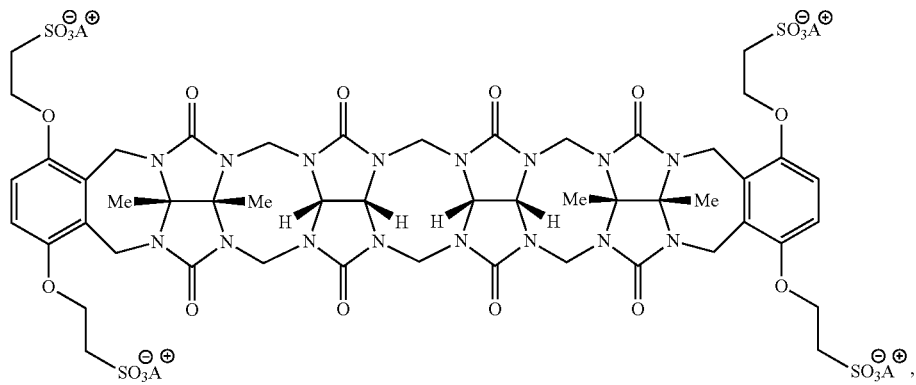
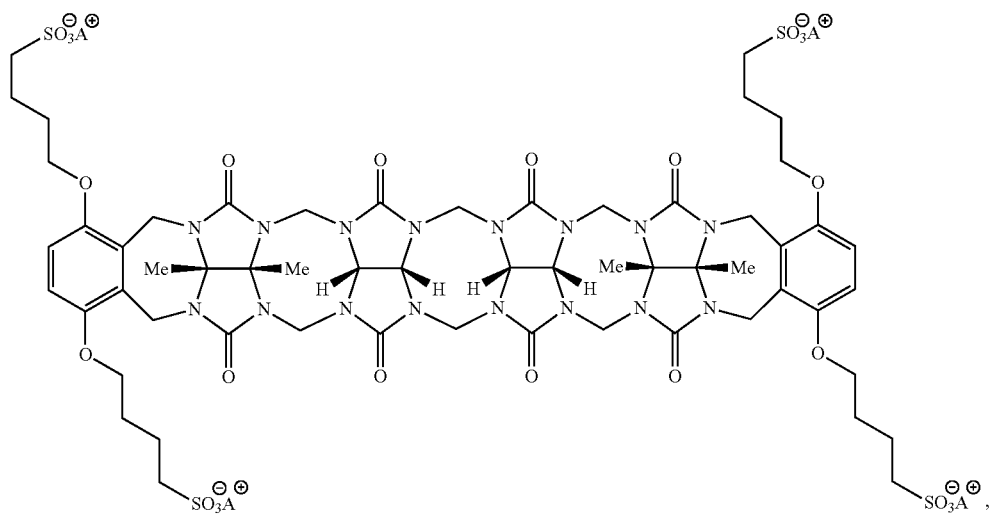
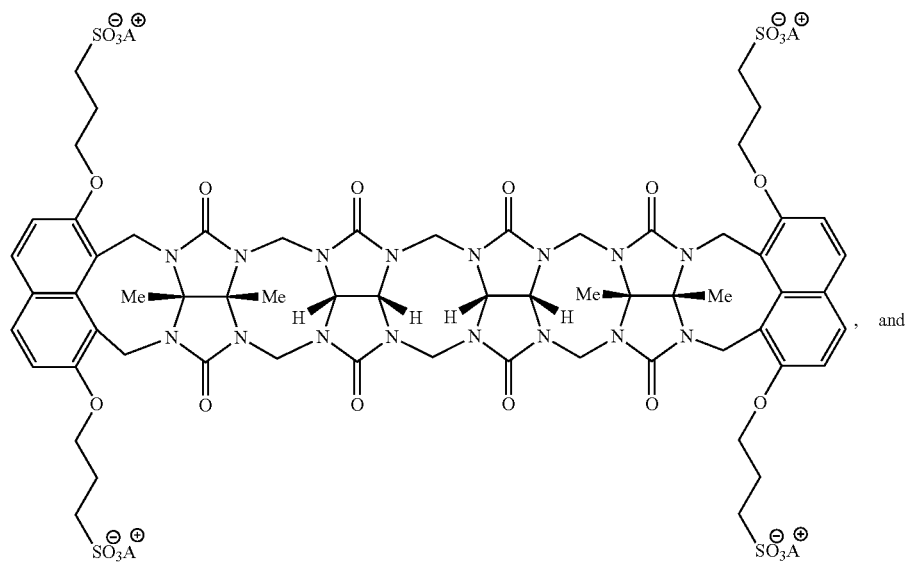

-continued

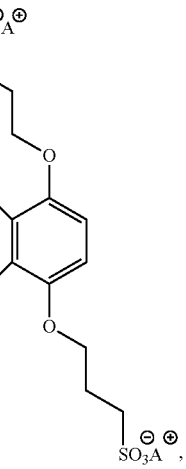

where A⁺ can be $H^+$, $Na^+$, $K^+$, $Ca^{2+}$, $Mg^{2+}$, $Zn^{2+}$, $H_4N^+$, $Et_3NH^+$, $Me_4N^+$, $(HOCH_2CH_2)_3NH^+$, or a cationic form of ethylenediamine, piperazine, and trishydroxymethyl aminomethane (TRIS).

The compound-pharmaceutical agent complex can be formed, for example, by mixing the compound and the pharmaceutical agent in a suitable solvent. It is desirable that the compound and pharmaceutical agent be soluble in the solvent such that the compound and agent form a non-covalent complex.

An example of a general method for the preparation of the compounds of the present invention is provided in the following. The method comprises the following steps:

1) Providing a compound (1) of the following structure:

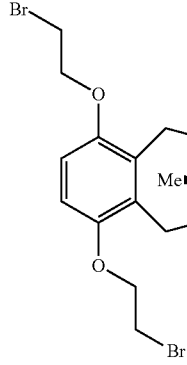

(1)

where m is from 0 to 4,

2) Forming a reaction mixture comprising compound (1), an acid (e.g., $MeSO_3H$, HCl, $CF_3CO_2H$, $H_2SO_4$, or TsOH) and a compound (2) having the following structure:

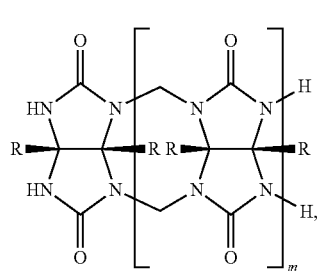

(2)

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl group, or ether group. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups. Y is oxygen or nitrogen substituted with a $C_1$ to $C_{20}$ alkyl group. (2) is added to the reaction mixture such that a compound (3), of the following structure is formed:

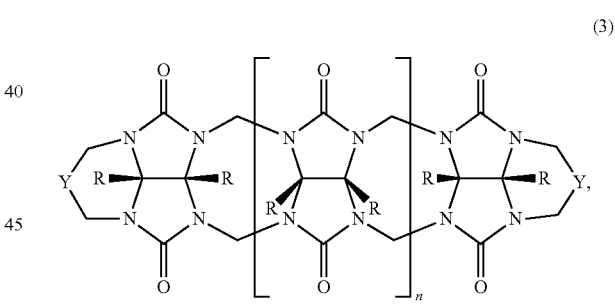

(3)

3) Contacting said compound (3) with TFA and

, which can be a $C_5$ to $C_{20}$ carbocyclic ring system or $C_2$ to $C_{20}$ heterocyclic ring system, where the ring system comprises one or more rings. The ring system, optionally, has at least one solubilizing group. Optionally, the ring system has a targeting group. Compound (3), a solvent, and

are combined such that the following structure is formed:

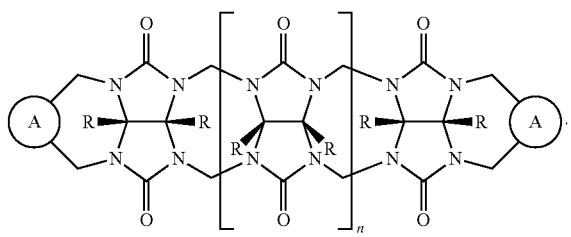

In an embodiment,

can be derivatized with the solubilizing group and/or targeting group after step 3). For example, one of the building block compounds can be derivatized to form a compound of the present invention. For example, an alkyl bromide component of one of the building block compounds can be reacted with a PEGylated thiol to make a compound with a PEG solubilizing group.

Examples of

include but are not limited to:

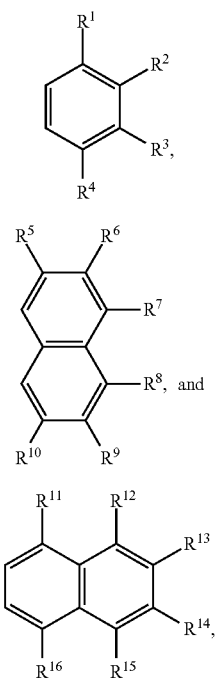

where each $R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of the $R^1$ to $R^{16}$ groups in the structure has the following structure:

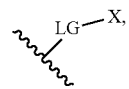

where LG is the linking group and wherein X is the solubilizing group. In an embodiment, LG can have the formula:

where each i is 1 to 20. Optionally one or more adjacent $R^1$ to $R^{16}$ groups are connected forming a carbocyclic or heterocyclic ring, and the ring can be substituted or unsubstituted. In an embodiment, at least one of the $R^1$ to $R^{16}$ groups in the structure has the following structure:

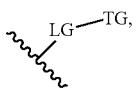

where LG is a linking group and wherein TG is the targeting group.

It is desirable for the

group to be reactive in electrophilic aromatic substitution reactions. Thus, in an embodiment, the

group is an aromatic ring having at least one alkyl ether moiety.

The determination of suitable reaction conditions (e.g., solvent, reaction time and reaction temperature) is within the purview of one having skill in the art. A wide range of solvent can be used. Examples of suitable solvents include TFA, HCl, $H_2SO_4$, TsOH, HBr, $CH_3SO_3H$ and mixtures thereof. For example, it may be desirable to add acetic anhydride as a co-solvent. Reaction time can vary. Generally, a reaction time of 3 hours is sufficient to provide a desired extent of reaction. A wide range of reaction temperatures can be used. For example, reaction temperatures of 25° C. to 100° C. can be used.

In an embodiment, the compounds can be made from building block compounds (i.e., intermediates). The building block compounds have functional groups (e.g., halogen (e.g., fluoro, chloro, bromo, or iodo), hydroxy, carboxylic acid, alkenyl, alkynyl, nitro, cyano, keto, amino, amido, thioether, thioate and triazole groups) that can be reacted to covalently attach solubilizing groups or targeting groups. Examples of building block compounds include:
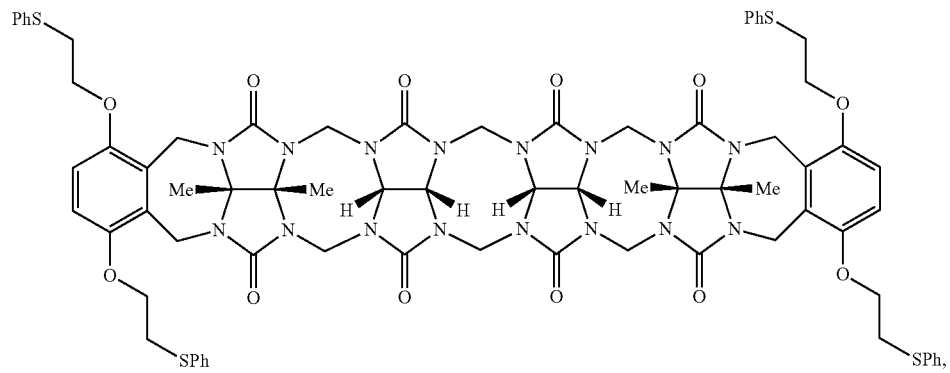
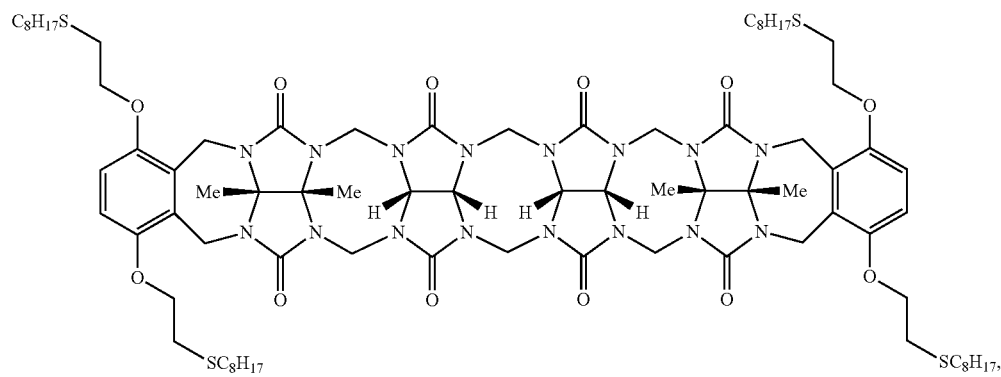
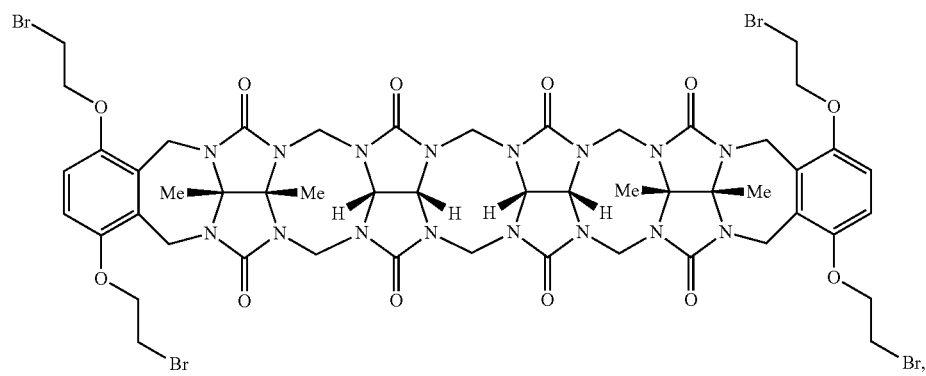
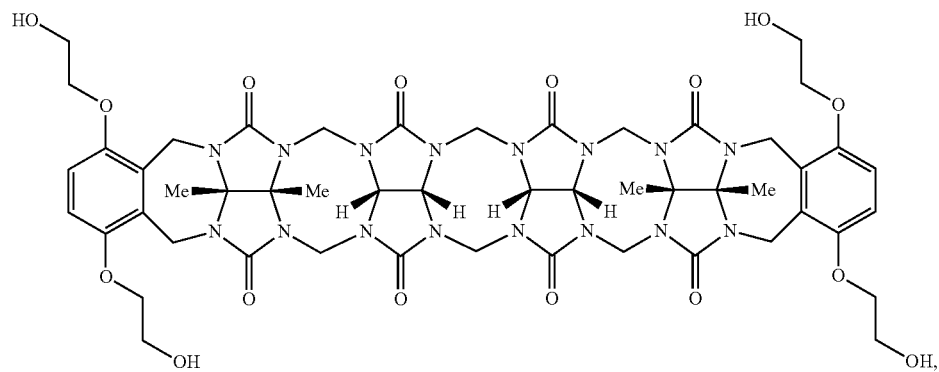

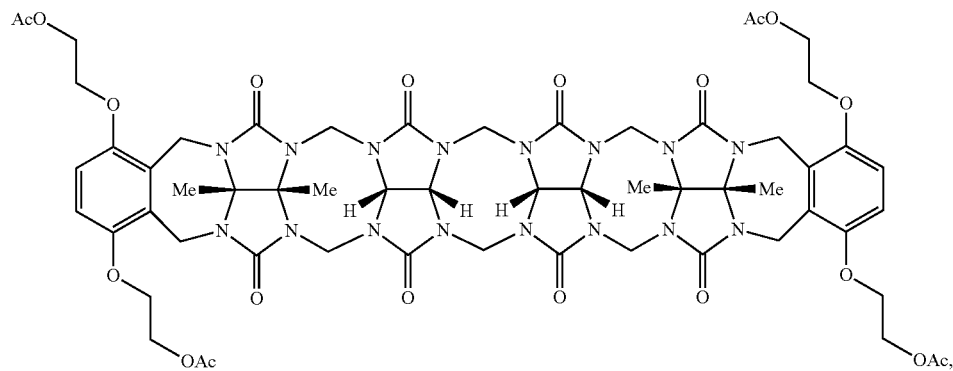
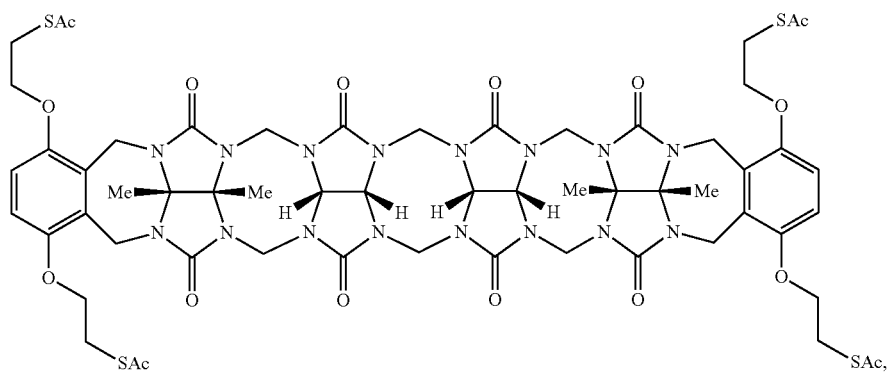
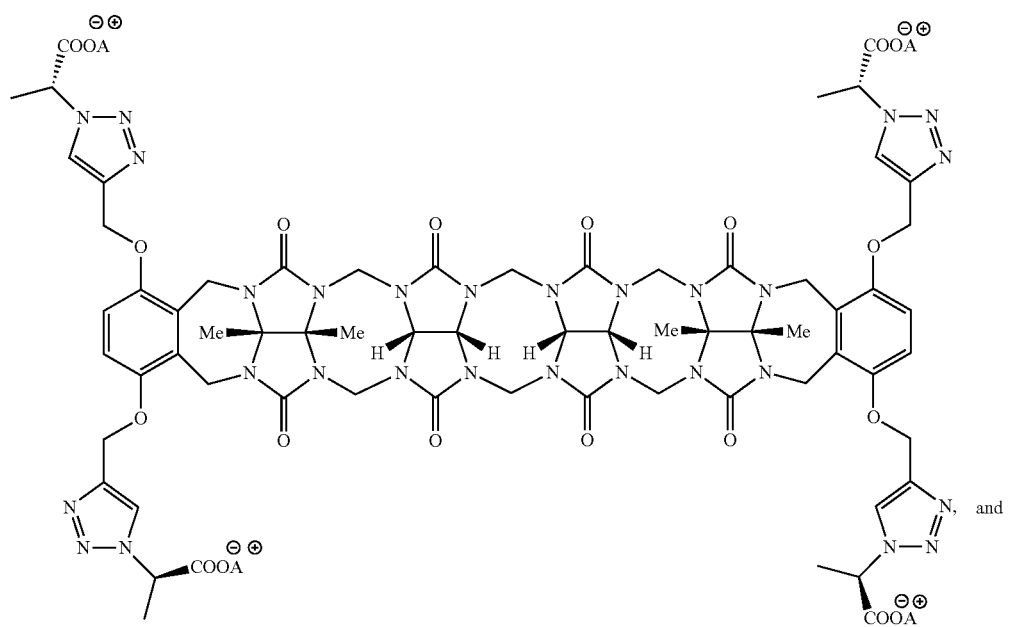

-continued

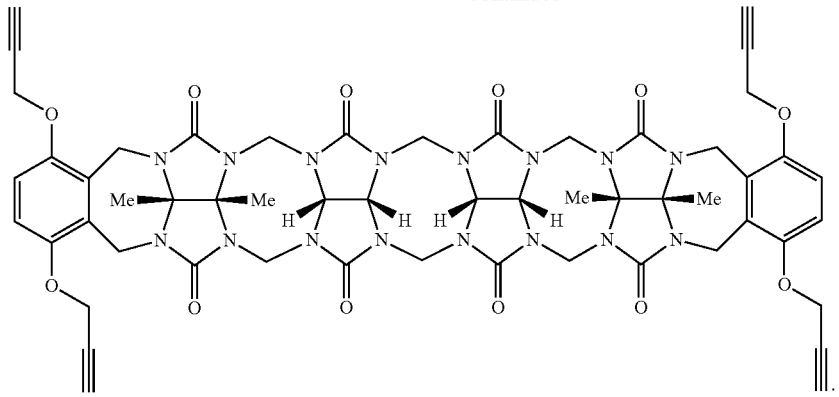

For example, the tetra propargyl compound can be reacted with azides to form for example a triazole compound.

The following examples are presented to illustrate the present invention. They are not intended to limiting in any manner.

Example 1

General Experimental

Starting materials were purchased from commercial suppliers and were used without further purification or were prepared by literature procedures. Melting points were measured on a Meltemp apparatus in open capillary tubes and are uncorrected. IR spectra were recorded on a JASCO FT/IR 4100 spectrometer and are reported in cm$^{-1}$. NMR spectra were measured on Bruker DRX-400 instrument operating at 400 MHz for $^1$H and 100 MHz for $^{13}$C. Mass spectrometry was performed using a JEOL AccuTOF electrospray instrument (ESI). UV-Vis absorbance was measured on Varian Cary 100 UV spectrophotometer.

Synthetic Procedures and Characterization.

Glycoluril Dimer. A mixture of glycoluril (500 g, 3.51 mol) and paraformaldehyde (105 g, 3.51 mol) in HCl (8 M, 70 mL) was heated at 50° C. for 48 h. The reaction mixture was cooled and filtered. The solid was washed with water (500 mL) and then recrystallized with TFA (1.5 L) to yield Glycoluril Dimer as a white solid (334 g, 62%).

Dimethyl Glycoluril.

Into a solution of urea (1140 g, 19.0 mol) in HCl (0.3 M, 2.8 L), 2, 3-butanedione (500 g, 5.8 mol) was added. The solution was stirred at RT for 12 h. The reaction mixture was filtered and the solid was washed with water (2.0 L×2) and then ethanol (2.0 L) to yield Dimethyl glycoluril as a white solid (749 g, 76%).

Dimethyl Glycoluril Bis(Cyclic Ether).

A mixture of Dimethyl glycoluril (749 g, 4.4 mol) and paraformaldehyde (650 g, 21.7 mol) in HCl (9 M, 3.8 L) was stirred for 24 h. Water (14.0 L) was added and the mixture was stirred for an additional 12 h. The mixture was then filtered and washed with water (2 L) and ethanol (2 L) to yield Dimethyl glycoluril bis(cyclic ether) as a white solid (719 g, 65%).

Methyl Tetramer. (FIG. 1)

Into a solution of Glycoluril Dimer (84 g, 0.27 mol) in anhydrous MeSO$_3$H (600 mL), Dimethyl glycoluril bis (cyclic ether) (304 g, 1.20 mol) was added. The reaction mixture was stirred and heated at 50° C. for 3 h. The reaction mixture was poured into water (6.0 L). After filtration, the crude solid was dried in high vacuum. The crude solid was recrystallized from TFA (350 mL) and water (1.4 L) to yield Methyl tetramer as a white solid (76 g, 36%).

Propanesulfonate Wall.

Into a solution of hydroquinone (100 g, 0.91 mol) in aqueous NaOH solution (2.5 M, 1.4 L), a solution of propanesultone (275 g, 2.25 mol) in 1,4-dioxane (1.8 L) was added. The mixture was stirred at RT for 12 h. The mixture was filtered. The solid was washed with acetone (2 L×2) to yield 3,3'-(1,4-phenylenebis(oxy))bis(propane-1-sulfonic acid) as white solid (294 g, 81%).

Motor1. (FIG. 1)

Into a solution of methyl tetramer (76 g, 97 mmol) in TFA (700 mL), propanesulfonate wall (154 g, 387 mmol) was added. The mixture was stirred and heated at 70° C. for 3 h. The solvent was removed by rotary evaporation and the solid was dried in high vacuum. The solid was washed with the mixture of water and acetone (1:2, v/v, 1.5 L×2). The solid was dissolved in water (500 mL) and adjusted to pH=7 by adding 1 M aqueous NaOH. The solvent was removed with rotary evaporation and then the solid was further dried under high vacuum to yield Motor1 as a white solid (60 g, 40%). M.p.>320° C. (decomposed). IR (ATR, cm−1): 3000w, 1711s, 1456s, 1313m, 1225s, 1178s, 1076s, 972m, 920m, 822m, 797s, 756m, 665m. $^1$H NMR (400 MHz, D$_2$O): 6.72 (s, 4H), 5.50 (d, J=15.2, 2H), 5.38 (d, J=15.7, 4H), 5.31 (d, J=9.0, 2H), 5.25 (d, J=8.9, 2H), 5.19 (d, J=16.2, 4H), 4.10 (d, J=11.1, 4H), 4.06 (d, J=11.7, 4H), 3.97 (d, J=15.4, 2H), 3.91 (m, 4H), 3.79 (m, 4H), 2.98 (m, 8H), 2.06 (m, 8H), 1.64 (m, 6H), 1.61 (s, 6H). $^{13}$C NMR (100 MHz, D$_2$O, 1,4-dioxane as internal reference): δ 157.5, 157.3, 150.8, 128.3, 115.3, 79.7, 78.6, 72.3, 72.1, 69.2, 53.8, 49.4, 49.0, 35.9, 25.5, 17.1, 16.0. MS (ESI): m/z 1473.3232 ([M−H]−), calculated 1473.3216.

Figure 2:
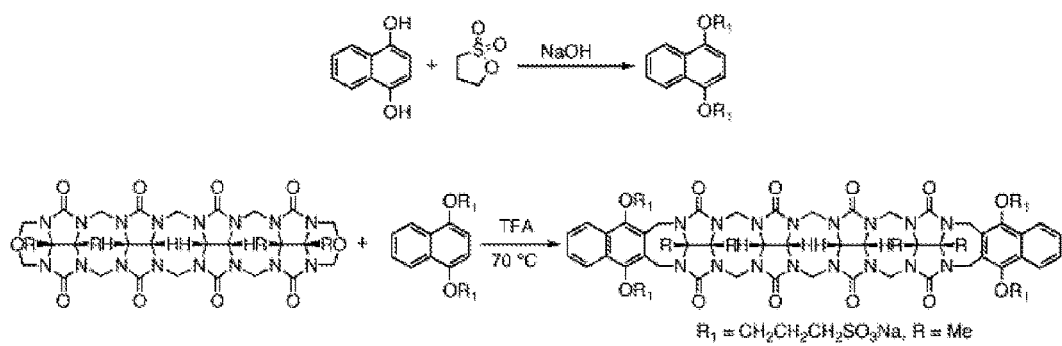
FIG. 2. Example of a Synthesis of Motor2

1,4-Naphthalene Propanesulfonate Wall (FIG. 2).

Into a solution of 1,4-dihydroxynaphathelene (2.0 g, 12.5 mmol) in NaOH (10 wt %, 16 mL), a solution of propanesultone (3.8 g, 31.2 mmol) in 1,4-dioxane (24 mL) was added. This solution was stirred at RT for 12 h. After filtration, the solid was dissolved in H2O (10 mL) and then precipitated with MeCN (60 mL) to yield a blue solid (1.5 g, 3.3 mmol, 27%). M.p.>227° C. (dec.). IR (ATR, cm$^{-1}$): 2988w, 2902w, 1597w, 1462w, 1377w, 1273m, 1240m, 1222m, 1183s, 1155m, 1100m, 946s, 800w, 765m, 613m. $^1$H NMR (600 MHz, D2O): 8.01 (m, 2H), 7.43 (m, 2H), 6.63 (s, 2H), 4.02 (t, 4H), 3.02 (t, 4H), 2.16 (m, 4H). $^{13}$C NMR (125 MHz, D$_2$O, 1,4-dioxane as internal reference): δ 148.0, 126.4, 125.9, 121.4, 106.3, 67.5, 48.1, 24.2. High-Res MS (ESI): m/z 427.0528 ([M+Na]$^+$), calculated 427.0497.

Motor2 (FIG. 2).

To a solution of methyl tetramer (2.67 g, 3.42 mmol) in TFA (25 mL), 1,4-Naphthalene propanesulfonate wall (6.13 g, 13.7 mmol) was added. This solution was stirred and heated at 70° C. for 3 h. The solvent was removed with rotary evaporation and the solid was dried in high vacuum. The crude mixture was refluxed in EtOH (60 mL) overnight and then filtered. The solid was dissolved in hot water (20 mL). The solution was adjusted to pH=7 with 1 M NaOH. The solution was cooled down to RT and filtered to yield Motor2 as a white solid (1.7 g, 30%). M.p.>196° C. (decomposed). IR (ATR, cm$^{-1}$): 3433w, 1717s, 1471s, 1425m, 1383m, 1349m, 1317m, 1179s, 1082s, 1036s, 922w, 881w, 827m, 801s, 757m, 728m, 676m. $^1$H NMR (600 MHz, D$_2$O): 7.72 (m, 4H), 7.27 (m, 4H), 5.48 (d, J=15.3, 2H), 5.42 (d, J=15.7, 4H), 5.31 (d, J=8.9, 2H), 5.25 (d, J=8.9, 2H), 5.12 (d, J=16.0, 4H), 4.30 (d, J=16.0, 4H), 4.12 (d, J=15.7, 4H), 4.00 (m, 4H), 3.96 (d, J=15.3, 2H), 3.74 (m, 4H), 3.08 (m, 8H), 2.13 (m, 8H), 1.66 (s, 6H), 1.61 (s, 6H). $^{13}$C NMR (125 MHz, D$_2$O, 1,4-dioxane as internal reference): δ 156.7, 156.3, 148.2, 127.7, 127.0, 126.1, 122.3, 78.6, 77.6, 74.1, 71.5, 71.2, 52.9, 48.5, 36.5, 25.1, 16.4, 15.2. High-Res MS (ESI): m/z 777.1986 ([M+2H]$^{2+}$), calculated 777.1972.

Example 2

Figure 3:
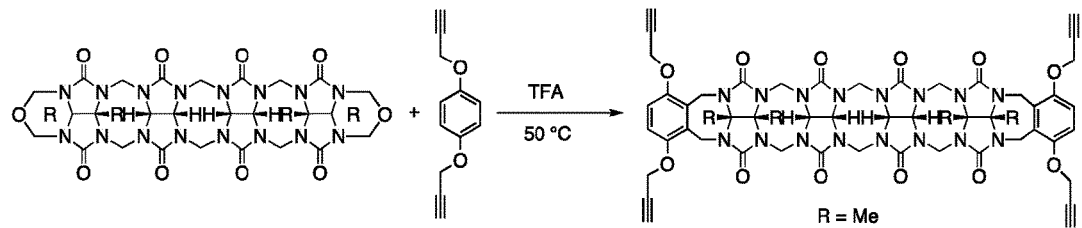
FIG. 3. Example of a Synthesis of Propargyl Host

Propargyl Host (FIG. 3)

Methyl tetramer (1.70 g, 2.18 mol) in TFA (5 mL), 1,4-bis(prop-2-yn-1-yloxy)benzene (1.62 g, 8.71 mmol) was added. The solution was heated at 50° C. for 4 h. The solvent was removed with rotary evaporation. The crude product was further dried on high vacuum and then washed with water (50 mL). The solid was washed with acetone (50 mL×2) and filtered. Then this solid was dissolved in concentrated HCl (50 mL) and then precipitated by adding water (100 mL) to yield a white solid (1.1 g, 1.0 mmol, 45%). M.P.>260° C. (decomposed). IR (ATR, cm$^{-1}$): 2939w, 1721m, 1463m, 1380m, 1314w, 1231m, 1211m, 1186m, 1090m, 941s, 848w, 796m, 758m, 616m. $^1$H NMR (400 MHz, D$_2$O): 6.92 (s, 4H), 5.54 (d, J=14.9, 2H), 5.45 (d, J=15.0, 4H), 5.34 (d, J=9.0, 2H), 5.23 (d, J=9.0, 2H), 5.15 (d, J=15.8, 4H), 4.79 (d, J=15.0, 4H), 4.72 (d, J=15.0, 4H), 4.10 (d, J=15.8, 4H), 4.03 (d, J=15.0, 4H), 4.03 (d, J=14.9, 2H), 3.52 (s, 4H), 1.65 (s, 6H), 1.61 (s, 6H). $^{13}$C NMR (125 MHz, DMSO-d$^6$): δ 156.6, 155.2, 150.7, 129.6, 115.6, 81.3, 79.1, 78.5, 77.5, 71.9, 71.5, 59.0, 54.2, 49.4, 35.6, 18.0, 16.9. HR-MS (ESI): m/z 1117.4007 ([M+H]$^+$), calculated 1117.4029.

Figure 4:
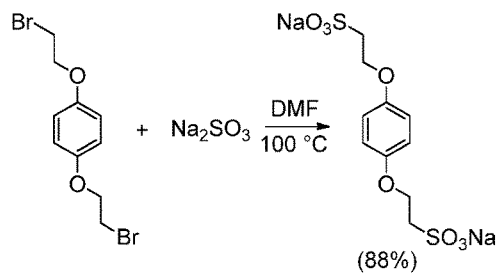
FIG. 4. Example of a Synthesis of Ethanesulfonate Wall

Ethanesulfonate Wall (FIG. 4).

1,4-bis(2-bromoethoxy)benzene (2.00 g, 6.13 mmol) and sodium sulfite (3.10 g, 24.5 mmol) were mixed and dissolved in DMF (20 mL). The mixture was stirred at 100° C. under N$_2$ for 12 h and then water (20 mL) was added. The mixture was allowed to cool to RT and the product precipitated as white crystals. The solid was collected by filtration and then purified by recrystallization from water. Drying under high vacuum gave Sodium 2,2'-(1,4-phenylenebis(oxy))diethanesulfonate as a white solid (2.01 g, 88%). $^1$H NMR (400 MHz, D$_2$O): 7.03 (s, 4H), 4.39 (t, J=6.2, 4H), 3.36 (t, J=6.2, 4H). $^{13}$C NMR (125 MHz, D$_2$O, 1,4-dioxane as internal reference): δ 151.5, 115.5, 63.3, 49.3.

Figure 5:
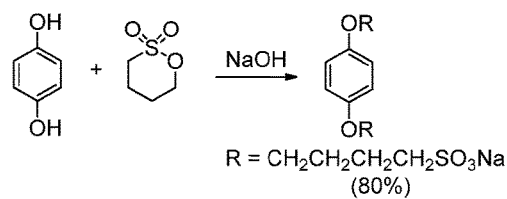
FIG. 5. Example of a Synthesis of Butanesulfonate Wall

Butanesulfonate Wall (FIG. 5).

A solution of butanesultone (24.5 g, 200 mmol) in 1,4-dioxane (160 mL) was added into a solution of hydroquinone (8.80 g, 80.0 mmol) in aqueous NaOH solution (10 wt %, 120 mL). The mixture was stirred at RT for 12 h then filtered to collect the crude solid. The solid was stirred with acetone (200 mL) then dried under high vacuum to yield Sodium 4,4'-(1,4-phenylenebis(oxy))dibutane-1-sulfonate as a white solid (25.1 g, 80%). $^1$H NMR (400 MHz, D$_2$O): 7.02 (s, 4H), 4.09 (t, J=5.7, 4H), 2.99 (t, J=7.4, 4H), 1.85-2.00 (m, 8H). $^{13}$C NMR (125 MHz, D$_2$O, 1,4-dioxane as internal reference): δ 152.1, 115.8, 68.3, 50.2, 26.8, 20.4.

Figure 6:
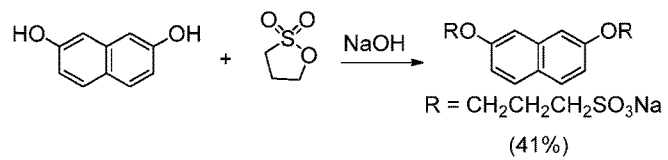
FIG. 6. Example of a Synthesis of 2,7-naphthalene sulfonate Wall

2,7-Naphthalenesulfonate Wall (FIG. 6).

A solution of propanesultone (38.0 g, 300 mmol) in 1,4-dioxane (240 mL) was added into a solution of naphthalene-2,7-diol (20.0 g, 124 mmol) in NaOH (10 wt %, 160 mL). This solution was stirred at RT for 12 h. After filtration, the solid was collected and then dissolved in H$_2$O (100 mL) and then was precipitated by the addition of CH$_3$CN (600 mL). The solid was collected by filtration and then dried under high vacuum to yield a pale green solid (23.2 g, 41%). $^1$H NMR (400 MHz, D$_2$O): 7.77 (d, J=8.9, 2H), 7.23 (m, 2H), 7.07 (dd, J=8.9, 2.4, 2H), 4.24 (t, J=6.4, 4H), 3.05-3.15 (m, 4H), 2.15-2.30 (m, 4H). $^{13}$C NMR (125 MHz, D$_2$O, 1,4-dioxane as internal reference): δ 156.2, 135.0, 128.9, 123.9, 115.8, 106.3, 66.0, 47.4, 23.7.

Figure 7:
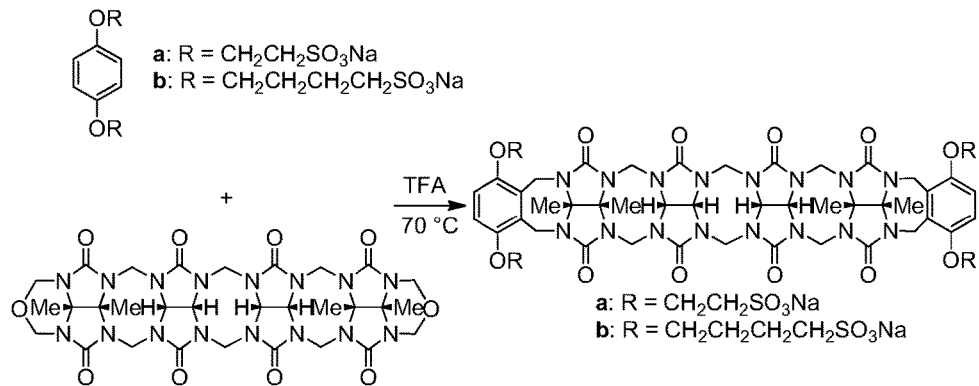
FIG. 7. Example of Syntheses of Ethanesulfonate Host and Butanesulfonate Host FIG. 8. Example of a Synthesis of Napthalene Propanesulfonate Host FIG. 9. Example of a Synthesis of Tetrabromo Host FIG. 10. Example of a Synthesis of Tetrathiophenyl Host FIG. 11. Example of a Synthesis of Tetraoctanethioether Host FIG. 12. Example of Syntheses of PEG350, PEG750, PEG1900, PEG5000 Hosts FIG. 13. Example of a Synthesis of Dibromo Dipropanesulfonate Host FIG. 14. Example of a Synthesis of Tetraester Host FIG. 15. Example of a Synthesis of Tetrahydroxy Host FIG. 16. Example of a Synthesis of Tetrathioacetate Host FIG. 17. Example of a Synthesis of Tetratriazole Host FIG. 18. Examples of Compounds Used in Studies with Motor1 and Motor2 of Present Disclosure.

Ethanesulfonate Host a (FIG. 7).

Sodium 2,2'-(1,4-phenylenebis(oxy))diethanesulfonate (1.81 g, 0.23 mmol) was added into a solution of methyl tetramer (0.64 g, 0.77 mmol) in TFA (2 mL). The mixture was stirred and heated at 70° C. for 4 h. The solvent was removed with under reduced pressure and the solid was further dried under high vacuum. The solid was washed with the mixture of water and acetone (1:2, v/v, 30 mL) twice and then dissolved in water and adjusted to pH=7 by adding 1 M aqueous NaOH. The solvent was removed under reduced pressure and then the solid was further dried under high vacuum to yield product a as a white solid (0.72 g, 61%). $^1$H NMR (400 MHz, D$_2$O): 6.94 (s, 4H), 5.67 (d, J=15.5, 2H), 5.56 (d, J=16.0, 4H), 5.44 (d, J=7.6, 2H), 5.38 (d, J=7.6, 2H), 5.35 (d, J=16.3, 4H) 4.45-4.25 (m, 8H), 4.24 (d, J=16.0, 4H), 4.21 (d, J=16.3, 4H) 4.10 (d, J=15.5, 2H), 3.55-3.40 (m, 4H), 3.35-3.20 (m, 4H), 1.79 (s, 6H), 1.75 (s, 6H). $^{13}$C NMR (125 MHz, D$_2$O, 1,4-dioxane as internal reference): δ 156.4, 155.9, 149.6, 127.8, 114.4, 78.4, 77.1, 70.9, 70.8, 65.2, 52.2, 50.1, 48.0, 34.8, 15.6, 14.6.

Butanesulfonate Host b (FIG. 7).

Sodium 4,4'-(1,4-phenylenebis(oxy))bis(butane-1-sulfonate) (6.50 g, 15.4 mmol) was added into a solution of methyl tetramer (3.00 g, 3.84 mmol) in TFA (30 mL). The mixture was stirred and heated at 70° C. for 4 h. The solvent was removed under reduced pressure and the solid was further dried under high vacuum. The solid was washed twice with the mixture of water and acetone (1:2, v/v, 300 mL) and then dissolved in water and adjusted to pH=7 by adding 1 M aqueous NaOH. The solvent was removed under reduced pressure and then the solid was further dried under high vacuum to yield product b as a white solid (2.33 g, 40%). $^1$H NMR (400 MHz, D$_2$O): 7.01 (s, 4H), 5.62 (d, J=15.2, 2H), 5.51 (d, J=16.0, 4H), 5.45 (d, J=8.9, 2H), 5.35 (d, J=8.9, 2H), 5.24 (d, J=16.0, 4H), 4.30 (d, J=16.0, 4H), 4.25 (d, J=16.0, 4H), 4.04 (d, J=15.2, 2H), 3.90-3.75 (m, 8H), 2.90-2.75 (m, 4H), 2.70-2.55 (m, 4H), 1.79 (s, 12H), 1.79-1.30 (m, 16H).

Figure 8:
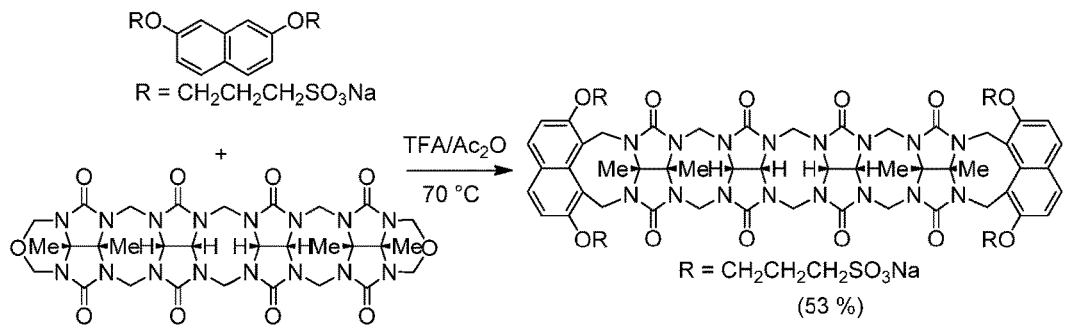

Naphthalene Propanesulfonate Host (FIG. 8).

Sodium 3,3'-(naphthalene-2,7-diylbis(oxy))dipropane-1-sulfonate (229 mg, 0.152 mmol) was added into a solution of methyl tetramer (100 mg, 0.128 mmol) in a mixture of TFA/Ac$_2$O (1:1, 2 mL). The mixture was stirred and heated at 70° C. for 3 h and then was poured into acetone (30 mL).

The solid was collected with filtration. The crude solid was dissolved in H$_2$O (10 mL), and then precipitated by the addition of acetone (30 mL). The product was then collected by filtration and then recrystallized from water and acetone (1:1, v/v, 5 mL). The purified product was obtained as a pale beige solid after drying under high vacuum (112 mg, 53%). $^1$H NMR (400 MHz, D$_2$O): 6.95 (d, J=8.9, 4H), 6.48 (d, J=8.9, 4H), 5.60 (d, J=16.3, 4H), 5.58 (d, J=15.4, 6H), 5.30 (d, J=9.0, 2H), 5.20 (d, J=9.0, 2H), 4.72 (d, J=16.3, 4H), 4.16 (d, J=15.4, 4H), 4.00-3.85 (m, 8H), 3.30-3.05 (m, 8H), 2.35-2.10 (m, 8H), 1.76 (s, 12H). $^{13}$C NMR (125 MHz, D$_2$O, 1,4-dioxane as internal reference): δ 156.4, 156.1, 155.0, 131.6, 127.3, 116.3, 112.6, 76.8, 75.4, 70.8, 68.1, 52.2, 48.0, 47.9, 33.1, 29.7, 24.4, 16.6, 15.2, (only 19 out of the 20 expected resonances were observed).

Figure 9:
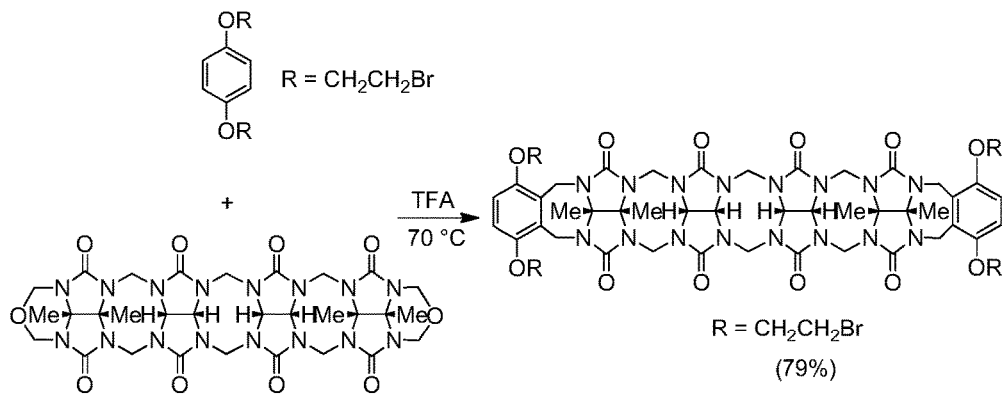

Tetrabromo Host (FIG. 9).

1,4-bis(2-bromoethoxy)benzene (1.70 g, 5.21 mmol) and methyl tetramer (1.20 g, 1.53 mmol) were mixed in a round bottom flask. TFA (12 mL) was added, and the mixture was stirred at 70° C. for 3 h. The reaction mixture was poured into MeOH (100 mL), and the solid was collected by filtration. The crude product was stirred with water (150 mL) and then acetone (150 mL) at RT and the solid was isolated by filtration. Drying at high vacuum gave the product as a white powder (1.71 g, 79%). M.p. 283-285° C. IR (ATR, cm$^{-1}$): 3000br, 1704m, 1456m, 1311m, 1225s, 1177s, 1080s, 966m, 922m, 818m, 794s, 754m, 666m. $^1$H NMR (400 MHz, DMSO): 6.91 (s, 4H), 5.59 (d, J=14.4, 2H), 5.51 (d, J=15.2, 4H), 5.38 (d, J=9.0, 2H), 5.30-5.25 (m, 6H), 4.50-4.40 (m, 4H), 4.25-4.20 (m, 10H), 4.06 (d, J=15.2, 4H), 3.90-3.80 (m, 8H), 1.69 (s, 6H), 1.66 (s, 6H). $^{13}$C NMR (125 MHz, DMSO, 1,4-dioxane as internal reference): δ 156.0, 154.6, 151.0, 129.5, 116.7, 78.0, 76.8, 71.5, 71.4, 71.0, 53.6, 48.9, 35.2, 33.5, 17.2, 16.3.

Figure 10:
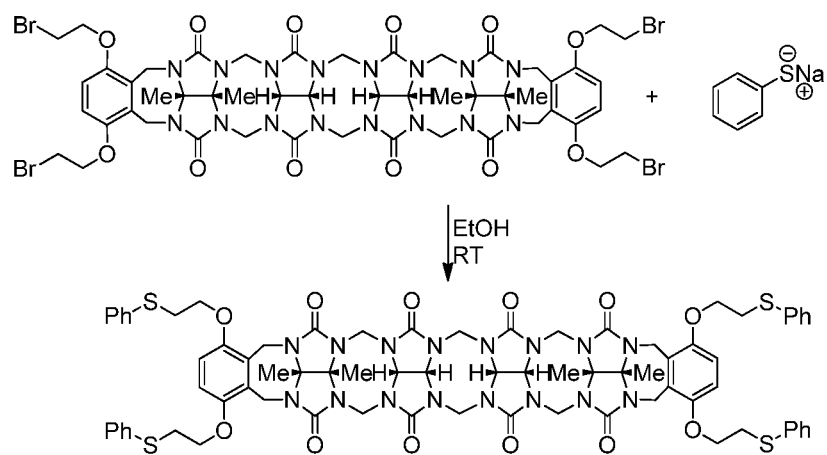

Tetrathiophenyl Host (FIG. 10).

Sodium benzenethiolate (48 mg, 0.36 mmol) was dissolved in EtOH (2 mL). Tetrabromohost (100 mg, 0.072 mmol) was added and the reaction mixture was stirred at RT for 12 h. The reaction mixture was centrifuged to collect the crude product. The solid was washed with EtOH (10 mL) and then H$_2$O (10 mL). A pale yellow solid was obtained after drying under high vacuum (63 mg, 58%). $^1$H NMR (400 MHz, DMSO): 7.45-7.05 (m, 20H), 6.68 (s, 4H), 5.62 (d, J=15.3, 2H), 5.51 (d, J=14.8, 4H), 5.39 (d, J=8.0, 2H), 5.27 (d, J=8.0, 2H), 5.24 (d, J=15.7, 4H), 4.25-4.10 (m, 4H), 4.10-3.85 (m, 14H), 3.45-3.30 (m, 8H), 1.69 (s, 6H), 1.63 (s, 6H).

Figure 11:
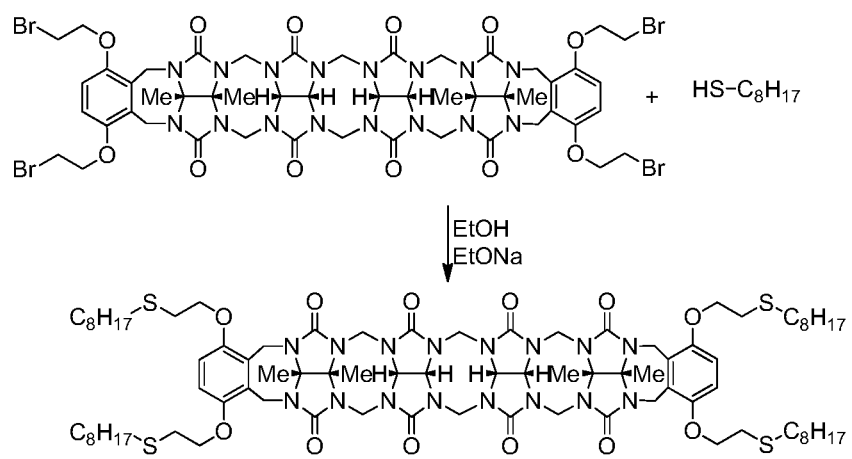

Tetra Octanethioether Host (FIG. 11).

Octane-1-thiol (53 mg, 0.36 mmol) was dissolved in EtOH (2 mL). Tetrabromohost (100 mg, 0.072 mmol) was added and the reaction mixture was stirred at RT for 3 h. The reaction mixture was centrifuged to collect crude solid. The solid was washed with EtOH (10 mL) and then H$_2$O (10 mL). A white solid was obtained after drying under high vacuum (103 mg, 72%). $^1$H NMR (400 MHz, DMSO): 6.82 (s, 4H), 5.59 (d, J=12.2, 2H), 5.48 (d, J=14.8, 2H), 5.35 (d, J=8.6, 2H), 5.24 (d, J=8.6, 2H), 5.24 (d, J=16.4, 4H), 4.25-4.20 (m, 4H), 4.08 (d, J=16.4, 4H), 4.04 (d, J=14.8, 4H), 4.10-4.00 (m, 4H), 3.99 (d, J=12.2, 2H), 2.88 (t, J=5.6, 8H), 2.63 (t, J=7.2, 8H), 1.66 (s, 6H), 1.62 (s, 6H), 1.56 (m, 8H), 1.40-1.15 (m, 40H), 0.83 (t, J=7.2, 12H).

Figure 12:
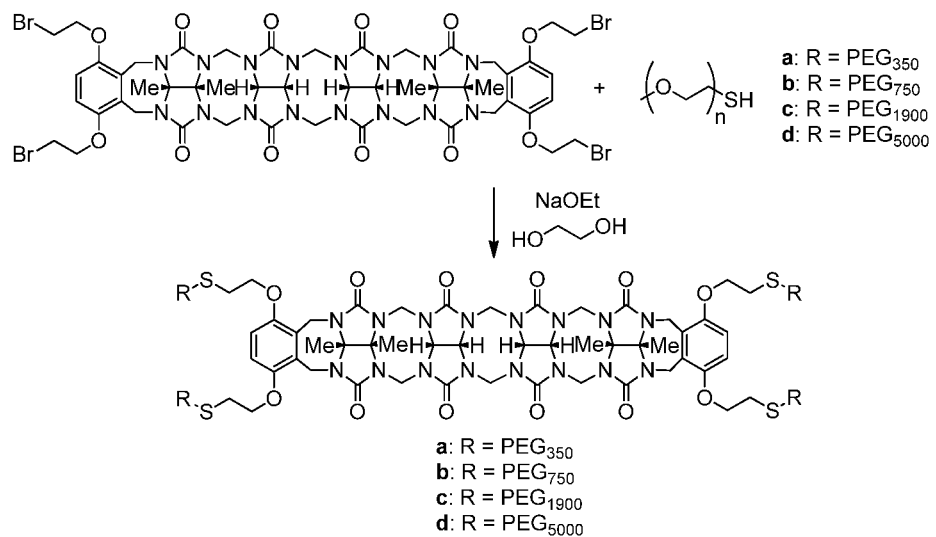

PEG 350 Host (FIG. 12).

PEG 350 (176 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 50° C. for 12 h. The reaction mixture was centrifuged to remove insoluble material and the clear solution was concentrated and poured into diethyl ether (10 mL). The white precipitate was collected by centrifugation. A dark yellow gel was obtained after drying under high vacuum (150 mg, 82%). $^1$H NMR (400 MHz, D$_2$O): 6.64 (s, 4H), 5.64 (d, J=16.0, 4H), 5.60-5.35 (m, 8H), 5.34 (d, J=8.4, 2H), 4.35 (d, J=16.0, 4H), 4.20-4.10 (m, 12H), 4.05, (d, J=12.3, 2H), 3.95-3.55 (m, 160H), 3.38 (s, 12H), 3.11 (t, J=6.0, 8H), 2.96 (t, J=6.0, 8H), 1.89 (s, 6H), 1.86 (s, 6H).

PEG 750 Host (FIG. 12).

PEG 750 (349 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. A pale yellow solid was obtained after drying under high vacuum (172 mg, 58%). $^1$H NMR (400 MHz, D$_2$O): 7.03 (s, 4H), 5.68 (d, J=16.2, 2H), 5.56 (d, J=15.6, 4H), 5.45-5.25 (m, 8H), 4.30-4.00 (m, 18H), 3.95-3.55 (m, 320H), 3.32 (s, 12H), 3.00-2.75 (m, 8H), 2.65 (t, J=6.0, 8H), 1.76 (s, 6H), 1.72 (s, 6H).

PEG 1900 Host (FIG. 12).

PEG 1900 (823 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (213 mg, 34%). $^1$H NMR (400 MHz, D$_2$O): 6.49 (s, 4H), 5.46 (d, J=16.4, 4H), 5.40-5.20 (m, 8H), 5.19 (d, J=8.4, 2H), 4.15 (d, J=16.0, 4H), 4.10-3.85 (m, 16H), 3.95-3.55 (m, 800H), 3.22 (s, 12H), 2.96 (t, J=6.2, 8H), 2.81 (t, J=6.2, 8H), 1.73 (s, 6H), 1.71 (s, 6H).

PEG 5000 Host (FIG. 12).

PEG 5000 (2.16 g, 0.43 mmol) and NaOEt (29 mg, 0.43 mmol) was dissolved in ethylene glycol (4 mL). Tetrabromo Host (100 mg, 0.072 mmol) was added and the reaction mixture was stirred and heated at 70° C. for 12 h. The reaction mixture was centrifuged to remove insoluble material and a mixture of CH$_2$Cl$_2$ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (351 mg, 23%). $^1$H NMR (400 MHz, D$_2$O): 7.05 (s, 4H), 5.71 (d, J=15.5, 2H), 5.62 (d, J=15.6, 4H), 5.60-5.25 (m, 8H), 4.30-4.00 (m, 18H), 3.95-3.55 (m, 1840H), 3.32 (s, 12H), 3.00-2.75 (m, 8H), 2.66 (t, J=6.0, 8H), 1.76 (s, 6H), 1.74 (s, 6H).

Figure 13:
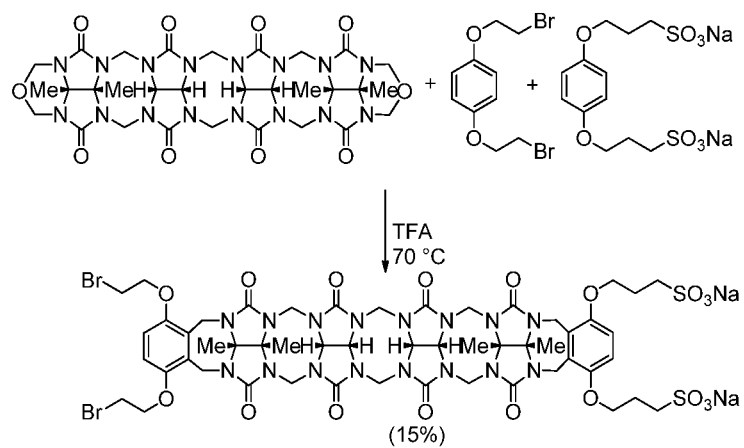

Dibromo Dipropanesulfonate Host (FIG. 13).

1,4-bis(2-bromoethoxy)benzene (250 mg, 0.768 mmol) and sodium 3,3'-(1,4-phenylenebis(oxy))bis(propane-1-sulfonate) (102 mg, 0.256 mmol) were added into a solution of methyl tetramer (200 mg, 0.256 mmol) in TFA (2.5 mL). The mixture was stirred and heated at 70° C. for 3 h and then was poured into acetone (150 mL). The solid was collected by filtration. The crude solid was stirred with water (30 mL×3) at RT for 4 hr. The filtrate was collected and the solvent was removed under reduced pressure. The product was purified by recrystallization from H$_2$O and MeOH (1:1, 15 mL). The product was obtained as a white solid after drying under high vacuum (112 mg, 53%). $^1$H NMR (400 MHz, D$_2$O): 6.97 (s, 2H), 6.72 (s, 2H), 5.62 (d, J=15.9, 2H), 5.60 (d, J=15.9, 2H), 5.53 (d, J=16.4, 2H), 5.45 (d, J=5.8, 2H), 5.43 (d, J=15.9, 2H), 5.40 (d, J=5.0, 2H), 5.21 (d, J=10.8, 2H), 4.27 (d, J=16.4, 2H), 4.25-4.20 (m, 8H), 4.15-4.05 (m, 8H), 3.95-3.75 (m, 4H), 3.45-3.35 (m, 2H), 3.25-3.20 (m, 2H), 3.14 (t, J=7.7, 4H), 2.35-2.15 (m, 4H), 1.87 (s, 3H), 1.81 (s, 3H), 1.67 (s, 3H), 1.66 (s, 3H).

Figure 14:
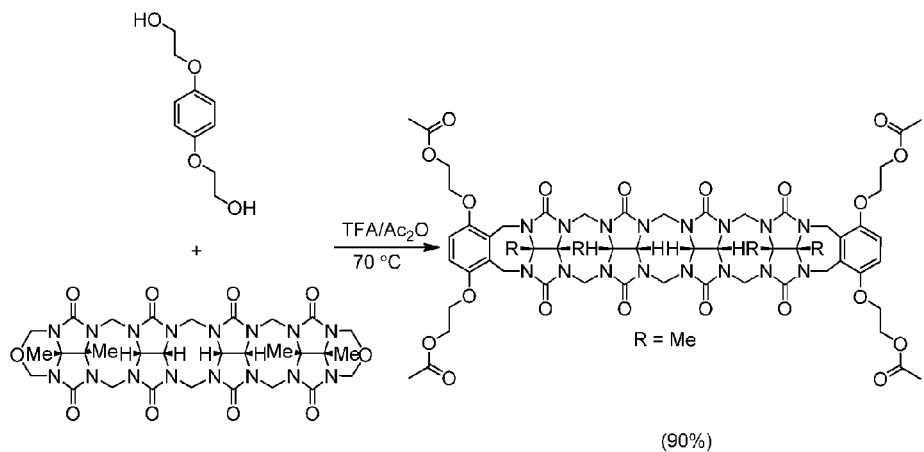

Tetra Ester Host (FIG. 14).

2,2'-(1,4-phenylenebis(oxy))diethanol (1.02 g, 5.12 mmol) and methyl tetramer (1.00 g, 1.28 mmol) were mixed as solid and then dissolved in a mixture of TFA and Ac$_2$O (1:1, 10 mL). The mixture was stirred at 70° C. for 3.5 h and then was poured into MeOH (150 mL). The solid was collected by filtration and was washed with acetone (100 mL) and water (100 mL). After drying under high vacuum, the product was obtained as a white powder (1.51 g, 90%). M.p.>300° C. IR (ATR, cm$^{-1}$): 3000w, 1711s, 1456s, 1313m, 1225s, 1178s, 1076s. $^1$H NMR (400 MHz, DMSO): 6.85 (s, 4H), 5.58 (d, J=16.3, 2H), 5.48 (d, J=15.6, 4H), 5.37 (d, J=9.0, 2H), 5.27 (d, J=9.0, 2H), 5.23 (d, J=16.0, 4H), 4.45-4.30 (m, 4H), 4.30-4.05 (m, 14H), 3.50-3.45 (m, 8H), 2.06 (s, 12H), 1.76 (s, 12H).

Figure 15:
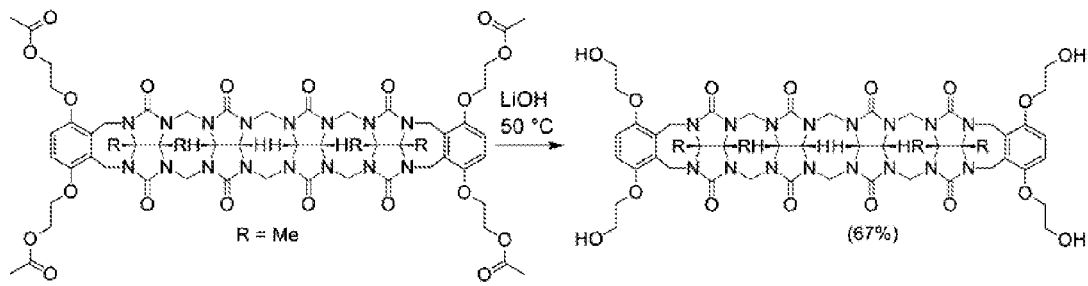

Tetra Hydroxy Host (FIG. 15).

Tetra Ester Host (0.400 g, 0.305 mmol) was added into an aqueous solution of LiOH (2.5 M, 7.5 mL). The mixture was stirred at 50° C. for 0.5 h and then the solid was collected by filtration. The solid was wash with 0.1 M HCl to neutral and then stirred with EtOH (30 mL), and water (30 mL). After drying under high vacuum, a white solid was obtained (0.234 g, 67%). $^1$H NMR (400 MHz, D$_2$O): 6.95 (s, 4H), 5.62 (d, J=15.3, 2H), 5.52 (d, J=15.7, 4H), 5.43 (d, J=8.0, 2H), 5.20 (d, J=8.0, 2H), 4.72 (d, J=16.2, 4H), 4.28 (d, J=15.7, 4H), 4.23 (d, J=16.2, 4H), 4.19 (d, J=15.3, 2H), 3.85-3.50 (m, 8H), 3.45-2.85 (m, 8H), 1.76 (s, 12H).

Figure 16:
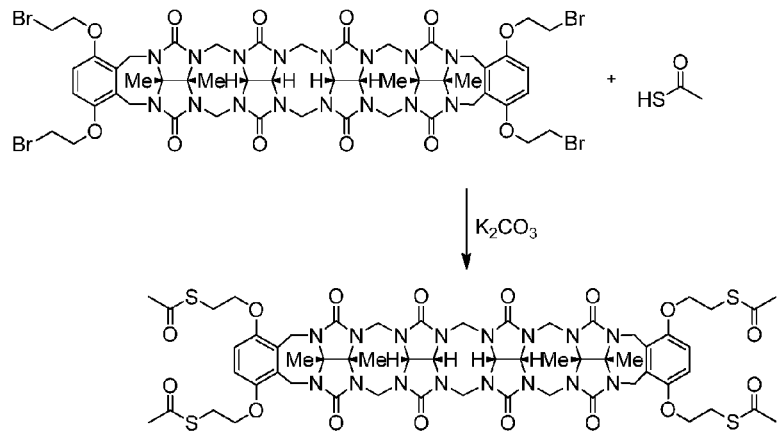

Tetrathioacetate Host (FIG. 16).

K$_2$CO$_3$ (99 mg, 0.43 mmol) and Ethanethioic S-acid (55 mg, 0.43 mmol) was added into DMF (2 mL) and was stirred at RT for 15 min under N$_2$. Tetrabromo Host (100 mg, 0.072 mmol) was added as a solid. The mixture was stirred at 50° C. for 12 h and then was poured into H$_2$O (6 mL). The solid was collected by filtration and was then washed with H$_2$O (5 mL) and acetone (5 mL). A beige solid was obtained after drying under high vacuum (73 mg, 74%). $^1$H NMR (400 MHz, DMSO): 6.85 (s, 4H), 5.58 (d, J=16.3, 2H), 5.48 (d, J=15.6, 4H), 5.38 (d, J=9.0, 2H), 5.27 (d, J=9.0, 2H), 5.22 (d, J=16.0, 4H), 4.25-4.10 (m, 4H), 4.15-3.90 (m, 14H), 3.35-3.25 (m, 8H), 2.37 (s, 12H), 1.68 (s, 6H), 1.64 (s, 6H).

Figure 17:
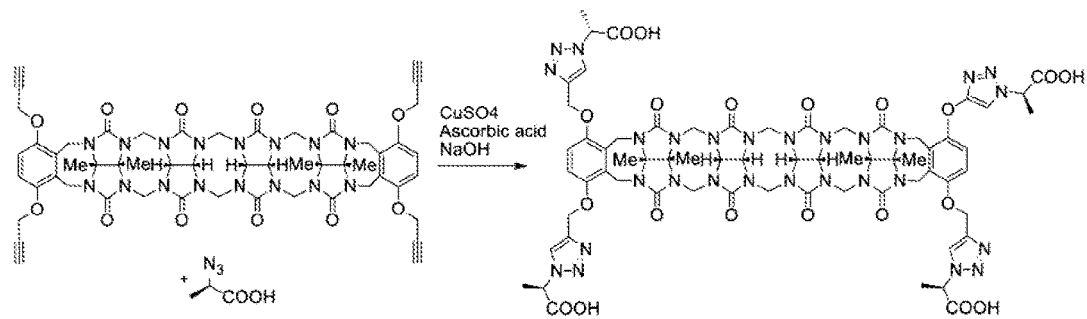
Figure 18:
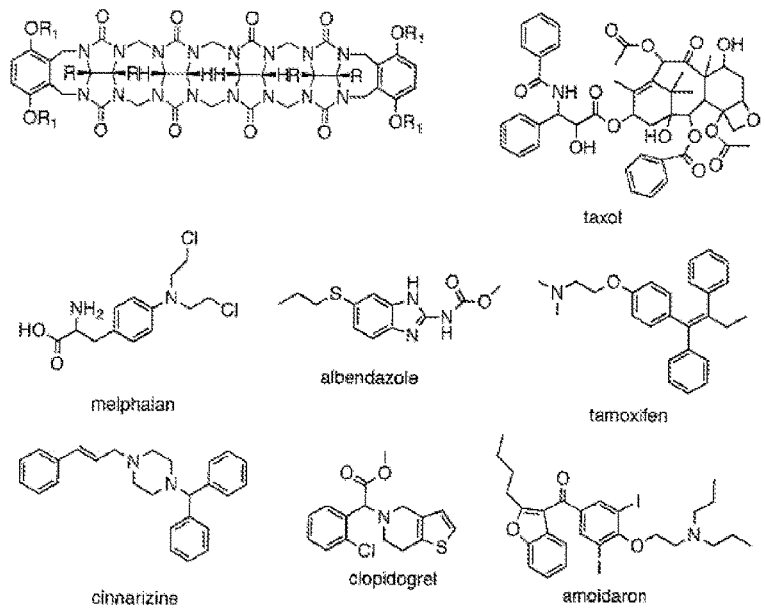
Figure 19:
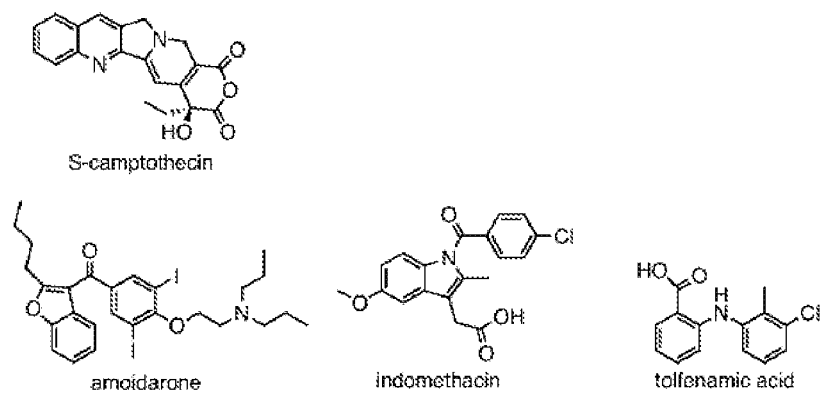
FIG. 19. Further Examples of Compounds Used in Studies with Motor1 and Motor2 of Present Disclosure FIG. 20. A view of the x-ray crystal structure of Motor1 showing the anisotropic atomic displacement ellipsoids for the non-hydrogen atoms at the 30% probability level. Hydrogen atoms are displayed with an arbitrarily small radius.

Tetra Triazole Host (FIG. 17).

Ascorbic acid (7 mg, 0.04 mmol), NaOH (2 mg, 0.04 mmol) and CuSO$_4$ (2 mg, 0.01 mmol) was mixed and then dissolved in a mixture of H$_2$O and EtOH (1 mL, 1:1). Alkyne Host (26 mg, 0.024 mmol) and (R)-2-azidopropanoic acid (22 mg, 0.19 mmol) was added as solid. The mixture was heated with microwave at 80° C. for 30 min, and then solvent was removed under reduced pressure. The crude solid was washed with MeOH (2 mL). A yellowish solid was obtained after drying under high vacuum (15 mg, 40%). $^1$H NMR (400 MHz, DMSO): 8.44 (s, 2H), 8.34 (s, 2H), 6.97 (m, 4H), 5.65-5.45 (m, 12H), 5.39 (d, J=8.4, 2H), 5.25-5.05 (m, 18H), 4.25-4.00 (m, 4H), 1.72 (m, 12H), 1.69 (s, 6H), 1.64 (s, 6H).

Example 3

Figure 20:
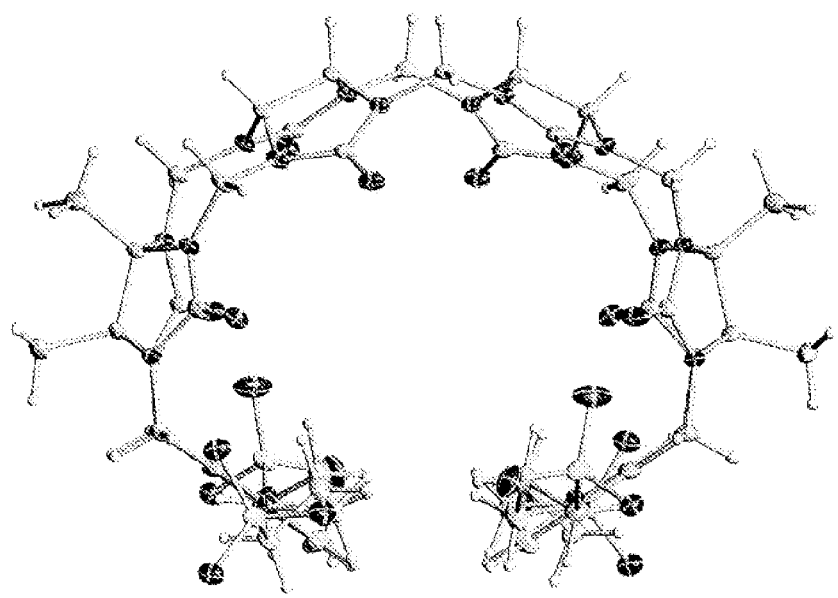
Figure 21:
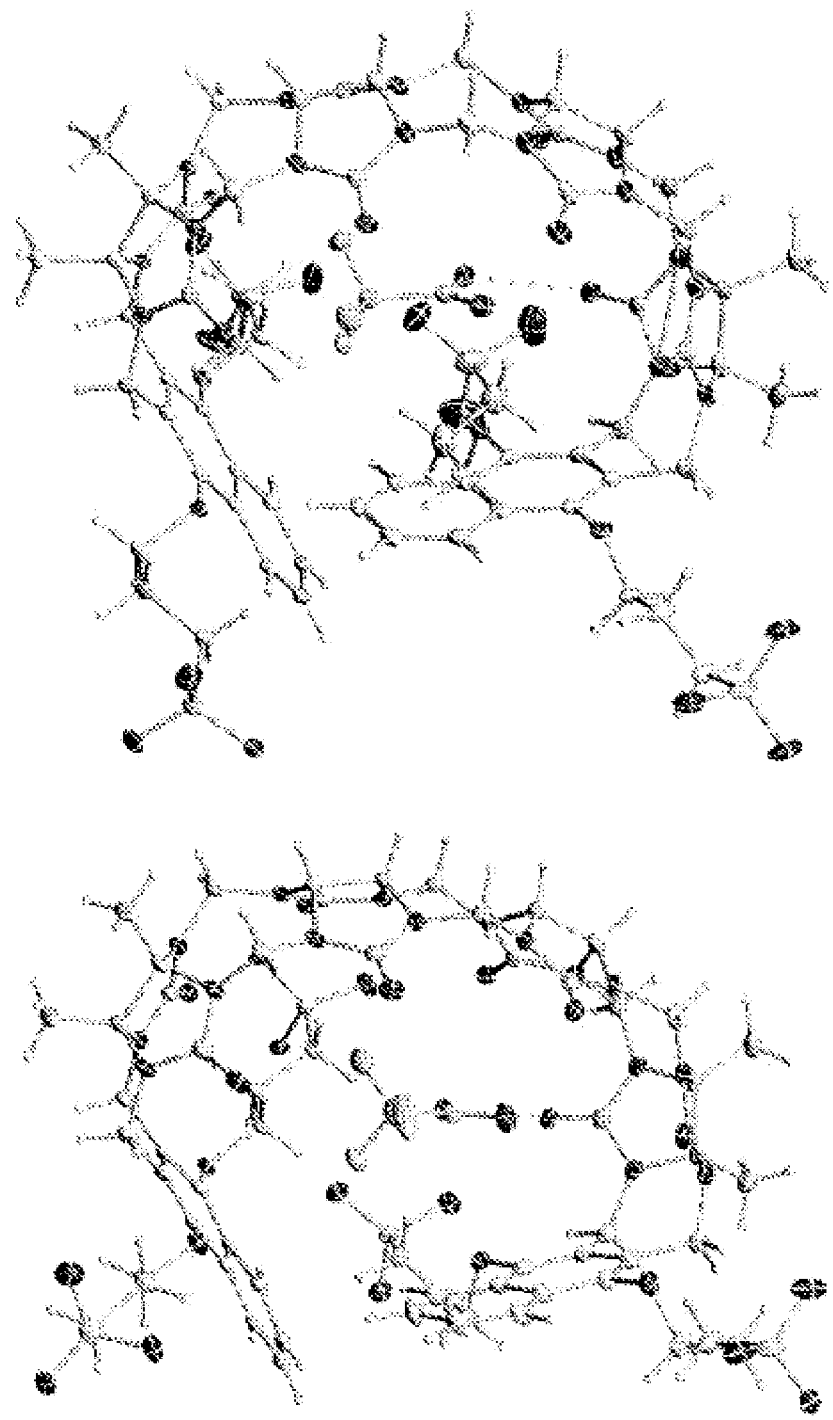
FIG. 21. A view two symmetrically independent guest-host complexes in the x-ray crystal structure of Motor2 showing the anisotropic atomic displacement ellipsoids for the non-hydrogen atoms at the 30% probability level. Hydrogen atoms are displayed with an arbitrarily small radius.
Figure 22:
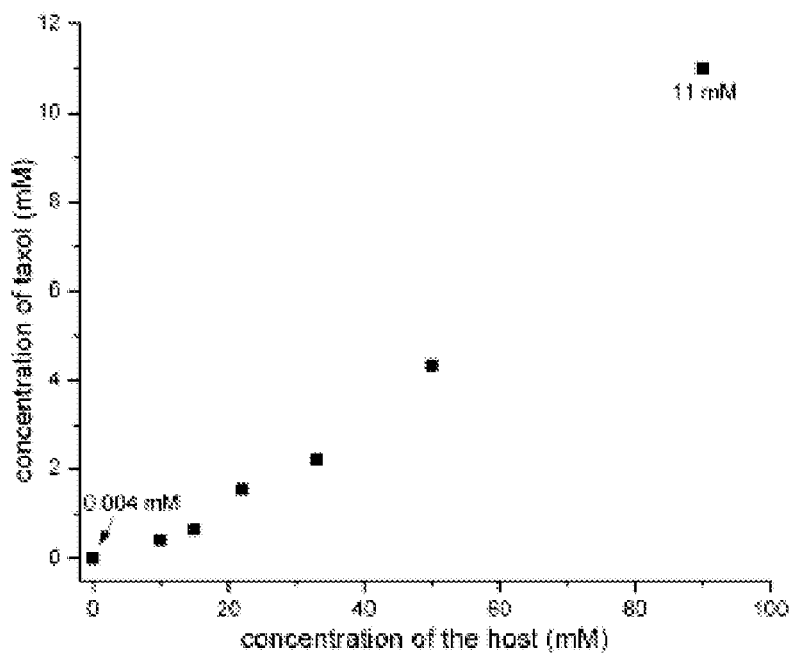
FIG. 22. An example of a phase diagram of mixtures of Taxol (anticancer agent) and Motor1 in 20 mM sodium phosphate buffer (pH=7.4). Solubility enhancement=2750-fold.
Figure 23:
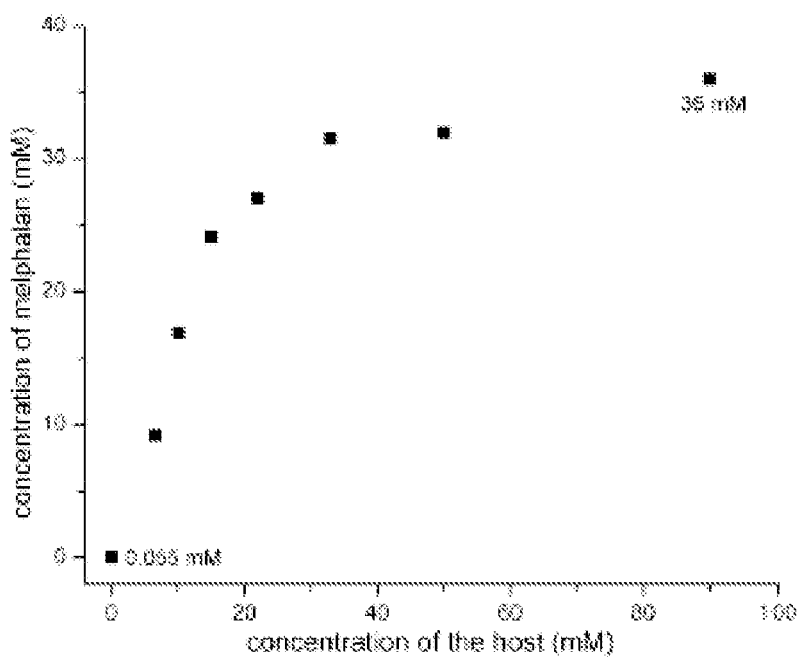
FIG. 23. An example of a phase diagram of Melphalan (anti-cancer agent) and Motor1 in 20 mM sodium phosphate buffer (pH=7.4). Solubility enhancement=655-fold.
Figure 24:
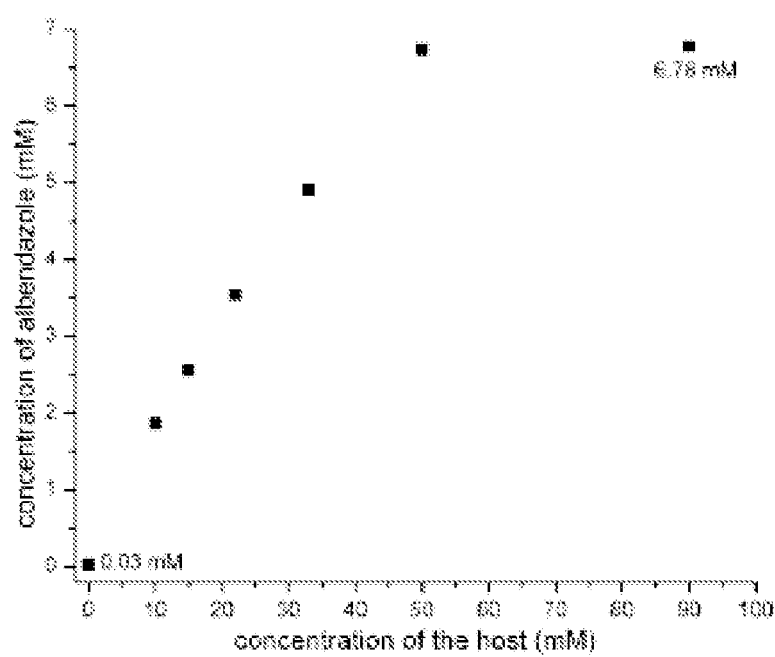
FIG. 24. An example of a phase diagram of Albendazole (various uses) and Motor1 in 20 mM sodium phosphate buffer (pH=7.4). Solubility enhancement=226-fold.
Figure 25:
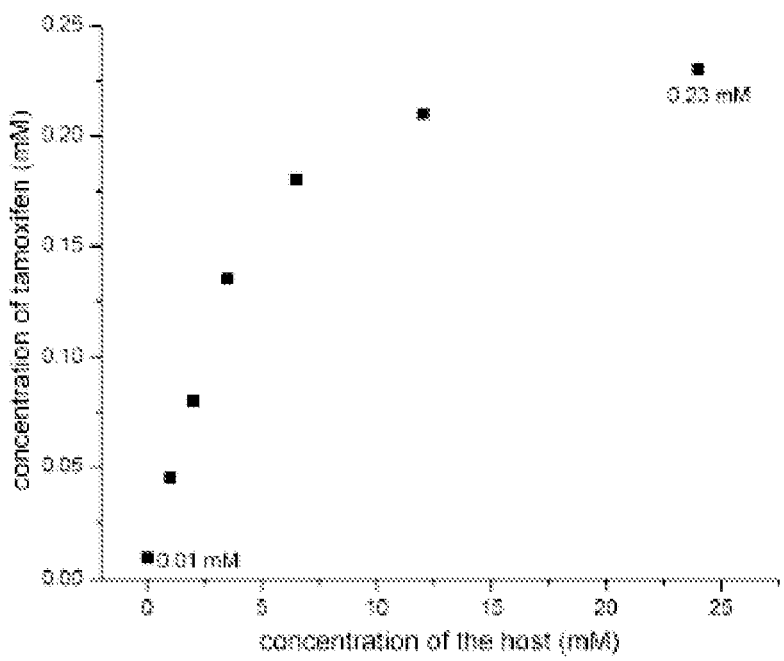
FIG. 25. An example of a phase diagram of Tamoxifen (anti-cancer) and Motor1 in 20 mM sodium phosphate buffer (pH=7.4). Solubility enhancement=23-fold.
Figure 26:
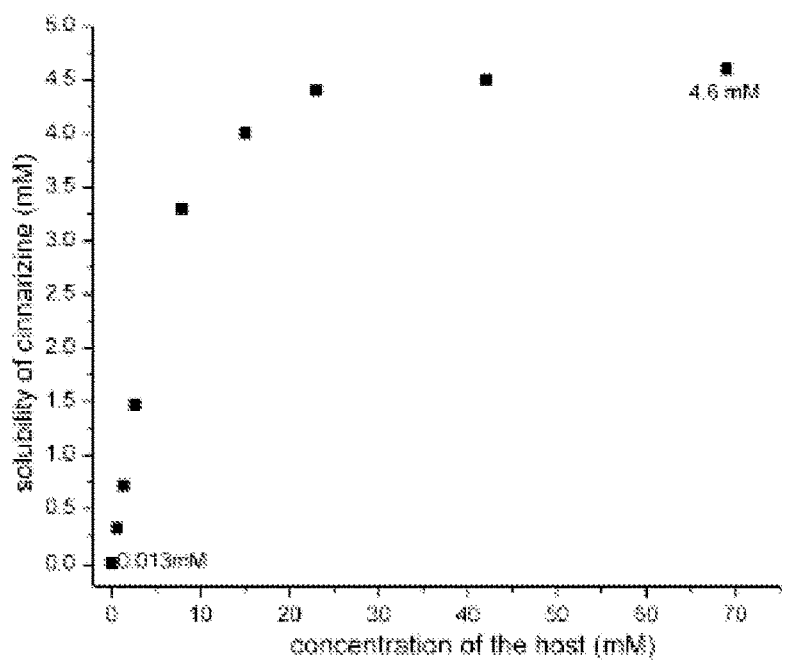
FIG. 26. An example of a phase diagram of Cinnarizine (anti-histamine) and Motor1 in 20 mM sodium phosphate buffer (pH=7.4). Solubility enhancement=354-fold.
Figure 27:
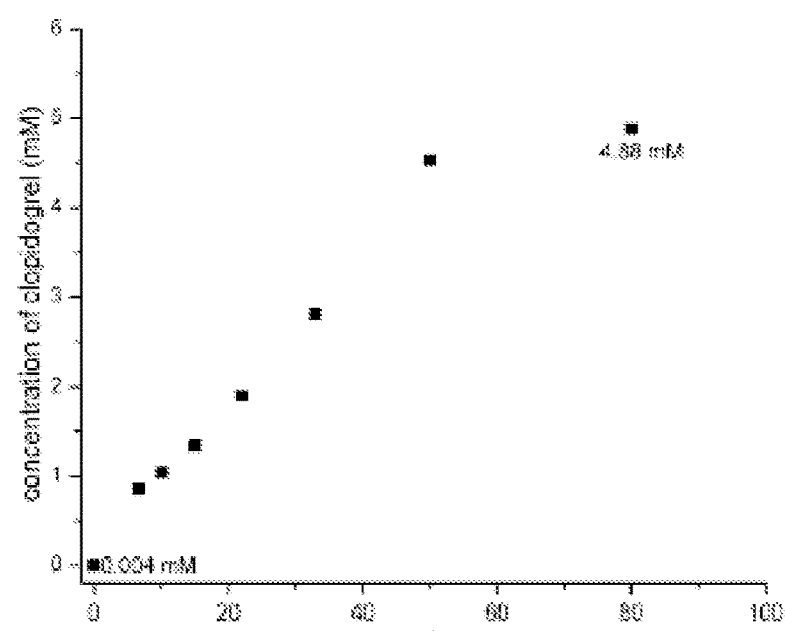
FIG. 27. An example of a phase diagram of Clopidogrel (clot inhibitor) and Motor1 in 20 mM sodium phosphate buffer (pH=7.4). Solubility enhancement=1220-fold.
Figure 28:
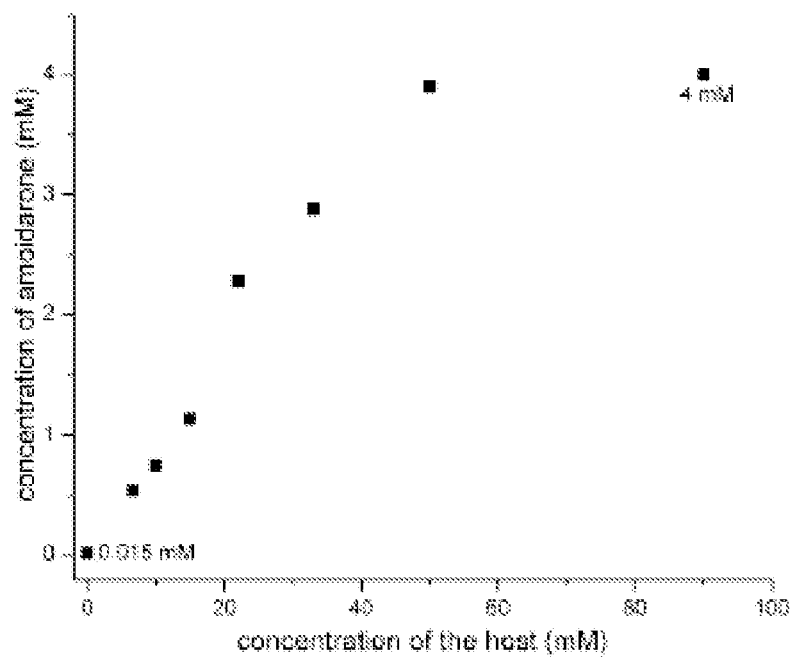
FIG. 28. An example of a phase diagram of amiodarone (anti-arrythmic agent) and Motor1 in 20 mM sodium phosphate buffer (pH=7.4). Solubility enhancement=267-fold.
Figure 29:
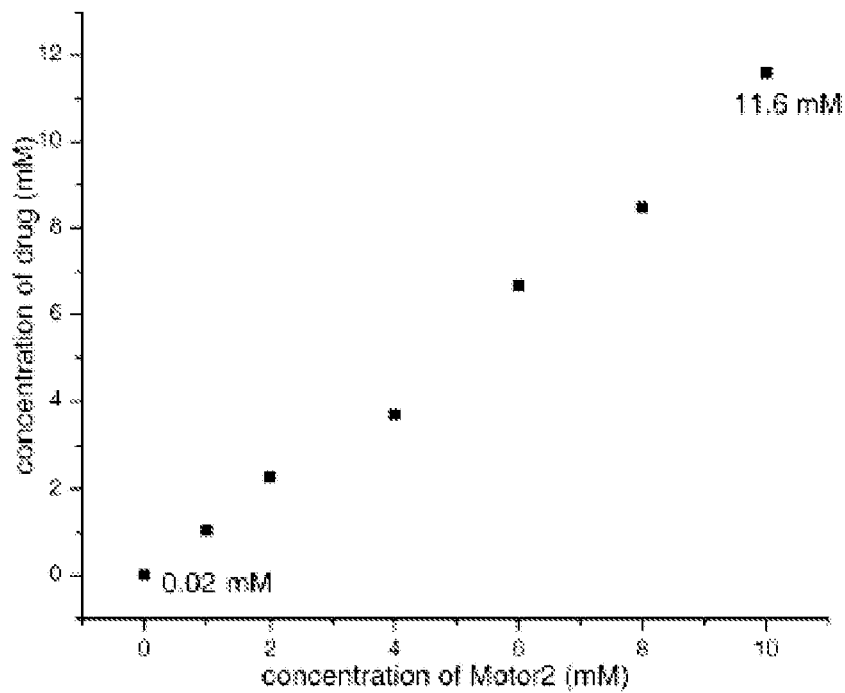
FIG. 29. An example of a phase diagram of drug S-camptothecin solubilized with Motor2 in 20 mM sodium phosphate buffer (pH=7.4). Solubility enhancement=580-fold.
Figure 30:
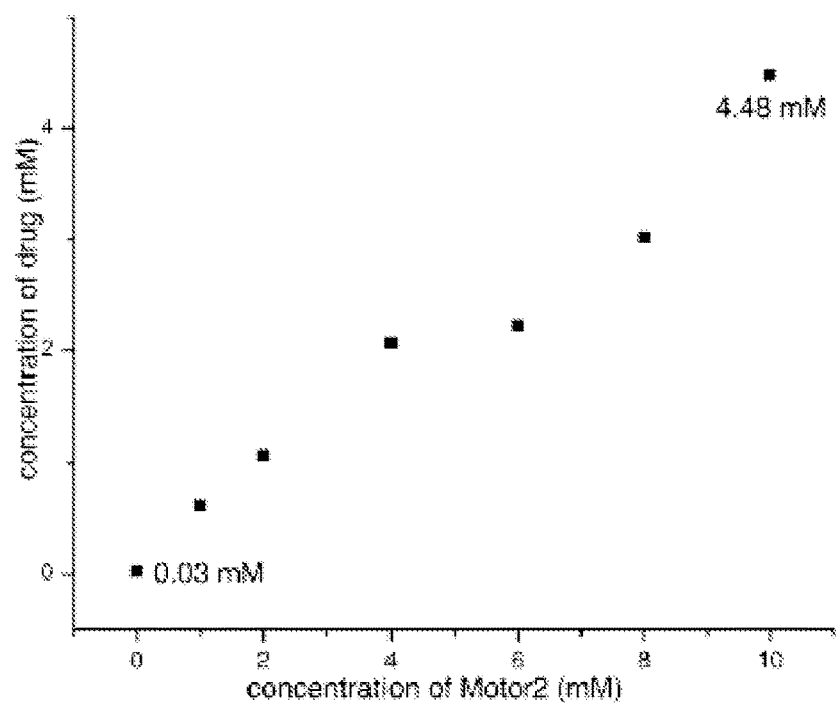
FIG. 30. An example of a phase diagram of drug albendazole solubilized with Motor2 in 20 mM sodium phosphate buffer (pH=7.4). Solubility enhancement=149-fold.
Figure 31:
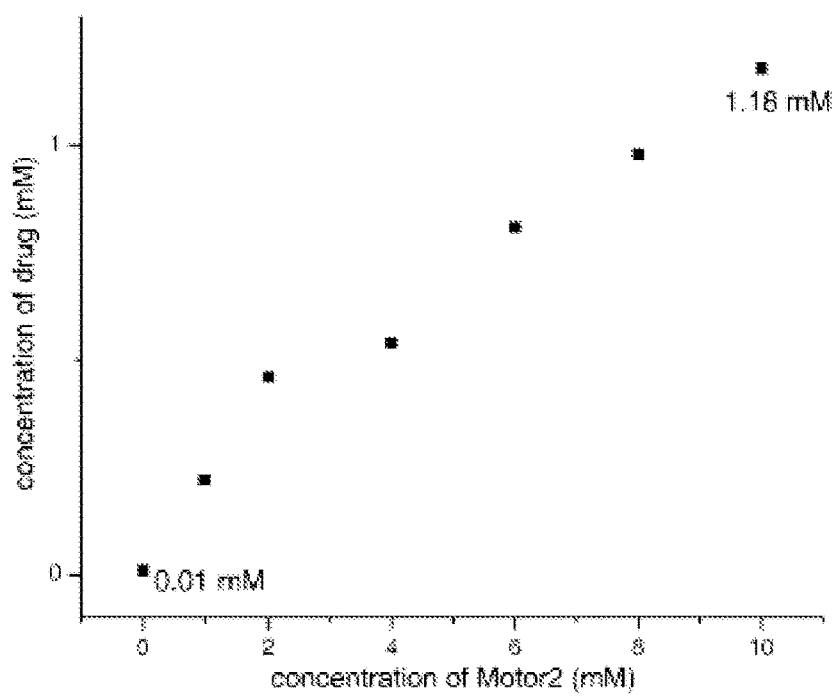
FIG. 31. An example of a phase diagram of drug tamoxifen solubilized with Motor2 in 20 mM sodium phosphate buffer (pH=7.4). Solubility enhancement=118-fold.
Figure 32:
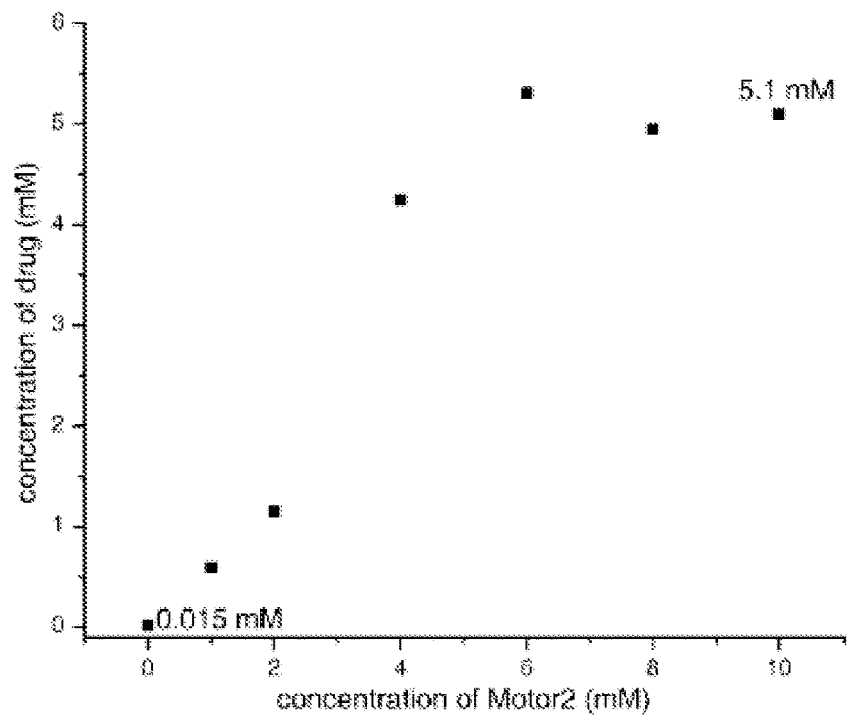
FIG. 32. An example of a phase diagram of drug amiodarone solubilized with Motor2 in 20 mM sodium phosphate buffer (pH=7.4). Solubility enhancement=340-fold.
Figure 33:
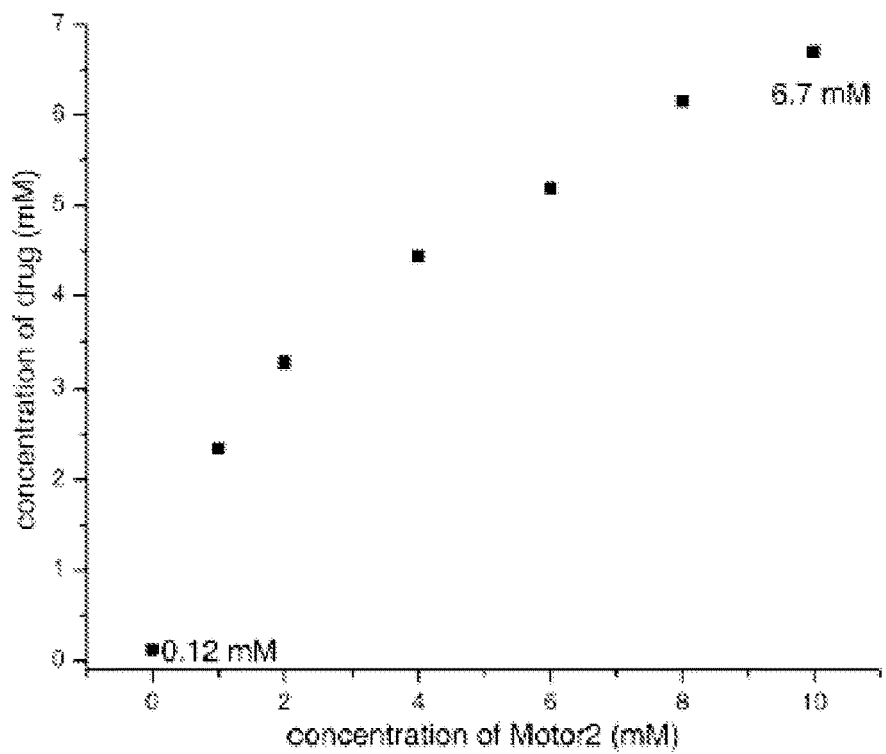
FIG. 33. An example of a phase diagram of drug indomethacin solubilized with Motor2 in 20 mM sodium phosphate buffer (pH=7.4). Solubility enhancement=56-fold.
Figure 34:
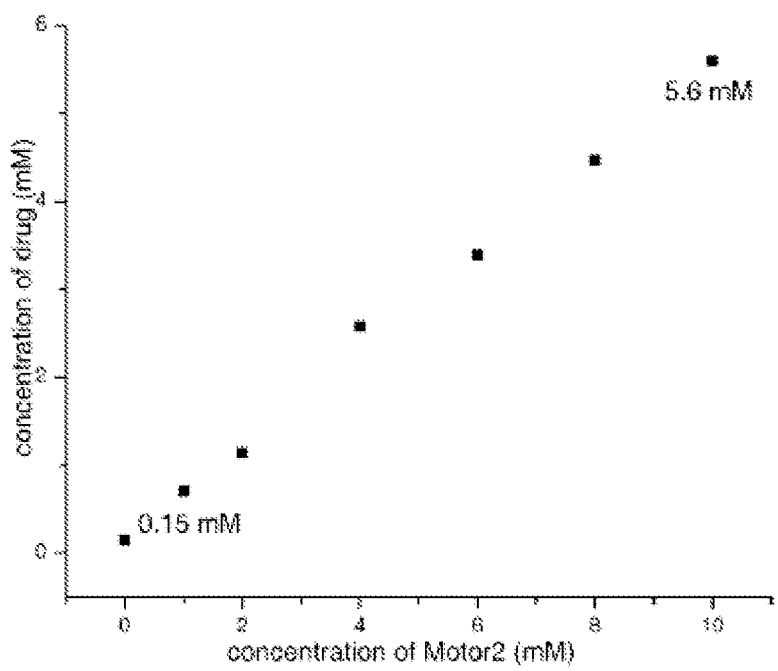
FIG. 34. An example of a phase diagram of drug tolfenamic acid solubilized with Motor2 in 20 mM sodium phosphate buffer (pH=7.4). Solubility enhancement=37-fold.
Figure 35:
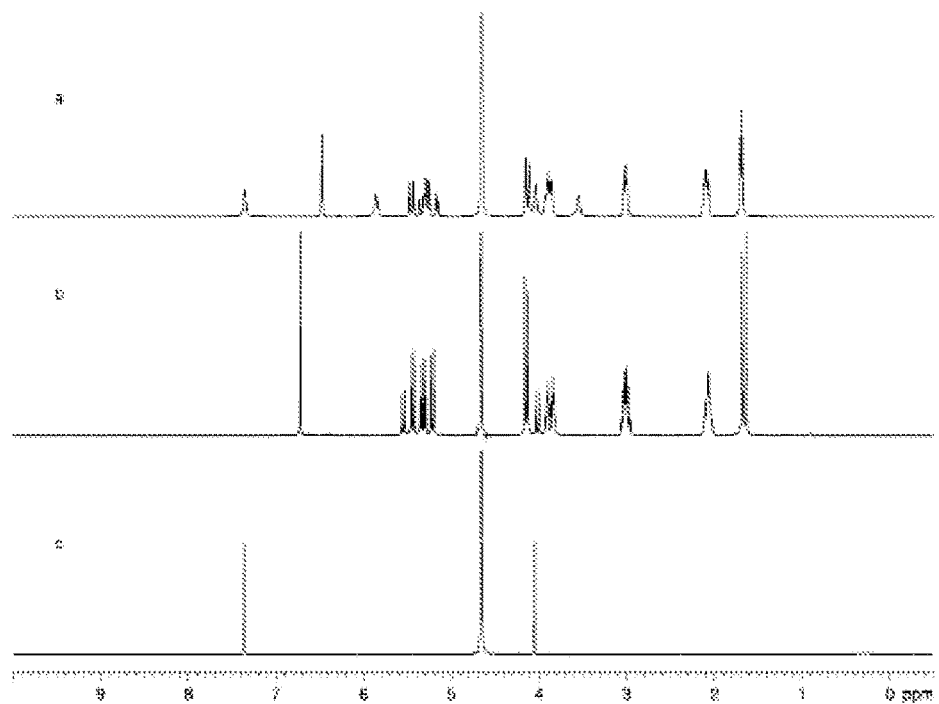
FIG. 35. An example of a $^1$H NMR recorded for a) Motor1 and 2 eq. p-xylenediamine; b) Motor1; and c) p-xylenediamine in 20 mM $Na_2DPO_4$ (pD 7.4).
Figure 36:
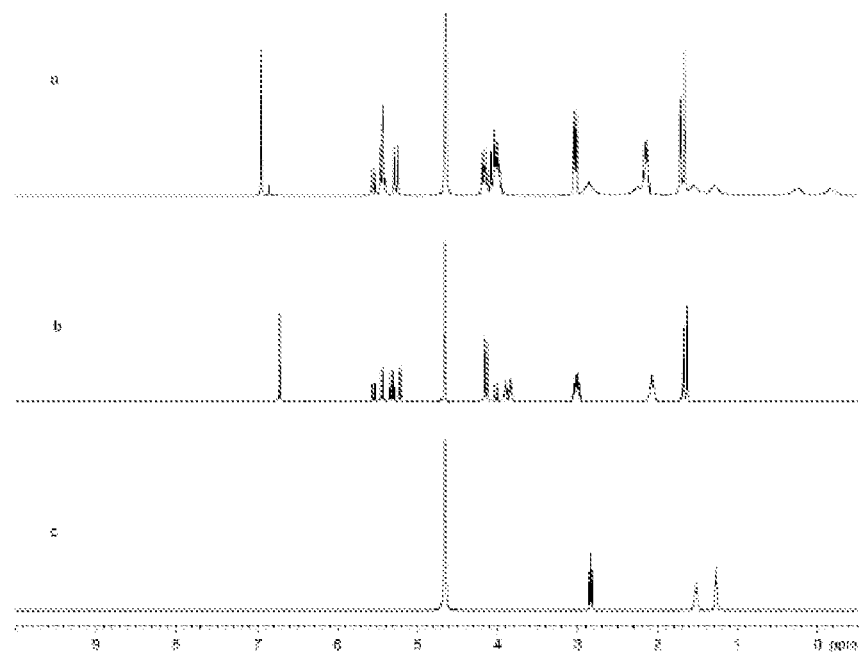
FIG. 36. An example of a $^1$H NMR recorded for a) Motor1 and 2 eq. hexanediamine; b) Motor1; and c) hexanediamine in 20 mM $Na_2DPO_4$ (pD 7.4).
Figure 37:
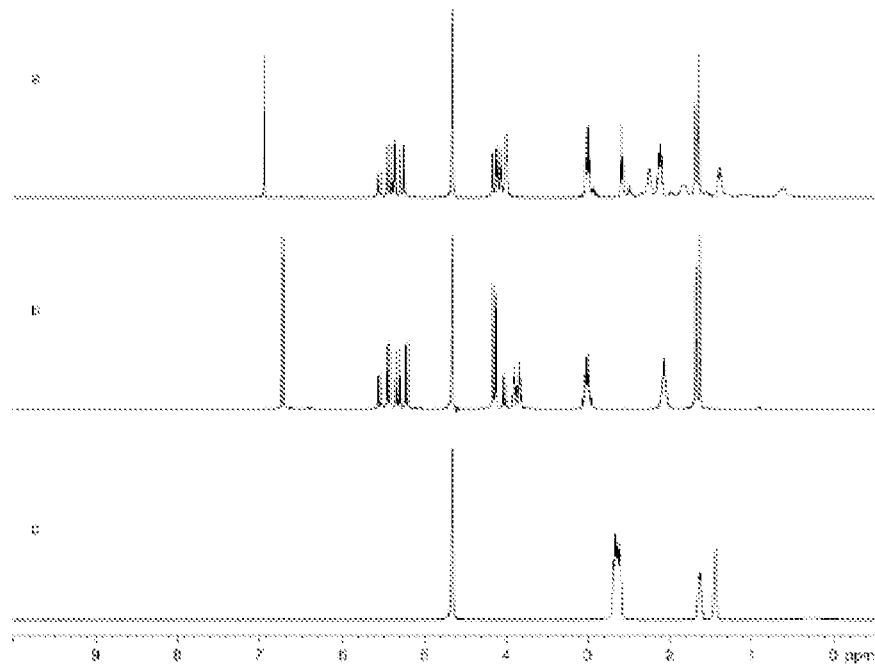
FIG. 37. An example of a $^1$H NMR recorded for a) Motor1 and 2 eq. spermine; b) Motor1; and c) spermine in 20 mM $Na_2DPO_4$ (pD 7.4).

X-ray crystallographic structures for examples of compounds of the present invention are show in FIGS. 20-21.

The crystals were grown by dissolving the compounds in mixtures of TFA and water, filtering into a clean 4 mL screw capped vial and allowing them to stand in a glass desiccation chamber at room temperature until crystals formed.

(FIG. 20) A colorless prism of Na$_4$(C$_{54}$H$_{64}$N$_{16}$O$_{24}$S$_4$).5.32CF$_3$COOH·14.29H$_2$O, approximate dimensions 0.26×0.365×0.365 mm$^3$, was used for the X-ray crystallographic analysis. The X-ray intensity data were measured at 150(2) K on a three-circle diffractometer system equipped with Bruker Smart Apex II CCD area detector using a graphite monochromator and a MoKα. fine-focus sealed tube (λ=0.71073 Å). The detector was placed at a distance of 6.000 cm from the crystal. A total of 3180 frames were collected with a scan width of −0.30° in CD and an exposure time of 40 sec/frame using Apex2 (Bruker, 2005). The total data collection time was 40.6 hours. The frames were integrated with Apex2 software package using a narrow-frame integration algorithm. The integration of the data using a Monoclinic unit cell yielded a total of 53424 reflections to a maximum θ angle of 25.00°, of which 8787 were independent (completeness=99.9%, R$_{int}$=2.91%, R$_{sig}$=1.84%) and 8368 were greater than 2σ(I). The final cell dimensions of a=23.4856(10) Å, b=24.7081(11) Å, c=19.3126(8) Å, a.=90°, β=117.1930(10)°, γ=90°, V=9968.1(7) Å$^3$, are based upon the refinement of the XYZ-centroids of 33943 reflections with 2.3<θ<28.3° using Apex2. Analysis of the data showed 0% decay during data collection. Data were corrected for absorption effects with the Semiempirical from equivalents method using SADABS (Sheldrick, 1996). The minimum and maximum transmission coefficients were 0.840 and 0.936. The structure was solved and refined using the SHELXS-97 (Sheldrick, 1990) and SHELXL-97 (Sheldrick, 1997) software in the space group C2/c with Z=4 for the formula unit Na$_4$(C$_{54}$H$_{64}$N$_{16}$O$_{24}$S$_4$).5.32CF$_3$COOH·14.29H$_2$O. The final anisotropic full-matrix least-squares refinement on F$^2$ with 908 variables converged at R$_1$=8.55% for the observed data and wR$_2$=16.67% for all data. The goodness-of-fit was 1.000. The largest peak on the final difference map was 0.822 ē/Å$^3$ and the largest hole was −0.668 ē/Å$^3$. On the basis of the final model, the calculated density was 1.651 g/cm$^3$ and F(000), 5082 ē.

(FIG. 21) A colorless prism of Na$_4$RC$_2$HF$_3$O$_2$)@(C$_{62}$H$_{68}$N$_{16}$O$_{24}$S$_4$)}.~10(C$_2$HF$_3$O$_2$).~12.5H$_2$O, approximate dimensions 0.52×0.53×0.59 mm$^3$, was used for the X-ray crystallographic analysis. The X-ray intensity data were measured at 100(2) K on a three-circle diffractometer system equipped with Bruker Smart Apex II CCD area detector using a graphite monochromator and a MoKα fine-focus sealed tube (λ=0.71073 Å). The detector was placed at a distance of 6.0000 cm from the crystal. A total of 2480 frames were collected with a scan width of −0.299988° an exposure time of 30 sec/frame using Apex2 (Bruker, 2005). The total data collection time was 24.8 hours. The frames were integrated with Apex2 software package using a narrow-frame integration algorithm. The integration of the data using a Triclinic unit cell yielded a total of 119514 reflections to a maximum θ angle of 25.00°, of which 46074 were independent (completeness=99.6%, R$_{int}$=2.53%, R$_{sig}$=3.84%) and 35361 were greater than 2σ(I). The final cell dimensions of a=19.457(2) Å, b=23.652(2) Å, c=29.876(3) Å, a=80.7050(10)°, ~=87.9730(10)°, Y=75.3600(10)°, V=13127(2) Å$^3$, are based upon the refinement of the XYZ-centroids of 63011 reflections with 2.2<θ<28.2° using Apex2 software. Analysis of the data showed 0% decay during data collection. Data were corrected for absorption effects with the Semi-empirical from equivalents method using SADABS (Sheldrick, 1996). The minimum and maximum transmission coefficients were 0.795 and 0.887. The structure was solved and refined using the SHELXS-97 (Sheldrick, 1990) and SHELXL-97 (Sheldrick, 1997) software in the space group P-1 with Z=8 for the formula unit $Na_4[(C_2HF_3O_2)@(C_{62}H_{68}N_{16}O_{24}S_4)].\sim10(C_2HF_3O_2).\sim12.5H_2O$ 2. The final anisotropic full-matrix least-squares refinement on $F^2$ with 2219 variables converged at $R_1$=10.80% for the observed data and $wR_2$=23.75% for all data. The goodness-of-fit was 1.000. The largest peak on the final difference map was 1.05ge/A3 and the largest hole was −1.071e/A3. On the basis of the final model, the calculated density was 1.579 g/cm$^3$ and F(000), 6372 $\bar{e}$.

Example 4

Procedure to Measure the Solubility of Pharmaceutical Agents with Motor1 or Motor2

Into a solution of Motor1 or Motor2 in deuterated sodium phosphate buffer (20 mM, pD=7.4) at a known concentration, excess amount of pharmaceutical agent was added. The suspended mixture was magnetically stirred at room temperature for 12 h. During this period, the pD value of the solution was monitored and adjusted back to 7.4 if it changed. The mixture was then centrifuged twice (4200 rpm, 10 min). The concentration of pharmaceutical agent in the supernatant solution was determined by $^1$H NMR (400 MHz) spectroscopy by comparing the integral of a known concentration of 1,3,5-benzenetricarboxylic acid as internal standard with selected $^1$H NMR resonances for the pharmaceutical agent.

Procedure to Measure the Solubility of Pharmaceutical Agents Alone.

Excess amount of the pharmaceutical agent was added into sodium phosphate buffer (20 mM, pH=7.4, 100 mL). The mixture was stirred at room temperature for 12 h. Then the mixture was centrifuged twice (4200 rpm, 10 min.). The solvent of the supernatant was removed by rotary evaporation and then the resulting solid was further dried on high vacuum for 6 h. The residual solid was dissolved in either DMSO-d$_6$ or CDCl$_3$. The concentration of pharmaceutical agent was measured by $^1$H NMR (400 MHz) spectroscopy by comparing the integral of a known concentration of 1,3,5-benzenetricarboxylic acid or 1,4-dioxane as internal standard with selected $^1$H NMR resonances for the pharmaceutical agent. These procedures were repeated at a series of Motor1 or Motor2 concentrations in order to construct phase-solubility diagrams (FIGS. 22-34).

Determination of the Solubility of Motor1 in Water and Neutral Buffer.

Motor1 was added in excess to 1 mL deuterium oxide or 20 mM sodium phosphate buffered D$_2$O (pD=7.4). For phosphate buffered D$_2$O, the suspension was adjusted to pD=7.4. This suspension was magnetically stirred at room temperature overnight and then centrifuged (4300 rpm) twice for 10 minutes each time. Supernatant (10 μL) and 1,3,5-benzenetricarboxylic acid (100 mM, 20 μL in D$_2$O or 10 μL in phosphate buffered D$_2$O) were added into 0.6 mL deuterium oxide (D$_2$O) solvent. The concentration of Motor1 was measured with $^1$H NMR and calculated using 1,3,5-benzenetricarboxylic acid as internal reference. Similar methods were used to determine the intrinsic solubility of Motor2 and solubility enhancement of Motor2 toward pharmaceutical agents.

Example 5

Determination of the Solubility of Motor1 in Water

The use of CB[n]-type molecular containers in a variety of applications has been hampered by their poor solubility in aqueous solution. For example, of the CB[n] compounds that exhibit good binding properties (CB[6], CB[7], CB[8], and CB[10]) only CB[7] has a solubility that exceeds 100 μM (Solubility of CB[7]≈20 mM). We determined the inherent solubility of Motor1 in pure water (346 mM) and in 20 mM Experimental Procedure: Solid Motor1 was added to 1 mL deuterium oxide or 20 mM sodium phosphate buffered D$_2$O (pD=7.4) until solid Motor1 remained insoluble. For phosphate buffered D$_2$O, the suspension was adjusted to pD=7.4. This suspension was magnetically stirred at room temperature overnight and then centrifuged (4300 rpm) twice for 10 minutes each time. To quantitate the concentration of Motor1 in the supernatant we used $^1$H NMR spectrospcopy. Aliquots of the supernatant (10 μL) and 1,3,5-benzenetricarboxylic acid (100 mM, 20 μL in D$_2$O or 10 μL in phosphate buffered D$_2$O) were added to 0.6 mL deuterated solvent. The concentration of Motor1 was calculated by measuring the relative integrals for Motor1 versus the known concentration of 1,3,5-benzenetricarboxylic acid by $^1$H NMR.

Determination of $K_a$ Between Motor1 and Various Compounds.

Once we had determined the extremely high solubility of Motor1 in water we decided to measure its binding toward guests, which include, rhodamine 6G, crystal violet dye, 1,4-phenylene diamine, 1,4-butanediamine, and succinyl choline. It is generally possible to measure $K_a$ values up to $10^4$ M$^{-1}$ by $^1$H NMR spectroscopic methods. For values that exceed this level it is necessary to use other techniques like UV/Vis, Fluorescence, or isothermal titration calorimetry. We decided to use UV/Vis spectroscopy. The direct titration of fixed concentrations of UV/Vis Rhodamine 6G or Crystal Violet dye with Motor1 allowed us to determine their values of $K_a$ given in Table 1 by fitting to a 1:1 binding model. To determine the value of $K_a$ for Motor1 toward guests benzene 1,4-diamine, butane 1,4-diamine, and succinyl chloride which are not UV/Vis active we used an indicator displacement assay involving the addition of guest to a solution of Motor1 and Rhodamine 6G or Crystal Violet dye. The change in UV/Vis absorbance as the concentration of guest increases can be fitted to a competitive binding model which allows determination of the remaining $K_a$ values given in Table 1.

TABLE 1

Binding constants of guests with Motor1 (20 mM sodium phosphate, pH = 7.4).

| Guest | $K_a$ |
|---|---|
| Rhodamine 6G | 4.8 ± 0.1 × 10$^5$ |
| Crystal Violet Dye | 5.2 ± 0.8 × 10$^6$ |
| benzene-1,4-diamine | 3.5 ± 0.2 × 10$^5$ |
| butane-1,4-diamine | 1.2 ± 0.1 × 10$^5$ |
| succinyl choline | 1.9 ± 0.1 × 10$^5$ |

$_a$Obtained by competitive indicator displacement assay with rhodamine 6G.

Example 6

Binding Constant Determination of Motor1 Toward Taxol

Binding constant was calculated based on 1:1 drug/excipient inclusion complex formation according to literature method. Equation S1 was used to calculate $K_a$. (S1) $K_a$=Slope/[$S_0$(1-Slope)] where $S_0$ is the intrinsic solubility of the pharmaceutical agent, and Slope is the slope of the linear part of the phase-solubility diagram. The linear part of the phase-solubility diagram was used to determine the slope. The slope value along with the intrinsic concentration give a $K_a$ value of $1.9 \times 10^4$ $M^{-1}$.

Binding Constant Determination of Motor1 Toward Tamoxifen.

Binding constant was calculated based on 1:1 drug/excipient inclusion complex formation according to literature method. Equation S1 was used to calculate $K_a$. (S1) $K_a$=Slope/[$S_0$(1-Slope)] where $S_0$ is the intrinsic solubility of the pharmaceutical agent, and Slope is the slope of the linear part of the phase-solubility diagram. The linear part of the phase-solubility diagram was used to determine the slope. The slope value along with the intrinsic concentration give a $K_a$ value of $3.7 \times 10^3$ $M^{-1}$.

Binding Constant Determination of Motor2 Toward Taxol.

Binding constant was calculated based on 1:1 drug/excipient inclusion complex formation according to literature method. Equation S1 was used to calculate $K_a$. (S1) $K_a$=Slope/[$S_0$(1-Slope)] where $S_0$ is the intrinsic solubility of the pharmaceutical agent, and Slope is the slope of the linear part of the phase-solubility diagram. The slope value along with the intrinsic solubility give a $K_a$ value of $3.1 \times 10^4$ $M^{-1}$.

Binding Constant Determination of Motor2 Toward Tamoxifen.

Binding constant was calculated based on 1:1 drug/excipient inclusion complex formation according to literature method. Equation S1 was used to calculate $K_a$. (S1) $K_a$=Slope$_0$/[$S_0$(1-Slope)] where $S_0$ is the intrinsic solubility of the pharmaceutical agent, and Slope is the slope of the linear part of the phase-solubility diagram. The slope value along with the intrinsic solubility give a $K_a$ value of $1.2 \times 10^4$ $M^{-1}$.

Example 7

Toxicity Studies

To measure the cellular toxicity of Motor1 we use two complementary assays: an MTS (CellTiter 96 AQueous Kit®) assay that measures cellular metabolism, and a cytotoxicity assay (Toxilight® BioAssay Kit) that measures cell death via the release of the cytosolic enzyme adenylate kinase (AK) into the supernatant. Both assays were used with two different cell lines commonly used in drug toxicity studies, HEK293 and HepG2 cell lines. HEK293, a human kidney cell line, is used to assess the effect of the drug candidate on the renal system and HepG2, a human hepatocyte cell line, is used to assess the response of liver cells where drugs are metabolized. Both assays included the use of an untreated population, and cells treated with distilled water, erythromycin and erythromycin estolate and the test compounds for 48 h. Erythromycin is a commercially available drug widely used to treat bacterial infections. Erythromycin estolate, however, is a derivative with high toxicity. Erythromycin, with an $EC_{50}$ value of 594 (±194) μM is significantly less toxic compared to erythromycin estolate, which has an $EC_{50}$ of 109 (±7) μM. These two drugs were chosen specifically to serve as a point of comparison for the levels of cytotoxicity resulting from Motor1.

Both cell lines were incubated with the containers (0.01, 0.1, 1 and 10 mM) for 2 days prior to analysis with the two assays. Relative absorbance and luminescence data was normalized to percent cell viability (MTS) and cell death (AK). For the MTS assay, the untreated cells were set at 100% cell viability while the cell population treated with distilled water was set at a 100% cell death for the AK assay.

Figure 38:
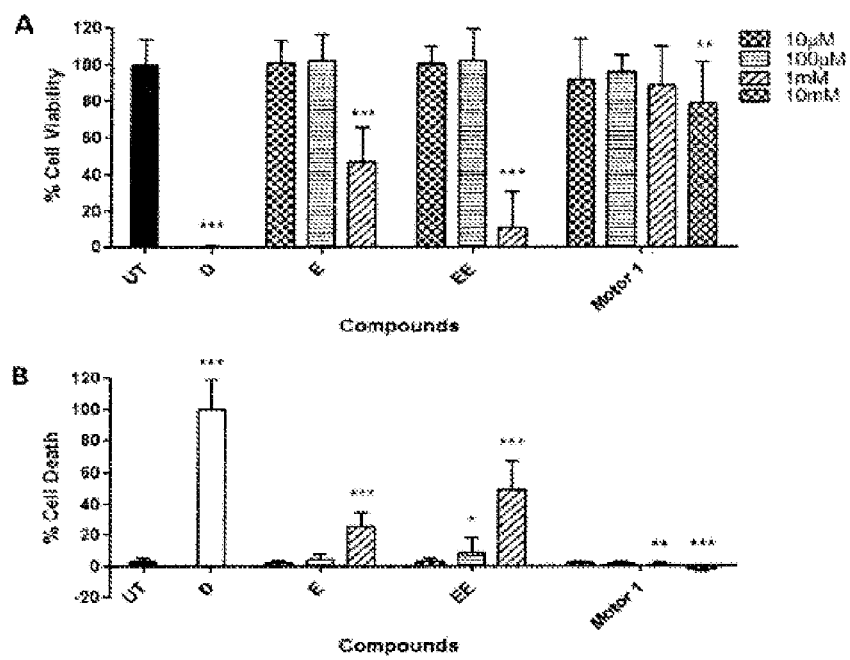
FIG. 38. Toxicology of Motor1 using the human kidney cell line HEK293. (A) MTS assay (B) AK (AK=adenylate kinase) assay. Untreated population (UT), Distilled water (D), Erythromycin (E), Erythromycin Estolate (EE).

The MTS assay conducted on the HEK293 (FIG. 38A) cell line showed high cell survival for three different concentrations of Motor1 at 92, 96, 89 and 79% cell viability. However, cell populations treated with distilled water (0.2%), 1 mM of erythromycin (47%) and erythromycin estolate (11%) showed significant decrease in cell viability. The AK assay (FIG. 38B) performed on this cell line reflected these results. Percent cell death observed in the cells treated with 1 mM erythromycin and erythromycin estolate were 25 and 49% respectively. However, cell death in the untreated population and all concentrations of Motor1 was below 5%.

Figure 39:
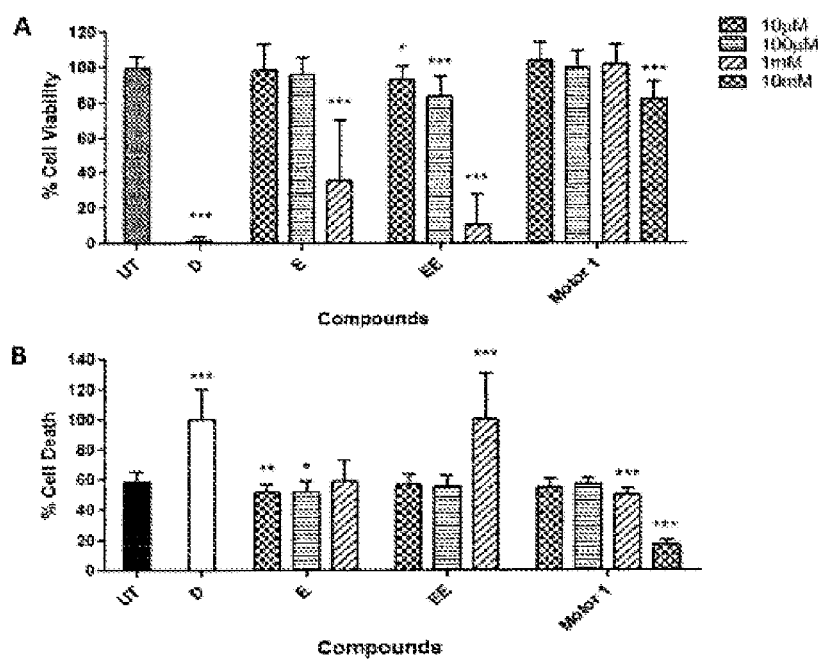
FIG. 39. Toxicology of Motor1 (1) using the human liver cell line HepG2. (A) MTS (B) AK Untreated population (UT), Distilled water (D), Erythromycin (E), Erythromycin Estolate (EE).

Similar results were observed in the HepG2 cell line (FIG. 39). The HepG2 cells treated with increasing concentrations of Motor1 showed high cell viability at 104, 100, 102 and 82% respectively in the MTS assay (FIG. 39A). These results were comparable to cell viability observed in the untreated population. However, HepG2 cells treated with distilled water (1%), 1 mM erythromycin (36%) and erythromycin estolate (10%) showed significant decreases in cell viability. These results were confirmed in the AK assay (FIG. 39B) performed using the HepG2 cell line. High percentage of cell death was observed with samples treated with erythromycin estolate at 1 mM (100% cell death). HepG2 cells exhibited high background levels in this assay as indicated by the 60% cell death in the untreated population. All cell samples treated with increasing concentrations of Motor1 show low cytotoxicity (55, 56, 50 and 17% cell death) in comparison to the untreated samples.

Overall Motor1 was found to be non-toxic in both human kidney and liver cells up to a concentration of 10 mM.

Figure 40:
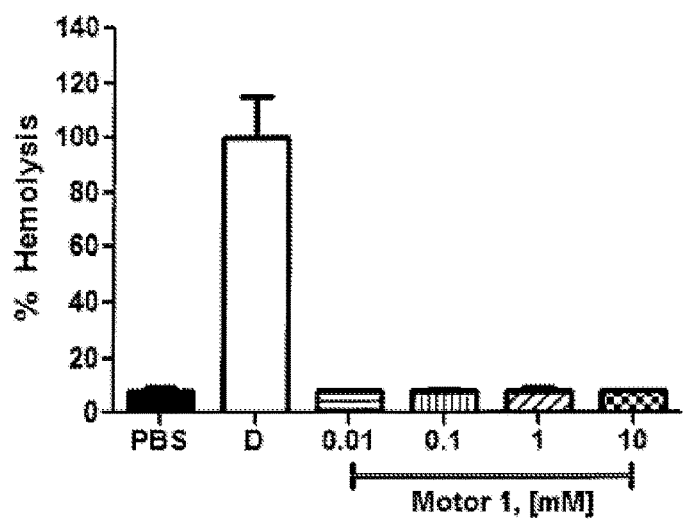
FIG. 40. Percent hemolysis at 3 h caused by increasing concentrations of the compound Motor1. Phosphate Buffer Saline (PBS), Distilled water (D).

A hemolysis assay (FIG. 40) was conducted to assess any toxic effects of Motor1 on human erythrocytes. These assays used pooled blood from two healthy donors from which red blood cells were isolated through centrifugation. Erythrocytes were exposed to phosphate buffered saline (PBS), distilled water, and increasing concentrations of Motor1 (0.01, 0.1, 1 and 10 mM). The erythrocytes were incubated shaking at 37° C. for 3 hours following treatment. The release of hemoglobin from damaged red blood cells was quantified by measuring the relative absorbance of the samples at 405 nm. Data collected was converted to percent hemolysis by setting the cell population treated with distilled water at a 100% hemolysis.

This assay showed that while erythrocytes treated with distilled water resulted in a high percentage of hemolysis, samples incubated with PBS, and increasing concentrations of Motor1 did not result in hemolysis above 20%.

Figure 41:
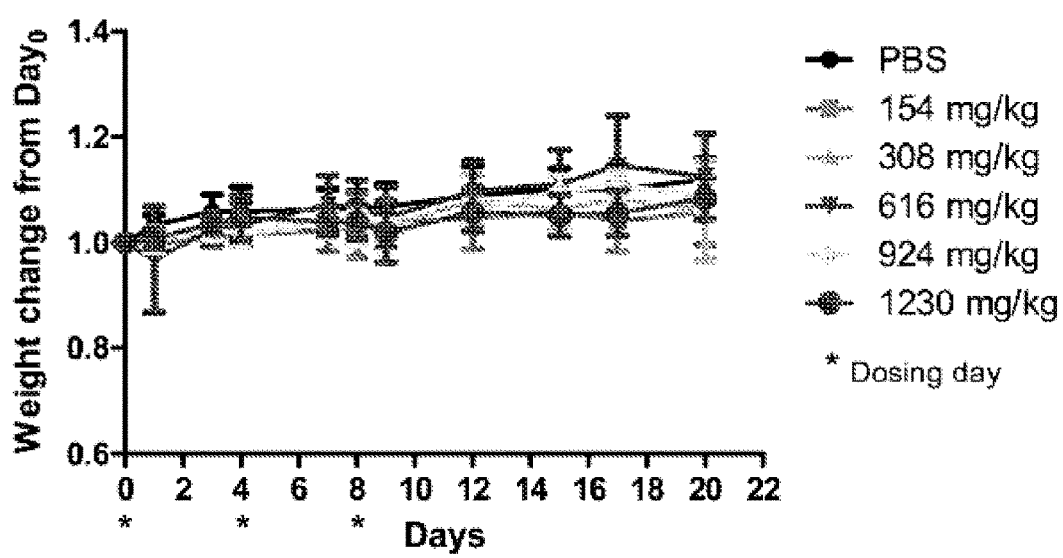
FIG. 41. Motor1 is well tolerated in mice. Indicated amounts of Motor1 were injected into the tail vein of outbred Swiss Webster mice at day 0, 4 and 8. The weight of each mouse was monitored over time and there were 5 mice per experimental group.
Figure 42:
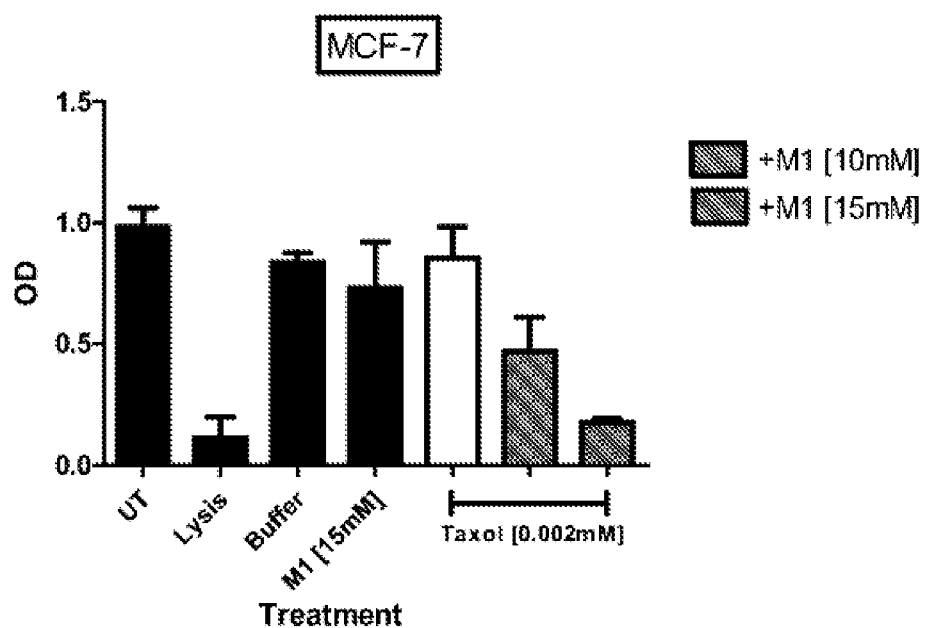
FIG. 42. Motor1 facilitates killing of cancer cells by Paclitaxel. MCF-7 cancer cells were left untreated (UT), lysed with detergent, incubated with buffer, or Motor1 alone and treated with Taxol alone or Taxol plus 10 mM Motor1 or Taxol plus 15 mM. The MTS assay was used to determine the viability of cells after 48 h of treatment as expressed in units of optical density at 405 nm.
Figure 43:
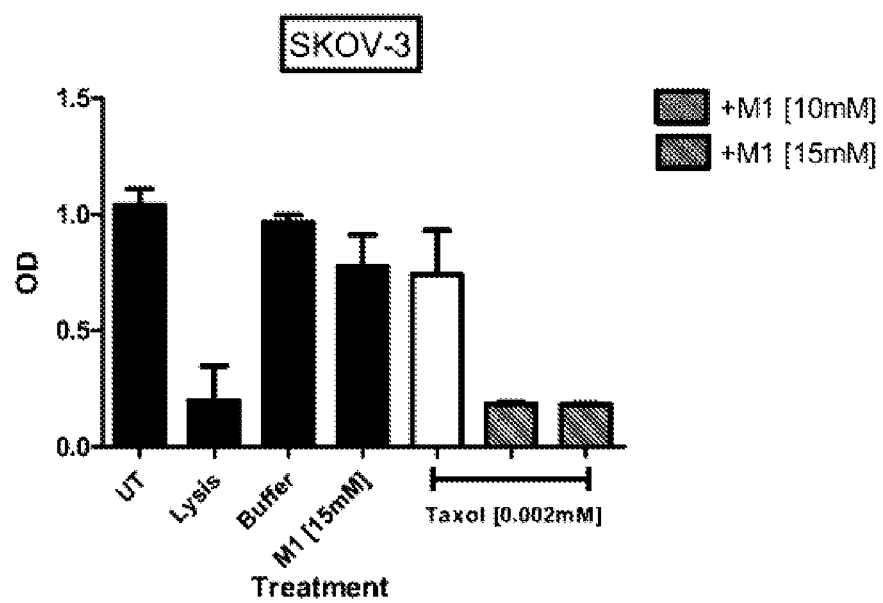
FIG. 43. Motor1 facilitates killing of cancer cells by Paclitaxel. SK-OV-3 cancer cells were left untreated (UT), lysed with detergent, incubated with buffer, or Motor1 alone and treated with Taxol alone or Taxol plus 10 mM Motor1 or Taxol plus 15 mM. The MTS assay was used to determine the viability of cells after 48 h of treatment as expressed in units of optical density at 405 nm.
Figure 44:
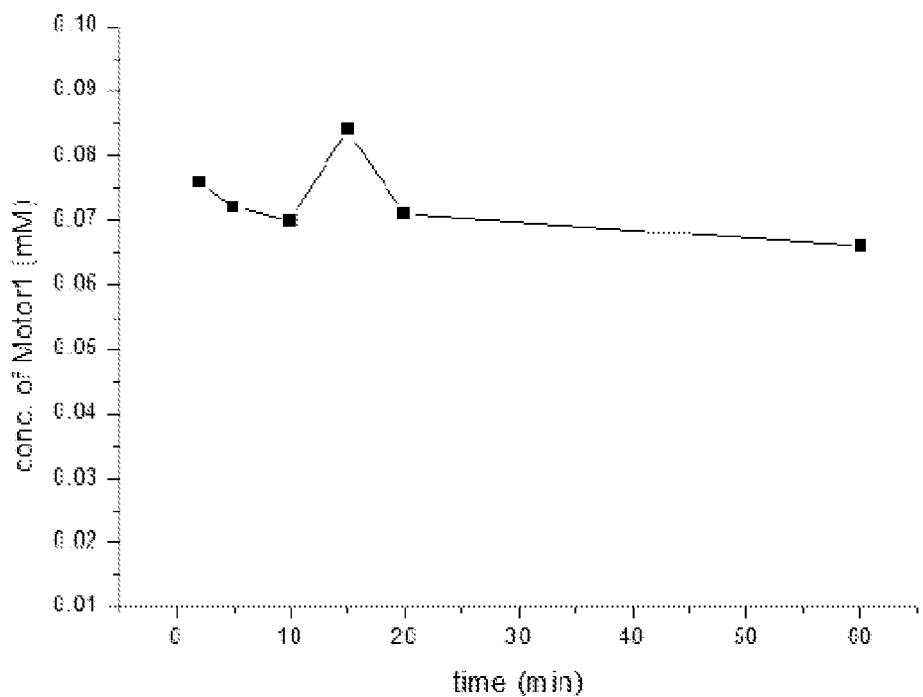
FIG. 44. An example of a concentration (mM) of Motor1 in plasma versus time (min) plot for R17.
Figure 45:
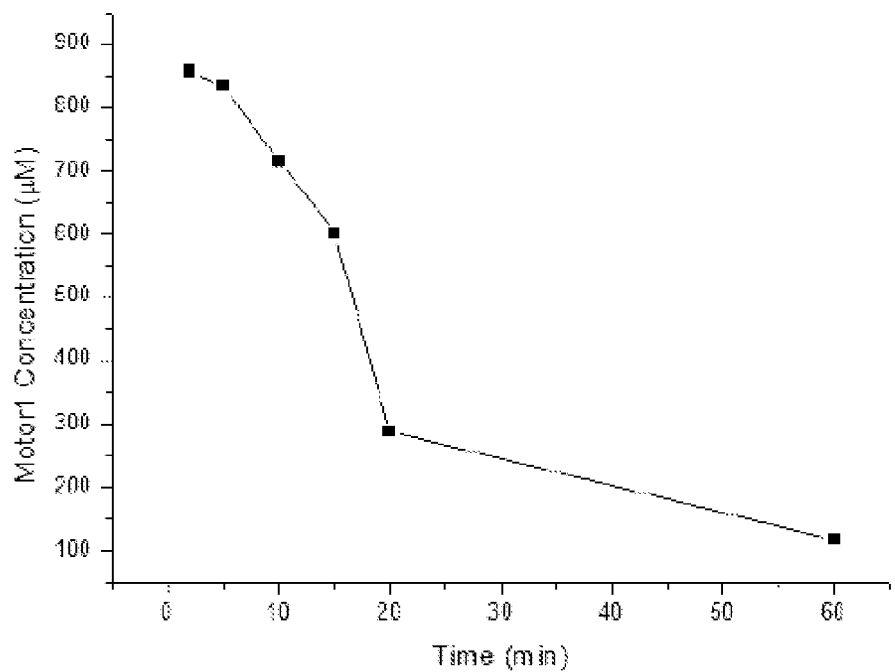
FIG. 45. An example of a concentration (mM) of Motor1 in plasma versus time (min) plot for R10.
Figure 46:
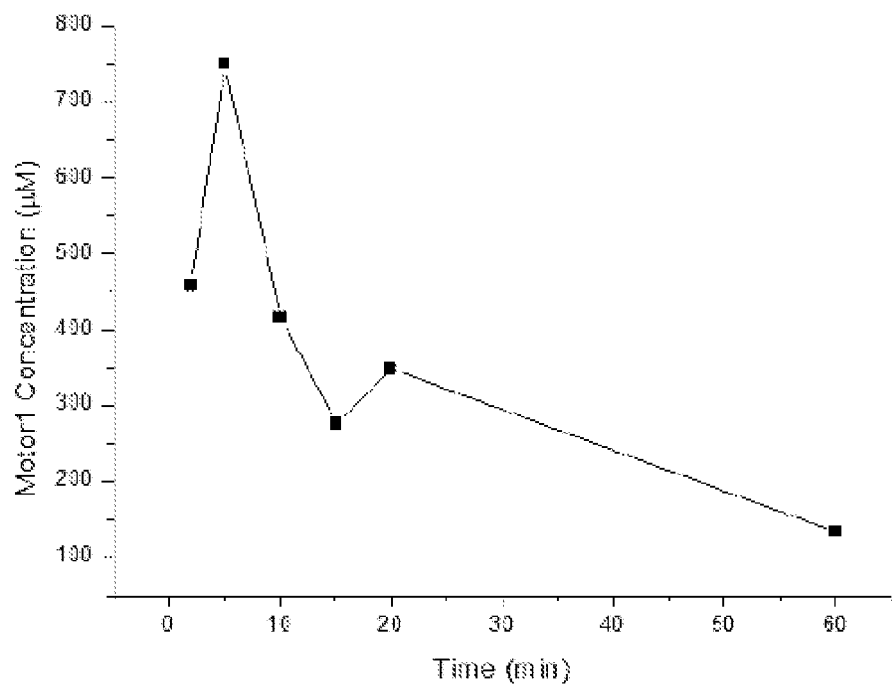
FIG. 46. An example of a concentration (mM) of Motor1 in plasma versus time (min) plot for R11.
Figure 47:
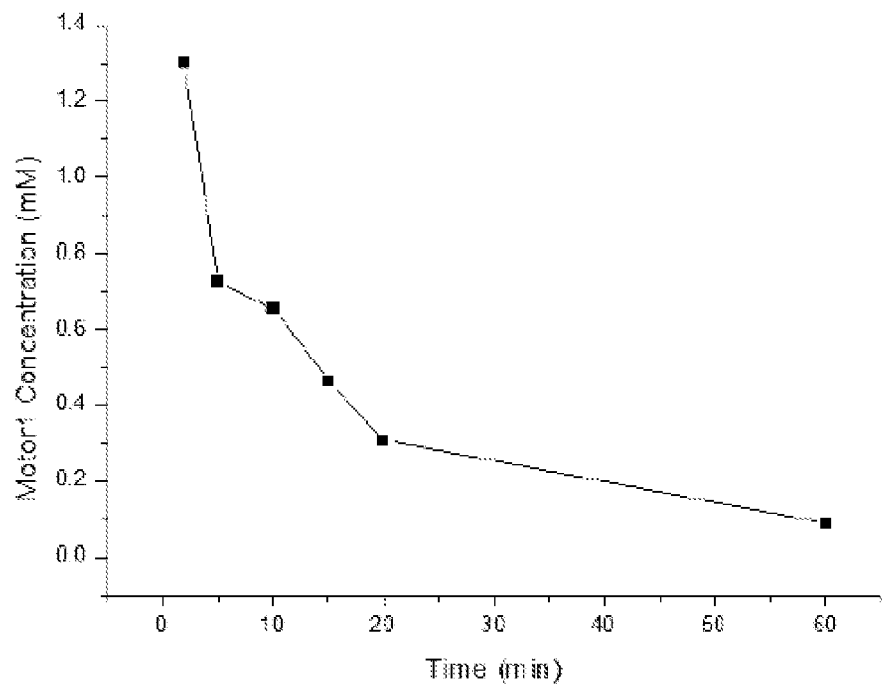
FIG. 47. An example of a concentration (mM) of Motor1 in plasma versus time (min) plot for R21.

The hemolysis assay data support the conclusion that the Motor1 is non-toxic to human erythrocytes up to a concentration of 10 mM. FIG. 41 shows Motor1 is well tolerated in mice. Indicated amounts of Motor1 were injected into the tail vein of outbred Swiss Webster mice at day 0, 4 and 8. The weight of each mouse was monitored over time and there were 5 mice per experimental group. FIG. 42 shows Motor1 facilitates killing of cancer cells by Paclitaxel. MCF-7 cancer cells were left untreated (UT), lysed with detergent, incubated with buffer, or Motor1 alone and treated with Taxol alone or Taxol plus 10 mM Motor 1 or Taxol plus 15 mM Motor1. The MTS assay was used to determine the viability of cells after 48 h of treatment as expressed in units of optical density at 405 nm. FIG. 43 shows Motor1 facilitates killing of cancer cells by Paclitaxel. SKOV-3 cancer cells were left untreated (UT), lysed with detergent, incubated with buffer, or Motor1 alone and treated with Taxol alone or Taxol plus 10 mM Motor1 or Taxol plus 15 mM. The MTS assay was used to determine the viability of cells after 48 h of treatment as expressed in units of optical density at 405 nm.

We measured in vivo clearance of compounds of the invention via urine. For urine samples (Table 2), we took 0.1 mL from each urine sample and dried them under high vacuum. Then they were dissolved in 0.5 mL D20, and 0.1 mL of 60 mM reference solution (1,3,5-tricarboxylate benzene) was added. NMR spectra were taken and the concentration of Motor1 in urine was calculated from the ratio between the integration of diagnostic peak for reference (8.3 ppm, 3H) and Motor1 (1.9-1.5 ppm, 12H).

TABLE 2

| Sample No. | Urine volume (μL) | Integral * | [Motor 1] (mM) | [Motor 1] (mg/mL) | Mass (Motor 1) (mg) | Notes |
|---|---|---|---|---|---|---|
| R1U | 930 | 3.34 | 6.958 | 10.723 | 9.972 | |
| R2U | 530 | 0.06 | 0.125 | 0.193 | 0.102 | Blood in urine |
| R3U | 580 | 10.25 | 21.354 | 32.907 | 19.086 | |
| R4U | 240 | 8.88 | 18.500 | 28.509 | 6.842 | Precipitate in urine |
| R5U | 1350 | 0.00 | 0.000 | 0.000 | 0.000 | |
| R6U | 415 | 0.00 | 0.000 | 0.000 | 0.000 | |
| R7U | 725 | 5.72 | 11.917 | 18.364 | 13.314 | |
| R8U | 610 | 13.78 | 28.708 | 44.240 | 26.986 | |
| R9U | 950 | 4.21 | 8.771 | 13.516 | 12.840 | |
| R10U | 315 | 8.70 | 18.125 | 27.931 | 8.798 | |
| R11U | 560 | 1.03 | 2.146 | 3.307 | 1.852 | |
| R12U | | | | | | N/A |
| R13U | 815 | 0.00 | 0.000 | 0.000 | 0.000 | |
| R14U | 355 | 10.62 | 22.125 | 34.095 | 12.104 | |
| R15U | 305 | 6.88 | 14.333 | 22.088 | 6.737 | Blood in urine |
| R16U | 455 | 12.28 | 25.583 | 39.424 | 17.938 | |
| R17U | 255 | 10.74 | 22.375 | 34.480 | 8.792 | |
| R18U | 610 | 0.00 | 0.000 | 0.000 | 0.000 | |
| R19U | 615 | 1.27 | 2.646 | 4.077 | 2.507 | Precipitate in urine |
| R20U | 190 | 5.39 | 11.229 | 17.304 | 3.288 | Precipitate in urine |
| R21U | 585 | 2.40 | 5.000 | 7.705 | 4.507 | |
| R22U | 390 | 0.00 | 0.000 | 0.000 | 0.000 | Precipitate in urine |

For Plasma samples, four rats in total have been tested: Rat 10, Rat 17, Rat 11, Rat 21. For each plasma sample, 10 μL of plasma was taken and dried under high vacuum. Excess amount of probe solution was added (495 μL of 38 μM p-xylenediamine) to dissolve the residue and then the reference (5 μL of 600 μM benzene-1,3,5-tricarboxylic acid) was added. NMR spectra was taken with water suppression and the concentration of Motor1 was calculated from the ratio between the integrations of the peaks for the reference (8.2 ppm, 3H) and Motor1 (6.5 ppm, 4H). For Rat 17, benzene-1,3,5-tricarboxylic acid was not used, but p-xylenediamine was used as the reference (FIGS. 44-47).

Figure 48:
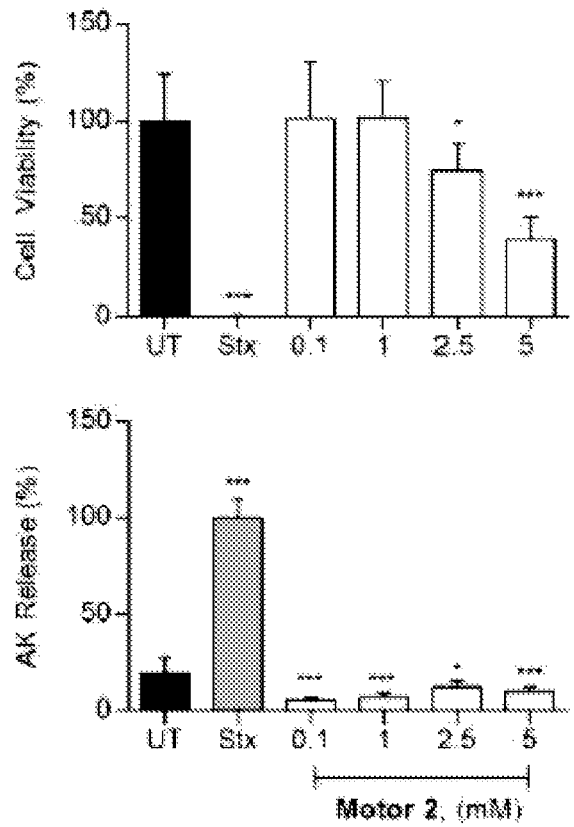
FIG. 48. Varying concentrations of Motor2 incubated with THP-1 (A) and HEK 293 (B) cells over a 48 hr period resulted in high cell survival up to 5 mM. Two complementary assays were used to analyze toxicology an MTS and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P,0.001 for the statistical analysis of all figures presented.
Figure 48:
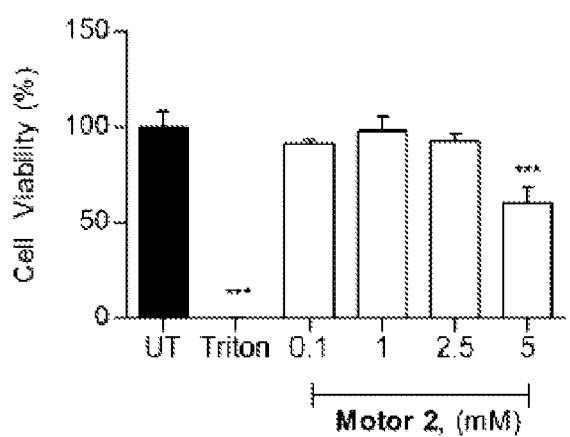
Figure 49:
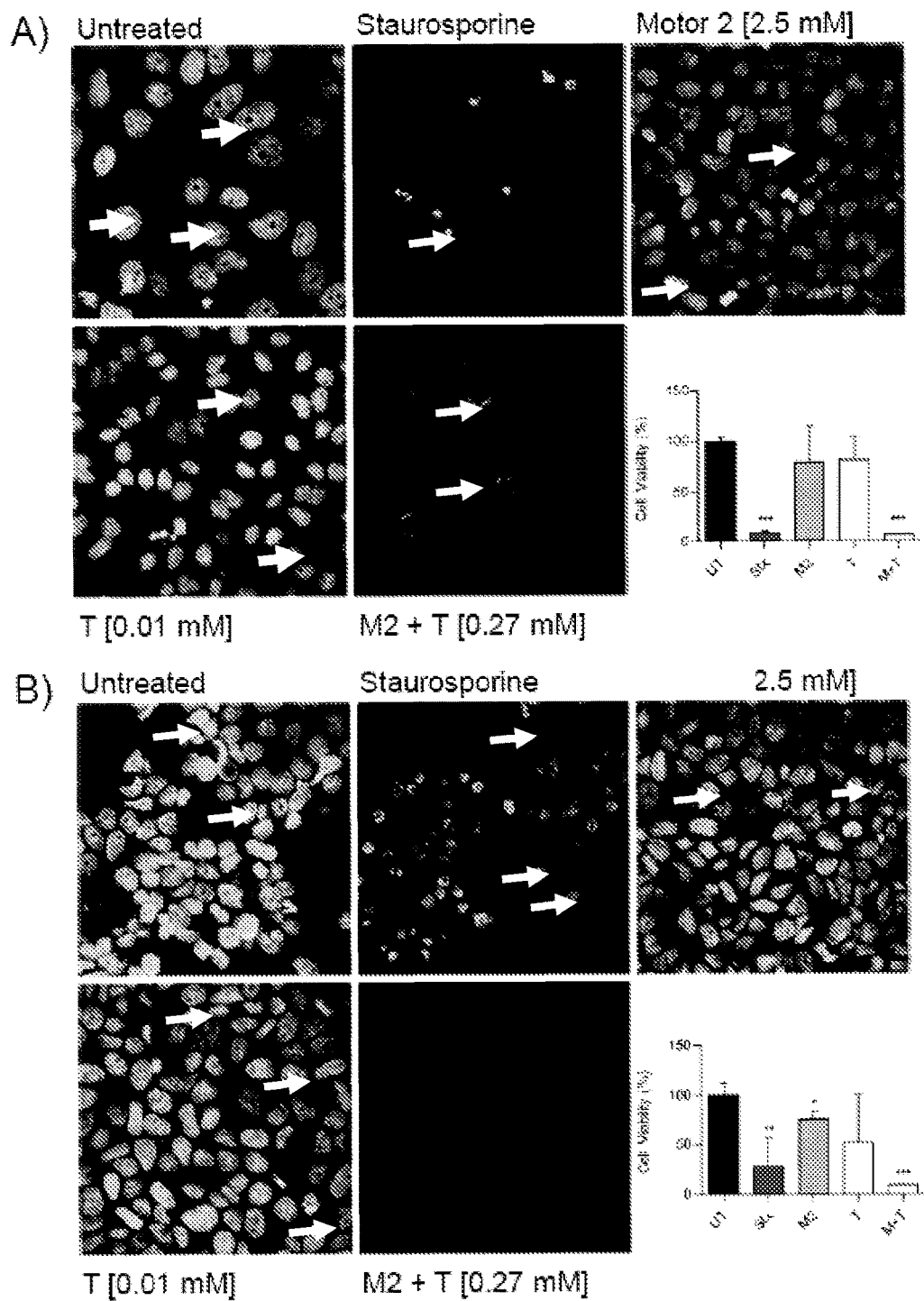
FIG. 49. In vitro Bioactivity of Motor2. Hela (A) and MCF-7 (B) cells treated for 24 hrs with Tamoxifen complexed to Motor2 showed a significant increase in cell death as a result of the increase in Tamoxifen (0.27 mM) solubility once complexed to the container. Tamoxifen (0.01 mM) alone in phosphate buffer showed little to no cell death in comparison to the untreated samples as did the Motor2 (2.5 mM) alone treatments indicating the container alone did not result in cancer cell death. MTS analysis of the Hela (A), and MCF (B) showed high cell survival for M2 and Tamoxifen alone treatments and very low cell survival for the drug-container complex (green (designated by arrows here and in FIG. 41)=nuclei, red=actin, Stx=Staurosporine, Tamoxifen=T, Motor2=M2).
Figure 50:
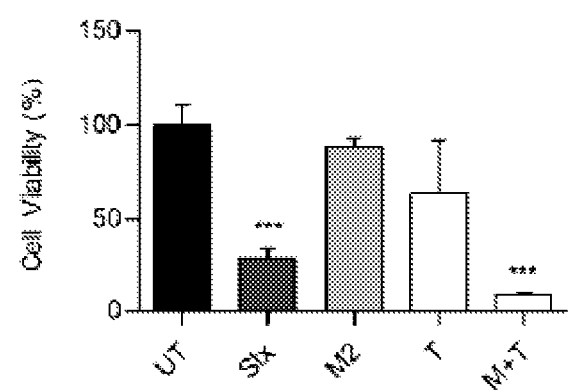
FIG. 50. MTS analysis of SK-OV-3 cancer cells after a 48 hr treatment with staurosporine (Stx), Motor2 at 2.5 mM (M2), Tamoxifen (0.01 mM), Motor2 complexed with 0.27 mM Tamoxifen (M+T).

FIG. 48 shows toxicology studies performed using Motor2. Varying concentrations of Motor2 incubated with THP-1 (A) and HEK 293 (B) cells over a 48 hr period resulted in high cell survival up to 5 mM Motor2. Two complementary assays were used to analyze toxicology: an MTS assay and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P,0.001 for the statistical analysis of all figures presented. FIG. 49 shows in vitro Bioactivity studies using Motor2. Hela (A) and MCF-7 (B) cells treated for 24 hrs with Tamoxifen complexed with Motor2 showed a significant increase in cell death as a result of the increase in Tamoxifen (0.27 mM) concentration once complexed by the container. Tamoxifen (0.01 mM) alone in phosphate buffer showed little to no cell death in comparison to the untreated samples as did treatment with Motor2 (2.5 mM) alone which indicates the container alone did not result in cancer cell death. MTS analysis of the data obtained for Hela (A), and MCF (B) cells showed high cell survival for treatment with Motor2 or Tamoxifen alone whereas treatment with Tamoxifen complexed with Motor2 showed very low cell survival (green=nuclei, red=actin, Stx=Staurosporine, Tamoxifen=T, Motor2=M2). FIG. 50 shows MTS analysis of SK-OV-3 after a 48 hr treatment. MTS=(3-(4,5-dimethylthiazol-2-yl)-5-(3-carboxymethoxyphenyl)-2-(4-sulfophenyl)-2H-tetrazolium).

Figure 51:
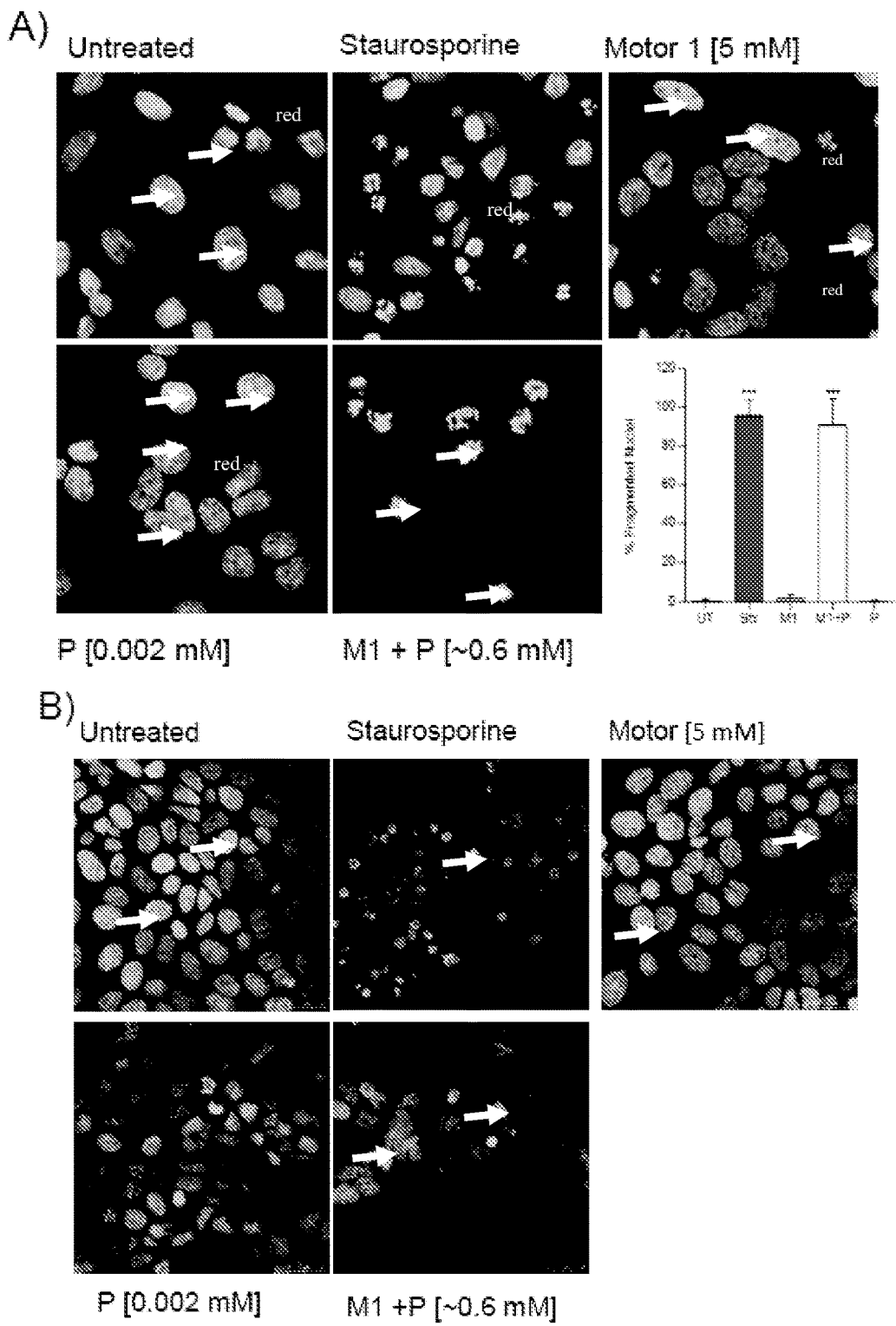
FIG. 51. HeLa (A) and MCF-7 (B) cells treated with Paclitaxel complexed to Motor1 showed increased DNA fragmentation and cell death as a result of the significant increase in Paclitaxel (0.6 mM) solubility once complexed to the container. Paclitaxel (0.002 mM) alone in phosphate buffer showed little to no cell death in comparison to the untreated samples as did the Motor 1 (5 mM) alone treatments indicating that Motor1 alone did not result in cancer cell death (green=nuclei, red=actin, Paclitaxel=P, Motor1=M1).

FIG. 51 shows in vitro bioactivity. Hela (A) and MCF-7 (B) cells treated with Paclitaxel complexed with Motor1 showed increased DNA fragmentation and cell death as a result of the significant increase in Paclitaxel (0.6 mM) solubility once complexed to the container. Paclitaxel (0.002 mM) alone in phosphate buffer showed little to no cell death in comparison to the untreated samples as did the Motor1 (5 mM) alone treatments indicating the container alone did not result in cancer cell death (green=nuclei, red=actin, Paclitaxel=P, Motor 1=M1). FIG. 54 shows toxicology using Motor 2. Varying concentrations of Motor 2 incubated with THP-1 (A) and HEK 293 (B) cells over a 48 hr period resulted in high cell survival up to 5 mM. Two complementary assays were used to analyze toxicology an MTS and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P,0.001 for the statistical analysis of all figures presented.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A composition comprising a pharmaceutical agent, wherein the pharmaceutical agent has a solubility of 33 mg/mL to less than 0.1 mg/mL in an aqueous solvent, wherein the pharmaceutical agent is non-covalently complexed to a compound having the following structure:

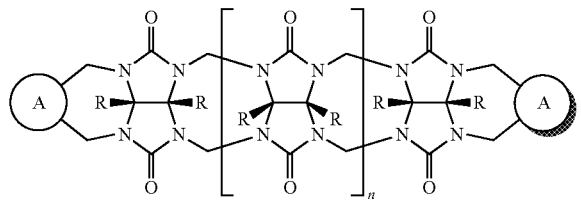

or a salt, a partial salt, a hydrate, or a stereoisomer thereof, wherein each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy, or ether group;

wherein, optionally, adjacent R groups form a $C_3$ to $C_{20}$ carbocyclic ring or heterocyclic ring;

wherein each

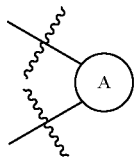

is independently a $C_5$ to $C_{20}$ carbocyclic ring system or $C_2$ to $C_{20}$ heterocyclic ring system, wherein the ring system comprises one or more rings;

wherein at least one ring system has at least one solubilizing group selected from sulfonic acid group, sulfonate salt group, phosphonic acid group, phosphonate salt group, and polyethylene glycol group;

wherein, optionally, the ring system has a targeting group;

wherein n is 1 to 5.

2. The composition of claim 1, wherein each

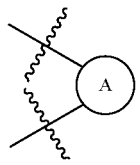

of the compound is independently a $C_5$ to $C_{20}$ carbocyclic ring system having one of the following structures:

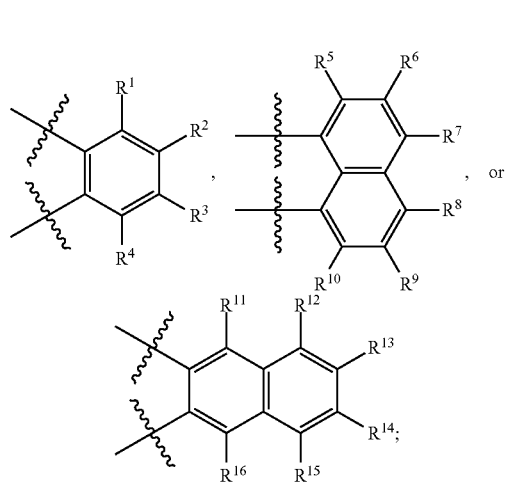

wherein at each occurrence of

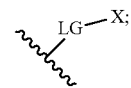

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group, provided that at least one of $R^1$ to $R^{16}$ in the compound has the following structure:

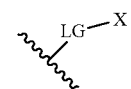

wherein LG is a linking group and X is the solubilizing group; and wherein optionally one or more adjacent $R^1$ to $R^{16}$ groups are connected forming a carbocyclic ring or heterocyclic ring.

3. The composition of claim 2, wherein

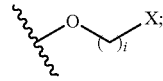

in the compound has the following structure:

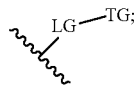

wherein each i is 1 to 20.

4. The composition of claim 2, wherein at least one of the $R^1$ to $R^{16}$ groups in the structure of the compound has the following structure

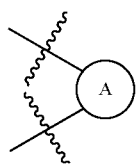

and wherein LG is a linking group and wherein TG is the targeting group.

5. The composition of claim 2, wherein the

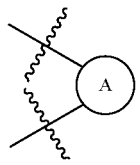

groups of the compound are the same.

6. The composition of claim 3, wherein the compound has one of the following structures:

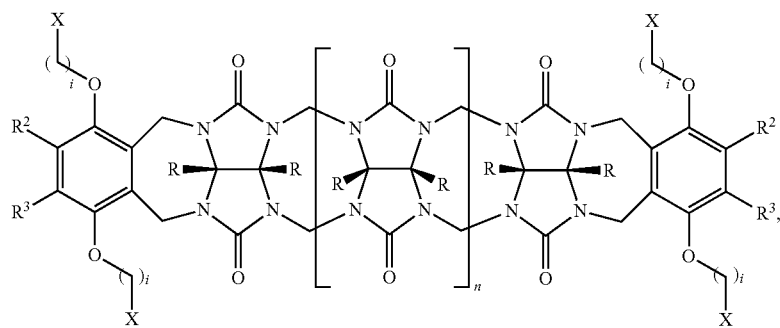
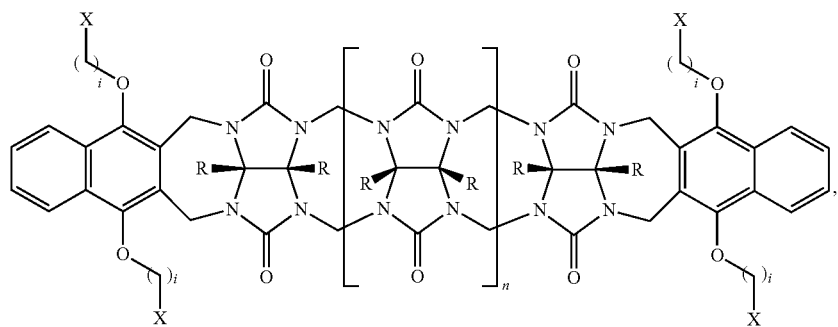
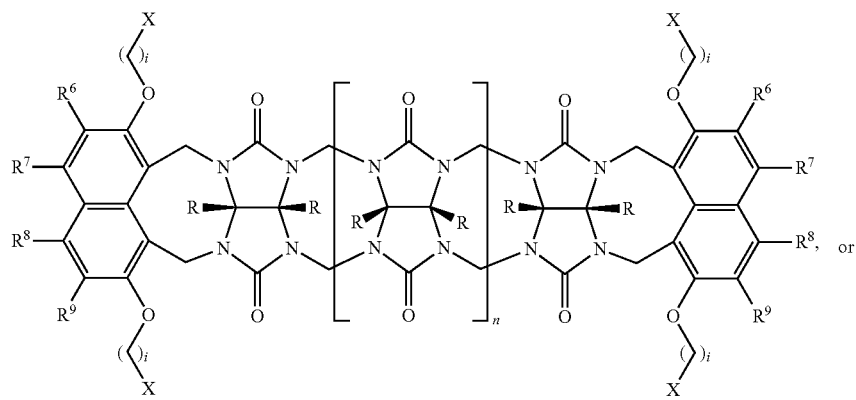
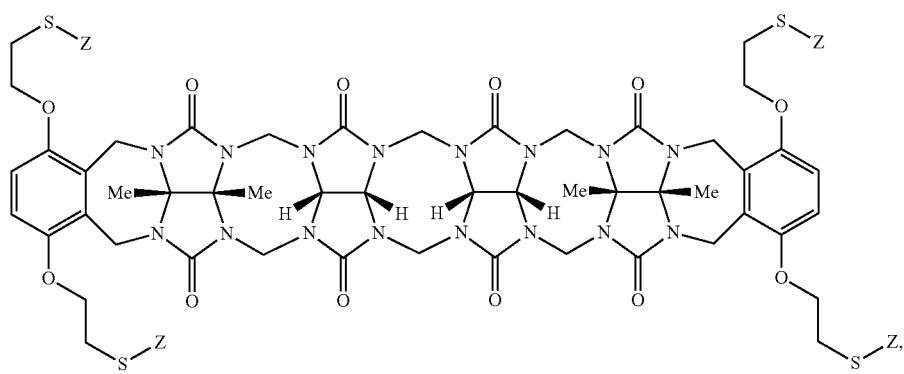
wherein Z is PEG group having a molecular weight of 200 to 10,000.
7. The composition of claim 1, wherein the compound has one of the following structures:

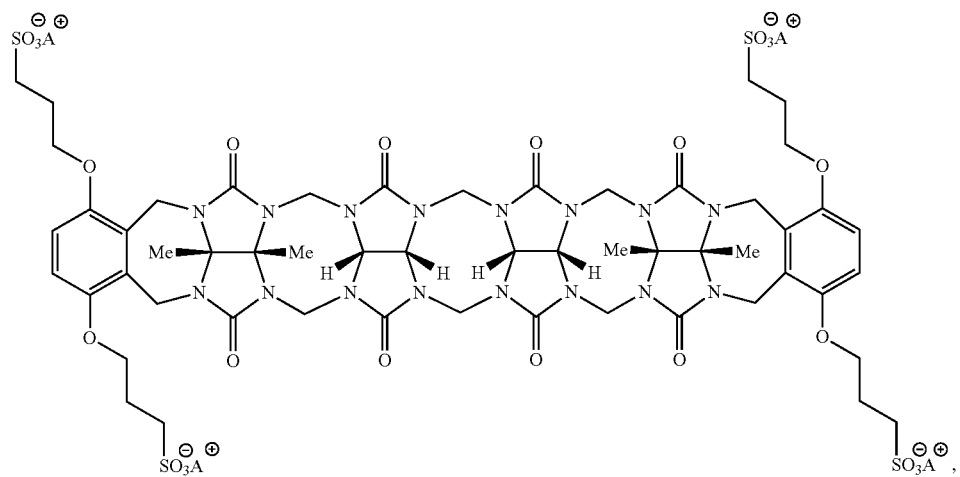
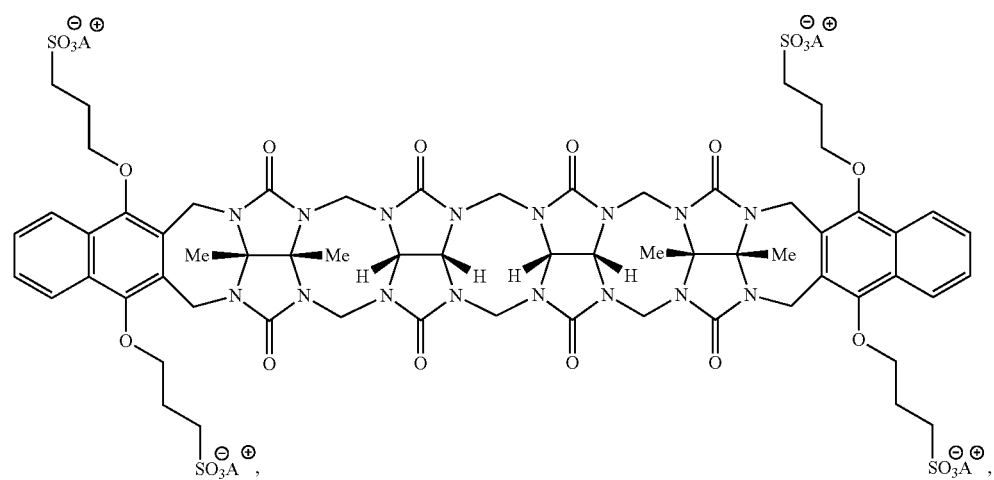
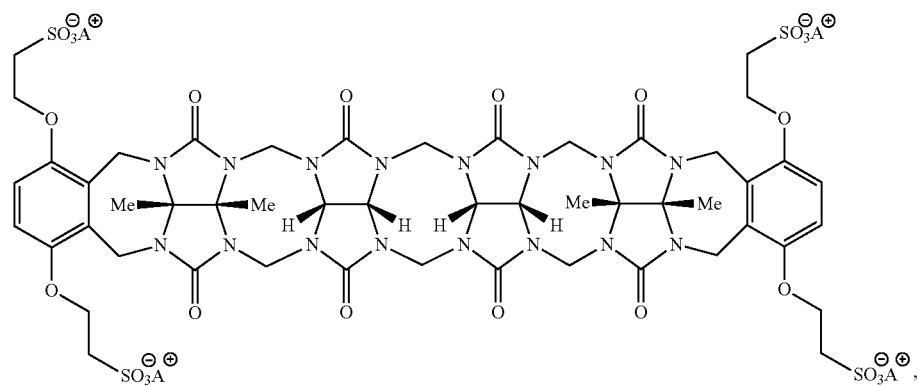

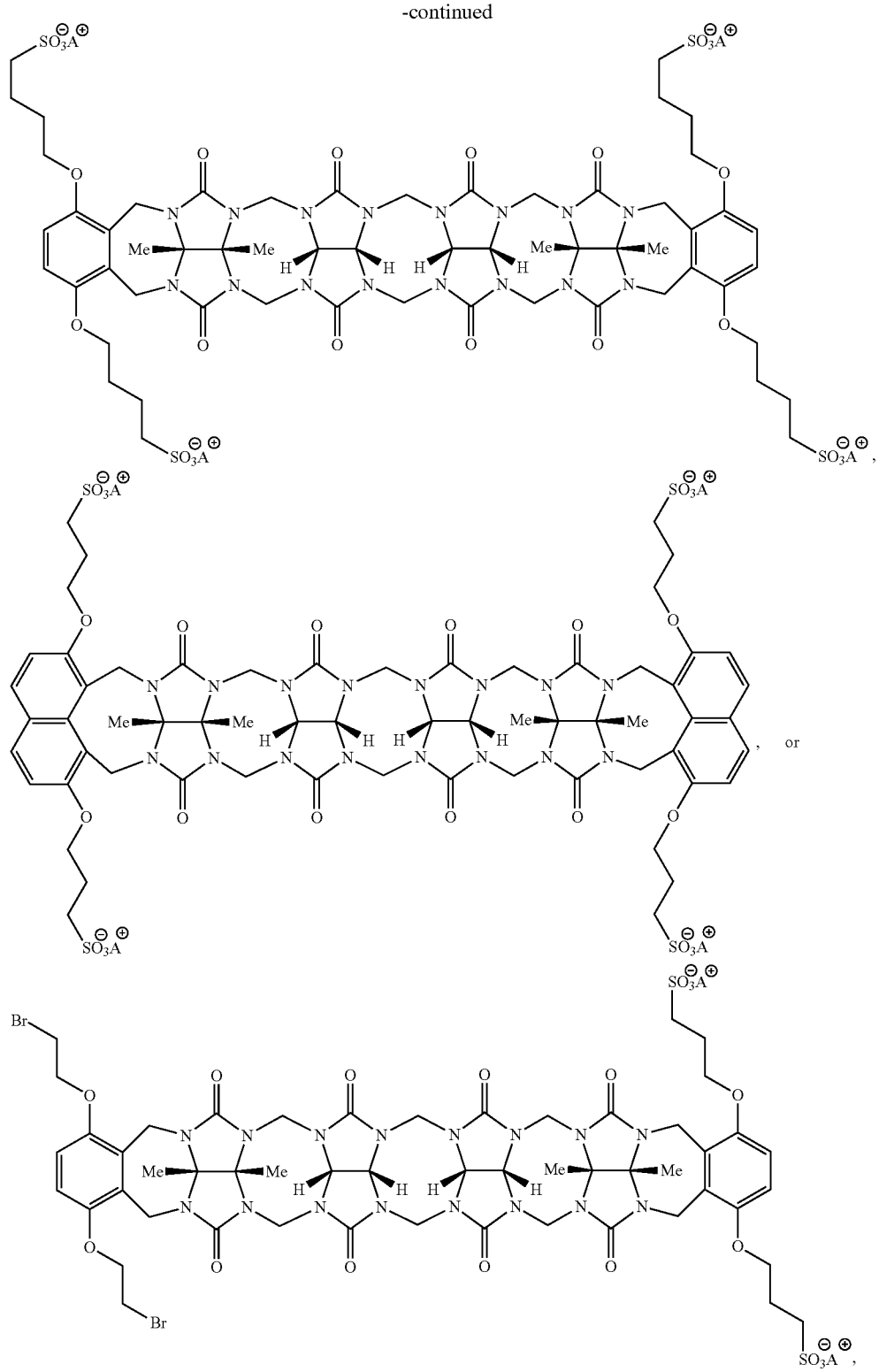
wherein $A^+$ is $H^+$, $Na^+$, $K^+$, $Ca^{2+}$, $Mg^{2+}$, $Zn^{2+}$, $H_4N^+$, $Et_3NH^+$, $Me_4N^+$, $(HOCH_2CH_2)_3NH^+$, or a cationic form of ethylenediamine, piperazine, and trishydroxymethyl aminomethane (TRIS).
8. The composition as in claim 1, wherein the pharmaceutical agent has a solubility of less than 100 μM in an aqueous solvent.
* * * * *